United States Patent
Veeravalli et al.

(10) Patent No.: US 12,291,712 B2
(45) Date of Patent: May 6, 2025

(54) METHODS OF PRODUCING TWO CHAIN PROTEINS IN PROKARYOTIC HOST CELLS

(71) Applicant: Genentech, Inc., South San Francisco, CA (US)

(72) Inventors: Karthik Veeravalli, San Francisco, CA (US); Rebekah McKenna, Hayward, CA (US)

(73) Assignee: Genentech, Inc., South San Francisco, CA (US)

( * ) Notice: Subject to any disclaimer, the term of this patent is extended or adjusted under 35 U.S.C. 154(b) by 866 days.

(21) Appl. No.: 17/307,877

(22) Filed: May 4, 2021

(65) Prior Publication Data

US 2021/0261973 A1    Aug. 26, 2021

Related U.S. Application Data

(63) Continuation of application No. PCT/US2019/059661, filed on Nov. 4, 2019.

(60) Provisional application No. 62/755,915, filed on Nov. 5, 2018.

(51) Int. Cl.
| | |
|---|---|
| *C12N 15/70* | (2006.01) |
| *C07K 16/00* | (2006.01) |
| *C07K 16/22* | (2006.01) |
| *C07K 16/24* | (2006.01) |
| *C12N 9/02* | (2006.01) |
| *C12N 9/90* | (2006.01) |

(52) U.S. Cl.
CPC ............ *C12N 15/70* (2013.01); *C07K 16/00* (2013.01); *C07K 16/22* (2013.01); *C07K 16/244* (2013.01); *C12N 9/0004* (2013.01); *C12N 9/90* (2013.01); *C12Y 502/01008* (2013.01); *C07K 2317/14* (2013.01); *C07K 2317/31* (2013.01)

(58) Field of Classification Search
CPC ........ C12N 15/70; C12N 9/0004; C12N 9/90; C07K 16/00; C07K 16/22; C07K 16/244; C07K 2317/14; C07K 2317/31; C07K 16/2863; C07K 2317/24; C07K 2317/55; C07K 2317/92; C12Y 502/01008
See application file for complete search history.

(56) References Cited

U.S. PATENT DOCUMENTS

| | | | |
|---|---|---|---|
| 6,673,569 B1 | 1/2004 | Kurokawa et al. | |
| 10,066,002 B2 | 9/2018 | Giulianotti et al. | |
| 10,112,994 B2 * | 10/2018 | Giulianotti | C07K 16/468 |
| 11,091,530 B2 | 8/2021 | Giulianotti et al. | |
| 11,299,539 B2 * | 4/2022 | Giulianotti | C12N 15/70 |
| 2003/0077739 A1 | 4/2003 | Simmons et al. | |
| 2011/0136169 A1 | 6/2011 | Anderson et al. | |
| 2014/0315245 A1 | 10/2014 | Yam et al. | |
| 2016/0159898 A1 * | 6/2016 | Giulianotti | C07K 16/468 435/69.6 |
| 2016/0376602 A1 * | 12/2016 | McClain | C12N 15/63 435/69.6 |
| 2017/0335003 A1 | 11/2017 | Ellis et al. | |
| 2019/0112368 A1 | 4/2019 | Giulianotti et al. | |

FOREIGN PATENT DOCUMENTS

| | | | |
|---|---|---|---|
| CN | 1546670 A | 11/2004 | |
| CN | 1549821 A | 11/2004 | |
| CN | 102712679 A | 10/2012 | |
| CN | 105283556 A | 1/2016 | |
| JP | 2000083670 | 3/2000 | |
| JP | 2001503249 A | 3/2001 | |
| JP | 2014521313 A | 8/2014 | |
| JP | 2018518957 A | 7/2018 | |
| WO | 9807846 A1 | 2/1998 | |
| WO | 2008142028 A1 | 11/2008 | |
| WO | WO-2011086141 A1 * | 7/2011 | ........... C07K 16/241 |
| WO | 2013007388 A1 | 1/2013 | |
| WO | 2013171156 A1 | 11/2013 | |
| WO | 2016073791 A1 | 5/2016 | |
| WO | 2016205570 A1 | 12/2016 | |
| WO | 2017106583 A1 | 6/2017 | |

OTHER PUBLICATIONS

Jensen et al., 1998, "The Sequence of Spacers between the Consensus Sequences Modulates the Strength of Prokaryotic Promoters", Applied and Environmental Microbiology, p. 82-87, on IDS dated Jan. 31, 2022 (Year: 1998).*
Bass, S. et al. (1996). "Multicopy Suppressors of Prc Mutant *Escherichia coli* Include Two HtrA (DegP) Protease Homologs (HhoAB), DksA, and a Truncated RlpA." J. Bacteriol. 178(4):1154-1161.
Carlos, M.P. (1978). "DNA Sequence For a Low-Level Promoter Of The lac Repressor Gene And An 'Up' Promoter Mutation," Nature 274:762-765.
Datsenko, K.A. et al. (2000). "One-Step Inactivation of Chromosomal Genes in *Escherichia coli* K-12 Using PCR Products," Proc. Natl. Acad. Sci. USA, 97(12):6640-6645.

(Continued)

*Primary Examiner* — Terry A McKelvey
*Assistant Examiner* — Andrew T Moehlman
(74) *Attorney, Agent, or Firm* — MORRISON & FOERSTER LLP

(57) ABSTRACT

Provided herein are methods and host cells for producing a polypeptide containing two chains, such as an antibody, half-antibody, antibody fragment, or one-armed antibody. The methods and host cells allow for two-chain polypeptide production using expression of polynucleotides encoding the polypeptide chains from extra-chromosomal polynucleotide(s), and expression of one or more chaperone protein(s) (e.g., peptidyl-prolyl isomerases and/or protein disulfide oxidoreductases) from the host cell chromosome using non-native combination(s) of promoters and translational units encoding a chaperone protein.

15 Claims, 13 Drawing Sheets

Specification includes a Sequence Listing.

(56) References Cited

OTHER PUBLICATIONS

Deboer, H.A. et al. (1983). "The Tac Promoter: a Functional Hybrid Derived From the trp and lac Promoters," Proc. Natl. Acad. Sci. USA, 80(1):21-25.

Hsieh, Y-J. et al. (2010). "Global Regulation by the Seven-component Pi Signaling System," Curr. Opin. Microbiol. 13(2):198-203.

Innes, D et al. (2001). "The Cryptic ushA Gene (ushAc) in Naturalisolates of *Salmonella enterica* (serotype *Typhimurium*) has Been Inactivated by a Single Missense Mutation," Microbiology 147:1887-1896.

International Preliminary Report mailed May 20, 2021, For PCT Application No. PCT/US2019/059661, filed on Nov. 4, 2019, 6 pages.

International Search Report and Written Opinion mailed Apr. 23, 2020, For PCT Application No. PCT/US2019/059661, filed on Nov. 4, 2019, 15 pages.

Jensen, P.R. et al. (1998). "The Sequence of Spacers Between the Consensus Sequences Modulated the Strength of Prokaryotic Promoters," Applied and Environmental Microbiology 64(1):82-87.

Nakashima, N. et al. (2014). "Bacterial Cellular Engineering by Genome Editing and Gene Silencing," Int. J. Mol. Sci. 15:2773-2793.

Reilly, D.E. et al. (2010). "Production of Monotlonal Antibodies in *E. coli*," Chapter 17 In Current Trends In Monoclonal Antibody Development And Manufacturing, Springer, US, pp. 295-308.

Schlapschy, M. et al. (2006, e-pub. May 23, 2006). "A System for Concomitant Overexpression of Four Periplasmic Folding Catalysts to Improve Secretory Protein Production in *Escherichia coli*," Protein Engineering, Design and Selection 19(8):385-390.

Spadiut, O. et al. (2014). "Microbials for the Production of Monoclonal Antibodies and Antibody Fragments," Trends in Biotechnology 32(1):54-60.

Sullivan, M.J. et al. (2018). "Stable Expression of Modified Green Fluorescent Protein in Group B Streptococci TO Enable Visualization in Experimental Systems," Applied and Environmental Microbiology 84(18):e01262-18, 16 pages.

Terpe, K. (2006, e-pub. Jun. 22, 2006). "Overview Of Bacterial Expression Systems For Heterologous Protein Production: From Molecular and Biochemical Fundamentals To Commercial Systems," Appl. Microbiol, Biotechnol. 72:211-222.

Third Party Observation for European Patent Application No. 19836645.2, mailed on Oct. 13, 2021, 7 pages.

Zhong, Z. et al. (2018, e-pub. Sep. 24, 2018). "Production of Soluble and Functional Engineered Antibodies in *Escherichia coli* Improved by FkpA," BioTechniques 35(5):1-9.

\* cited by examiner

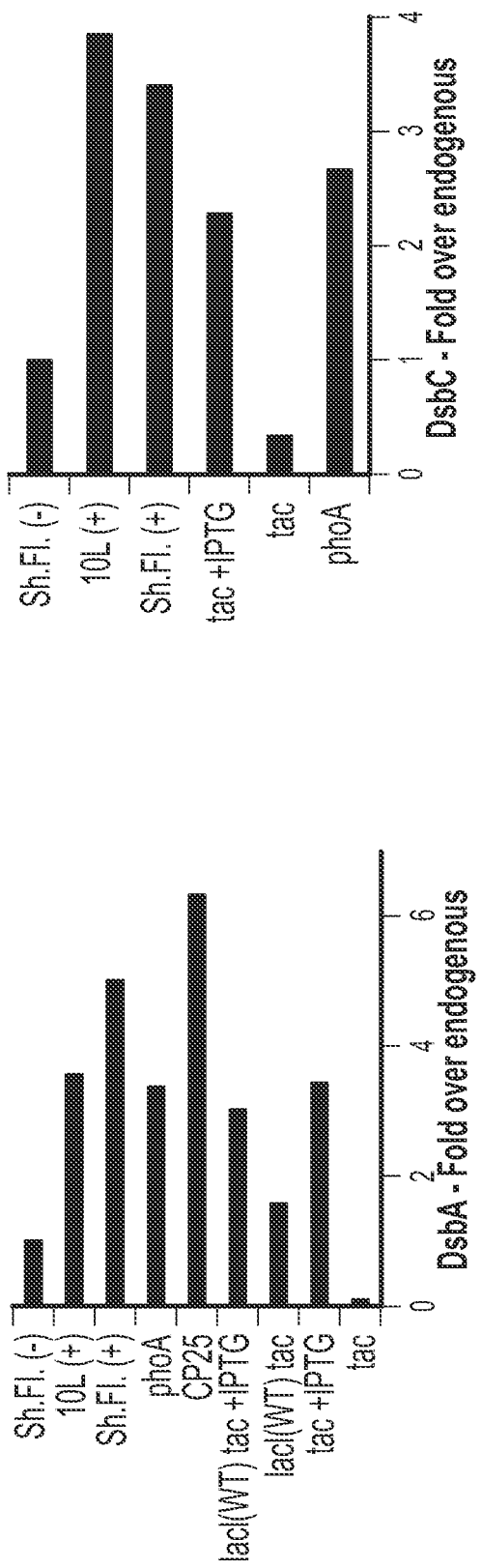
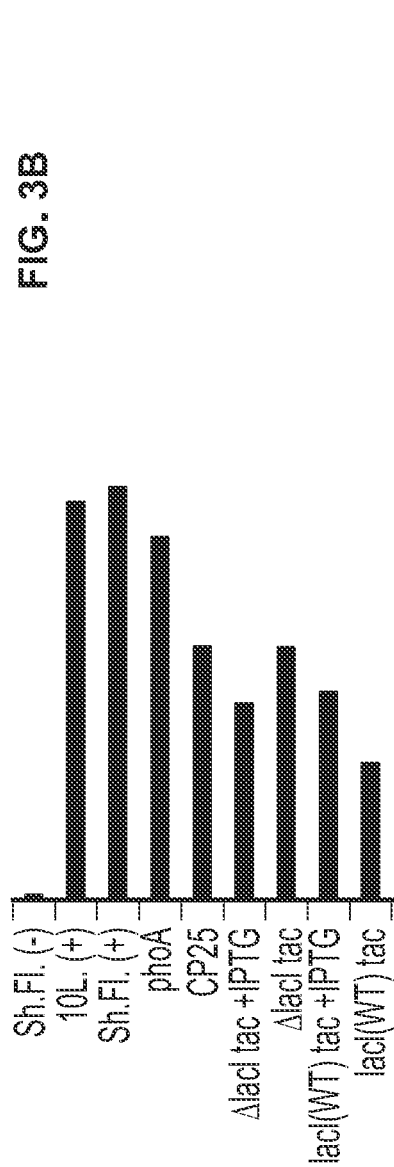
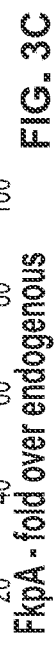
FIG. 3A
FIG. 3B
FIG. 3C

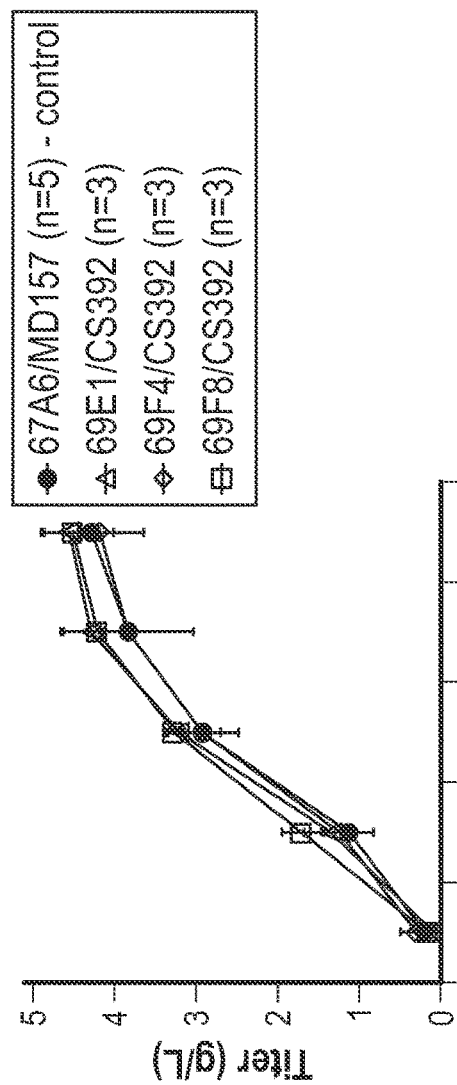
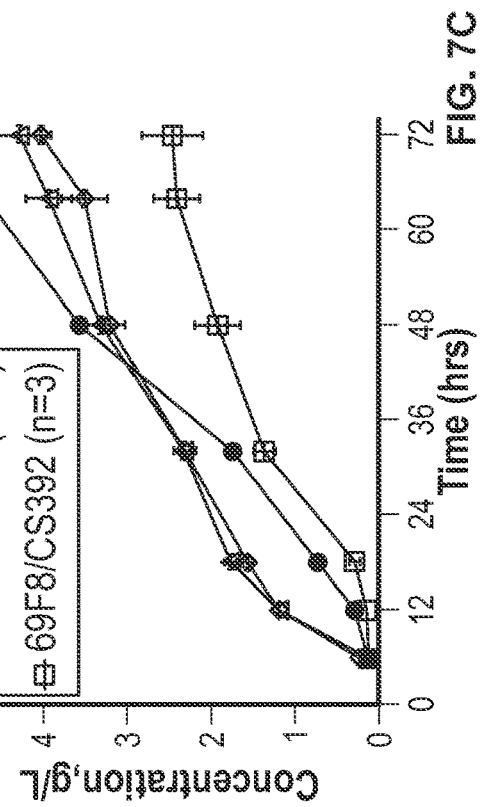
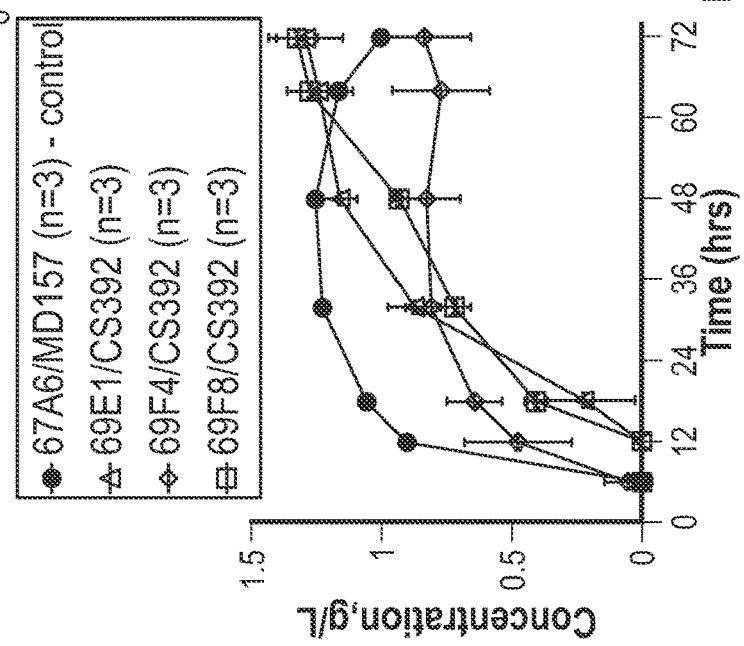
FIG. 7A
FIG. 7B
FIG. 7C

SEQUENCE LISTING

```
<160> NUMBER OF SEQ ID NOS: 10

<210> SEQ ID NO 1
<211> LENGTH: 132
<212> TYPE: PRT
<213> ORGANISM: Artificial Sequence
<220> FEATURE:
<223> OTHER INFORMATION: Synthetic Construct

<400> SEQUENCE: 1

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
            35                  40                  45

Asn Gly Ser Met Val Trp Ser Ile Asn Leu Thr Ala Gly Met Tyr Cys
    50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
        115                 120                 125

Gly Arg Phe Asn
    130
```

<210> SEQ ID NO 2
<211> LENGTH: 114
<212> TYPE: PRT
<213> ORGANISM: Artificial Sequence
<220> FEATURE:
<223> OTHER INFORMATION: Synthetic Construct

<400> SEQUENCE: 2

Ser Pro Gly Pro Val Pro Ser Thr Ala Leu Arg Glu Leu Ile Glu
1               5                   10                  15

Glu Leu Val Asn Ile Thr Gln Asn Gln Lys Ala Pro Leu Cys Asn Gly
            20                  25                  30

Ser Met Val Trp Ser Ile Asn Leu Thr Ala Gly Met Tyr Cys Ala Ala
        35                  40                  45

Leu Glu Ser Leu Ile Asn Val Ser Gly Cys Ser Ala Ile Glu Lys Thr
    50                  55                  60

Gln Arg Met Leu Ser Gly Phe Cys Pro His Lys Val Ser Ala Gly Gln
65                  70                  75                  80

Phe Ser Ser Leu His Val Arg Asp Thr Lys Ile Glu Val Ala Gln Phe
                85                  90                  95

Val Lys Asp Leu Leu Leu His Leu Lys Lys Leu Phe Arg Glu Gly Arg
            100                 105                 110

Phe Asn

<210> SEQ ID NO 3
<211> LENGTH: 118
<212> TYPE: PRT
<213> ORGANISM: Artificial Sequence
<220> FEATURE:
<223> OTHER INFORMATION: Synthetic Construct

<400> SEQUENCE: 3

Glu Val Thr Leu Arg Glu Ser Gly Pro Ala Leu Val Lys Pro Thr Gln
1               5                   10                  15

Thr Leu Thr Leu Thr Cys Thr Val Ser Gly Phe Ser Leu Ser Ala Tyr
            20                  25                  30

Ser Val Asn Trp Ile Arg Gln Pro Pro Gly Lys Ala Leu Glu Trp Leu
        35                  40                  45

Ala Met Ile Trp Gly Asp Gly Lys Ile Val Tyr Asn Ser Ala Leu Lys
    50                  55                  60

Ser Arg Leu Thr Ile Ser Lys Asp Thr Ser Lys Asn Gln Val Val Leu
65                  70                  75                  80

Thr Met Thr Asn Met Asp Pro Val Asp Thr Ala Thr Tyr Tyr Cys Ala
                85                  90                  95

Gly Asp Gly Tyr Tyr Pro Tyr Ala Met Asp Asn Trp Gly Gln Gly Ser
            100                 105                 110

Leu Val Thr Val Ser Ser
        115

<210> SEQ ID NO 4
<211> LENGTH: 112
<212> TYPE: PRT
<213> ORGANISM: Artificial Sequence
<220> FEATURE:
<223> OTHER INFORMATION: Synthetic Construct

<400> SEQUENCE: 4

Asp Ile Val Leu Thr Gln Ser Pro Asp Ser Leu Ser Val Ser Leu Gly

```
            1               5                  10                  15
         Glu Arg Ala Thr Ile Asn Cys Arg Ala Ser Lys Ser Val Asp Ser Tyr
                        20                  25                  30

Gly Asn Ser Phe Met His Trp Tyr Gln Gln Lys Pro Gly Gln Pro Pro
                    35                  40                  45

Lys Leu Leu Ile Tyr Leu Ala Ser Asn Leu Glu Ser Gly Val Pro Asp
             50                  55                  60

Arg Phe Ser Gly Ser Gly Ser Gly Thr Asp Phe Thr Leu Thr Ile Ser
         65                  70                  75                  80

Ser Leu Gln Ala Glu Asp Val Ala Val Tyr Tyr Cys Gln Gln Asn Asn
                         85                  90                  95

Glu Asp Pro Arg Thr Phe Gly Gly Gly Thr Lys Val Glu Ile Lys Arg
                     100                 105                 110

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

Ala Tyr Ser Val Asn
1               5

<210> SEQ ID NO 6
<211> LENGTH: 16
<212> TYPE: PRT
<213> ORGANISM: Artificial Sequence
<220> FEATURE:
<223> OTHER INFORMATION: Synthetic Construct

<400> SEQUENCE: 6

Met Ile Trp Gly Asp Gly Lys Ile Val Tyr Asn Ser Ala Leu Lys Ser
1               5                   10                  15

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

Asp Gly Tyr Tyr Pro Tyr Ala Met Asp Asn
1               5                   10

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Arg Ala Ser Lys Ser Val Asp Ser Tyr Gly Asn Ser Phe Met His
1               5                   10                  15

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct
```

```
<400> SEQUENCE: 9

Leu Ala Ser Asn Leu Glu Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Synthetic Construct

<400> SEQUENCE: 10

Gln Gln Asn Asn Glu Asp Pro Arg Thr
1               5
```

METHODS OF PRODUCING TWO CHAIN PROTEINS IN PROKARYOTIC HOST CELLS

CROSS-REFERENCE TO RELATED APPLICATIONS

This application is a continuation of International Application No. PCT/US2019/059661, filed Nov. 4, 2019, which claims the priority benefit of U.S. Provisional Application No. 62/755,915, filed Nov. 5, 2018, each of which is hereby incorporated by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 14639-2044001SEQLIST.TXT, date recorded: Apr. 29, 2021, size: 6 KB).

FIELD

This disclosure relates to methods of producing recombinant polypeptides, such as antibodies (e.g., bispecific antibodies, half-antibodies, one-armed antibodies, antibody fragments, and the like), as well as prokaryotic host cells that may find use in said methods.

BACKGROUND

Recombinant protein production in prokaryotic host cells has been a source of many important therapeutic agents since the production of human insulin in *E. coli* in 1978. As molecular biology tools and knowledge has advanced, the complexity of recombinant therapeutics has also increased. Production of these recombinant proteins requires that the products exhibit properties such as proper translation, folding, assembly, disulfide bonding, and transport to the periplasm. It is known that expression of many recombinant proteins, particularly those with disulfide bonds (e.g., two chain proteins, including without limitation antibodies and antibody fragments), leads to the formation of inclusion bodies in prokaryotic host cells (Spadiut et al., *Trends in Biotechnology*, 32:54, 2014). Accordingly, there is a demand for expression systems and processes for the recombinant production of properly folded and assembled two chain proteins in prokaryotic host cells on an industrial scale.

Monoclonal antibodies represent one of the fastest growing types of recombinant therapeutic agent, with numerous monoclonal antibodies already approved or under review for the treatment of various diseases (Nelson et al., *Nature Review Drug Discovery*, 9:767, 2010). Traditional monoclonal antibodies bind a single target antigen. For many diseases, it may be advantageous to employ antibodies that bind more than one target antigen, i.e., multispecific antibodies. Such antibodies can be employed in combinatorial approaches directed against multiple therapeutic targets (see, e.g., Bostrom et al., *Science*, 323:1610, 2009; and Wu et al., *Nature Biotechnology*, 25:1290, 2007). For instance, bispecific antibodies can be produced that simultaneously bind an epitope expressed on the surface of a cancer cell and an epitope expressed on a T cell to induce T cell-mediated killing of tumor cells (Shalaby et al., *Clinical Immunology*, 74:185, 1995). Other monoclonal antibody formats have also been used, such as antibody fragments and one-armed antibodies (see, e.g., Merchant et al., *Proc. Natl. Acad. Sci.* 110:E2987-E2996, 2013).

The use of antibodies in the clinic requires the ability to produce two chain proteins in industrially relevant amounts. Vector components that improve recombinant protein production in prokaryotic host cells have been described (see, e.g., Schlapschy et al., *Protein Engineering, Design and Selection*, 19:385, 2006; and Simmons et al., *Journal of Immunological Methods*, 263: 133, 2002), and in particular the expression of chaperone protein(s) has been used to increase antibody titer. However, these chaperone protein(s) are typically expressed from a plasmid in the host cell. This means that for every new recombinant protein to be expressed, considerable time and cost must be spent to construct unique expression plasmids encoding both the recombinant product and the chaperone(s) and tune their expression (e.g., by testing different promoters and/or translation initiation regions). This also necessitates the use of larger plasmid sizes in order to accommodate the coding sequence(s) and associated regulatory elements for the chaperone protein(s). Plasmid expression also typically leads to higher expression levels for the chaperone protein(s) (as plasmids can be present in at least 10-15 copies per cell), and in some cases this necessitates additional purification step(s) in order to remove chaperone protein from the recombinant product titer.

All references cited herein, including patent applications, patent publications, and UniProtKB/Swiss-Prot Accession numbers are herein incorporated by reference in their entirety, as if each individual reference were specifically and individually indicated to be incorporated by reference.

SUMMARY

There remains a need for optimal methods for efficiently producing recombinant two chain proteins on a preparative scale. In particular, the integration into the prokaryotic host cell chromosome of translational unit(s) encoding chaperone proteins, and/or the integration of non-native promoters to drive expression of native chaperone proteins, would allow for a single host cell that could be used to express a variety of recombinant protein products and simplify the plasmid engineering and protein purification protocols required for production.

To meet these and other demands, provided herein are prokaryotic host cells and methods of using the same in order to produce two-chain polypeptides. Advantageously, these host cells and methods allow for more efficient production of two-chain polypeptides, e.g., without requiring up-front time and cost to optimize chaperone expression plasmids or downstream purification steps to remove chaperone proteins.

In one aspect, provided herein are methods of producing a polypeptide comprising two chains in a prokaryotic host cell comprising a host cell chromosome, the methods comprising: (a) culturing the host cell to express the two chains of the polypeptide in a culture medium under conditions suitable for expression of the two chains of the polypeptide, whereby upon expression the two chains fold and assemble to form a biologically active polypeptide in the host cell; wherein the host cell comprises: (1) a first polynucleotide comprising a first translational unit encoding a first chain of the polypeptide; (2) a second polynucleotide comprising a second translational unit encoding a second chain of the polypeptide, wherein the first and second polynucleotides are part of one or more extra-chromosomal polynucleotides;

and (3) a third polynucleotide comprising a third translational unit encoding a chaperone protein selected from the group consisting of peptidyl-prolyl isomerases and protein disulfide oxidoreductases, wherein the third translational unit is part of the host cell chromosome, wherein the third translational unit is in operable combination with a promoter that is integrated in the host cell chromosome and drives transcription of the third translational unit, and wherein the combination of the third translational unit and the promoter is non-native to the host cell chromosome; and (b) recovering the biologically active polypeptide from the host cell.

In some embodiments, the promoter is an inducible promoter. In some embodiments, the inducible promoter is a Pho promoter that drives transcription of the third translational unit when phosphate in the culture medium has been depleted. In some embodiments, the inducible promoter is an isopropyl beta-D-thiogalactoside (IPTG)-inducible promoter that drives transcription of the third translational unit when IPTG is present in the culture medium. In some embodiments, the promoter is a constitutive promoter. In some embodiments, the constitutive promoter is a CP25 promoter. In some embodiments, the third translational unit is native to the host cell chromosome. In some embodiments, the third translational unit is non-native to the host cell chromosome. In some embodiments, the chaperone protein is a peptidyl-prolyl isomerase. In some embodiments, the peptidyl-prolyl isomerase is an FkpA protein. In some embodiments, the FkpA is *E. coli* FkpA. In some embodiments, the chaperone protein is a protein disulfide oxidoreductase. In some embodiments, the protein disulfide oxidoreductase is a DsbC protein. In some embodiments, the protein disulfide oxidoreductase is *E. coli* DsbC. In some embodiments, the protein disulfide oxidoreductase is a DsbA protein. In some embodiments, the protein disulfide oxidoreductase is *E. coli* DsbA.

In another aspect, provided herein are methods of producing a polypeptide comprising two chains in a prokaryotic host cell comprising a host cell chromosome, the methods comprising: (a) culturing the host cell to express the two chains of the polypeptide in a culture medium under conditions suitable for expression of the two chains of the polypeptide, whereby upon expression the two chains fold and assemble to form a biologically active polypeptide in the host cell; wherein the host cell comprises: (1) a first polynucleotide comprising a first translational unit encoding a first chain of the polypeptide; (2) a second polynucleotide comprising a second translational unit encoding a second chain of the polypeptide, wherein the first and second polynucleotides are part of one or more extra-chromosomal polynucleotides; (3) a third polynucleotide comprising a third translational unit encoding a protein disulfide oxidoreductase, wherein the third translational unit is part of the host cell chromosome, wherein the third translational unit is in operable combination with a first promoter that is integrated in the host cell chromosome and drives transcription of the third translational unit, wherein the combination of the third translational unit and the first promoter is non-native to the host cell chromosome; and (4) a fourth polynucleotide comprising a fourth translational unit encoding a peptidyl-prolyl isomerase, wherein the fourth translational unit is part of the host cell chromosome, wherein the fourth translational unit is in operable combination with a second promoter that is integrated in the host cell chromosome and drives transcription of the fourth translational unit, wherein the combination of the fourth translational unit and the second promoter is non-native to the host cell chromosome; and (b) recovering the biologically active polypeptide from the host cell.

In some embodiments, the first and second promoters are both inducible promoters. In some embodiments, the first and second promoters are both Pho promoters that drive transcription of the third and fourth translational units, respectively, when phosphate in the culture medium has been depleted. In some embodiments, one of the first and second promoters is an inducible promoter, and the other of the first and second promoters is a constitutive promoter. In some embodiments, the first promoter is a Pho promoter that drives transcription of the third translational unit when phosphate in the culture medium has been depleted, and the second promoter is a CP25 promoter. In some embodiments, the second promoter is an inducible promoter, and the first promoter is a constitutive promoter. In some embodiments, one or both of the third translational unit and fourth translational unit are native to the host cell chromosome. In some embodiments, the third translational unit and the fourth translational unit are both native to the host cell chromosome. In some embodiments, one or both of the third translational unit and fourth translational unit are non-native to the host cell chromosome. In some embodiments, the protein disulfide oxidoreductase is a DsbC protein. In some embodiments, the protein disulfide oxidoreductase is *E. coli* DsbC. In some embodiments, the peptidyl-prolyl isomerase is an FkpA protein. In some embodiments, the FkpA is *E. coli* FkpA. In some embodiments, the protein disulfide oxidoreductase is *E. coli* DsbC, wherein the first promoter is a Pho promoter that drives transcription of the third translational unit when phosphate in the culture medium has been depleted, wherein the peptidyl-prolyl isomerase is *E. coli* FkpA, and wherein the second promoter is a CP25 promoter. In some embodiments, the protein disulfide oxidoreductase is *E. coli* DsbC, wherein the first promoter is a Pho promoter that drives transcription of the third translational unit when phosphate in the culture medium has been depleted, wherein the peptidyl-prolyl isomerase is *E. coli* FkpA, and wherein the second promoter is a Pho promoter that drives transcription of the fourth translational unit when phosphate in the culture medium has been depleted. In some embodiments, the host cell further comprises: (5) a fifth polynucleotide comprising a fifth translational unit encoding a second protein disulfide oxidoreductase, wherein the fifth translational unit is part of the host cell chromosome, wherein the fifth translational unit is in operable combination with a third promoter that is integrated in the host cell chromosome and drives transcription of the fifth translational unit, wherein the combination of the fifth translational unit and the third promoter is non-native to the host cell chromosome. In some embodiments, the second protein disulfide oxidoreductase is a DsbA protein. In some embodiments, the second protein disulfide oxidoreductase is *E. coli* DsbA. In some embodiments, the third promoter is an inducible promoter. In some embodiments, the third promoter is an isopropyl beta-D-thiogalactoside (IPTG)-inducible promoter that drives transcription of the fifth translational unit when IPTG is present in the culture medium. In some embodiments, the fifth translational unit is native to the host cell chromosome. In some embodiments, the fifth translational unit is non-native to the host cell chromosome. In some embodiments, the first protein disulfide oxidoreductase is *E. coli* DsbC, wherein the first promoter is an isopropyl beta-D-thiogalactoside (IPTG)-inducible promoter that drives transcription of the third translational unit when IPTG is present in the culture medium, wherein the peptidyl-prolyl isomerase is *E. coli*

FkpA, wherein the second promoter is a CP25 promoter, wherein the second protein disulfide oxidoreductase is *E. coli* DsbA, wherein the third promoter is an isopropyl beta-D-thiogalactoside (IPTG)-inducible promoter that drives transcription of the fifth translational unit when IPTG is present in the culture medium. In some embodiments, the host cell further comprises: (6) a sixth polynucleotide comprising a sixth translational unit encoding a third chain of the polypeptide, wherein the sixth polynucleotide is part of the one or more extra-chromosomal polynucleotides; whereby upon expression the three chains fold and assemble to form a biologically active polypeptide in the host cell. In some embodiments, the first translational unit encodes an immunoglobulin heavy chain, wherein the second translational unit encodes an immunoglobulin light chain, wherein the sixth translational unit encodes an immunoglobulin Fc fragment, and wherein the three chains fold and assemble to form a biologically active monovalent antibody. In some embodiments, the monovalent antibody is capable of specifically binding an antigen.

In some embodiments of any of the above embodiments, the first and second polynucleotides are both part of a single extra-chromosomal expression vector. In some embodiments, the extra-chromosomal expression vector further comprises a polynucleotide encoding a selectable marker that promotes resistance to a selection agent, wherein the host cell is cultured under conditions suitable for expression of the selectable marker, and wherein the culture medium further comprises the selection agent. In some embodiments, the extra-chromosomal expression vector further comprises an origin of replication suitable for replicating the extra-chromosomal expression vector in the prokaryotic host cell. In some embodiments, the two chains of the polypeptide are linked to each other by at least one disulfide bond. In some embodiments, the polypeptide is a monomer of a heterodimer. In some embodiments, the polypeptide is a half antibody in which the first chain and the second chain comprise an immunoglobulin heavy chain and an immunoglobulin light chain. In some embodiments, the half antibody is capable of specifically binding an antigen. In some embodiments, the polypeptide is a secretory protein. In some embodiments, the secretory protein is recovered from the periplasm of the host cell. In some embodiments, the prokaryotic host cell is a gram-negative bacterium. In some embodiments, the gram-negative bacterium is *E. coli*. In some embodiments, the *E. coli* is of a strain deficient in endogenous protease activity. In some embodiments, the *E. coli* is a strain with a degpS210A mutation. In some embodiments, the *E. coli* is of a strain with enhanced LacI production or activity. In some embodiments, the *E. coli* is a strain with a lacI$^Q$ mutation. In some embodiments, the *E. coli* is of the strain ΔfhuA ΔphoA iivG2096 (IlvG+; Valr) Δprc spr43H1 ΔmanA lacI$^Q$ ΔompT ΔmenE742 degPS210A.

In another aspect, provided herein are methods of producing a bispecific antibody comprising a first half antibody capable of binding a first antigen and a second half antibody capable of binding a second antigen, the methods comprising: producing the first half antibody according to the method of any one of the above embodiments, wherein the first translational unit encodes the heavy chain of the first half antibody and the second translational unit encodes the light chain of the first half antibody, and wherein the first half antibody comprises at least one knob-forming mutation; producing the second half antibody according to the method of any one of the above embodiments, wherein the first translational unit encodes the heavy chain of the second half antibody and the second translational unit encodes the light chain of the second half antibody, and wherein the second half antibody comprises at least one hole-forming mutation; and combining, in a reducing condition, the first half antibody with the second half antibody to produce the bispecific antibody.

In some embodiments, the first antigen and the second antigen are different antigens. In some embodiments, the methods further comprise the step of adding a reducing agent to achieve the reducing condition. In some embodiments, the reducing agent is glutathione.

In another aspect, provided herein are host cells (e.g., prokaryotic host cells) comprising a host cell chromosome, wherein the prokaryotic host cells comprise: (1) a first polynucleotide comprising a first translational unit encoding a peptidyl-prolyl isomerase, wherein the first translational unit is part of the host cell chromosome, wherein the first translational unit is in operable combination with a first promoter that is integrated in the host cell chromosome and drives transcription of the first translational unit, wherein the combination of the first translational unit and the first promoter is non-native to the host cell chromosome; and (2) a second polynucleotide comprising a second translational unit encoding a protein disulfide oxidoreductase, wherein the second translational unit is part of the host cell chromosome, wherein the second translational unit is in operable combination with a second promoter that is integrated in the host cell chromosome and drives transcription of the second translational unit, wherein the combination of the second translational unit and the second promoter is non-native to the host cell chromosome.

In some embodiments, one or both of the first translational unit and the second translational unit are native to the prokaryotic host cell chromosome. In some embodiments, the first translational unit and the second translational unit are both native to the prokaryotic host cell chromosome. In some embodiments, one or both of the first translational unit and the second translational unit are non-native to the prokaryotic host cell chromosome. In some embodiments, the first promoter is a first inducible promoter. In some embodiments, the first inducible promoter is a Pho promoter. In some embodiments, the first inducible promoter is an isopropyl beta-D-thiogalactoside (IPTG)-inducible promoter. In some embodiments, the first promoter is a first constitutive promoter. In some embodiments, the first constitutive promoter is a CP25 promoter. In some embodiments, the second promoter is a second inducible promoter. In some embodiments, the second inducible promoter is a Pho promoter. In some embodiments, the second inducible promoter is an isopropyl beta-D-thiogalactoside (IPTG)-inducible promoter. In some embodiments, the second promoter is a second constitutive promoter. In some embodiments, the second constitutive promoter is a CP25 promoter. In some embodiments, the peptidyl-prolyl isomerase is an FkpA protein. In some embodiments, the FkpA is *E. coli* FkpA. In some embodiments, the protein disulfide oxidoreductase is a DsbC protein. In some embodiments, the protein disulfide oxidoreductase is *E. coli* DsbC. In some embodiments, the peptidyl-prolyl isomerase is an FkpA protein, wherein the first promoter is a CP25 promoter, wherein the protein disulfide oxidoreductase is a DsbC protein, and wherein the second promoter is a Pho promoter. In some embodiments, the peptidyl-prolyl isomerase is an FkpA protein, wherein the first promoter is a Pho promoter, wherein the protein disulfide oxidoreductase is a DsbC protein, and wherein the second promoter is a Pho promoter. In some embodiments, the host cells further comprise: (3) a third polynucleotide comprising a third translational unit encoding a second protein disulfide oxidoreductase, wherein the third translational unit is part of the host cell chromosome, wherein the third translational unit is in operable combination with a third promoter that is integrated in the host cell chromosome and drives transcription of the third translational unit, wherein the combination of the third translational unit and the third promoter is non-native to the host cell chromosome. In some embodiments, the second protein disulfide oxidoreductase is a DsbA protein. In some embodiments, the second protein disulfide oxidoreductase is E. coli DsbA. In some embodiments, the third promoter is a third inducible promoter. In some embodiments, the third inducible promoter is an isopropyl beta-D-thiogalactoside (IPTG)-inducible promoter. In some embodiments, the peptidyl-prolyl isomerase is an FkpA protein, wherein the first promoter is a CP25 promoter, wherein the first protein disulfide oxidoreductase is a DsbC protein, wherein the second promoter is an isopropyl beta-D-thiogalactoside (IPTG)-inducible promoter, wherein the second protein disulfide oxidoreductase is a DsbA protein, and wherein the third promoter is an isopropyl beta-D-thiogalactoside (IPTG)-inducible promoter. In some embodiments, the prokaryotic host cell is a gram-negative bacterium. In some embodiments, the gram-negative bacterium is E. coli. In some embodiments, the E. coli is of a strain deficient in endogenous protease activity. In some embodiments, the E. coli is a strain with a degpS210A mutation. In some embodiments, the E. coli is of a strain with enhanced LacI production or activity. In some embodiments, the E. coli is a strain with a lacI$^Q$ mutation. In some embodiments, the E. coli is of the strain ΔfhuA ΔphoA iivG2096 (IlvG+; Valr) Δprc spr43H1 ΔmanA lacI$^Q$ ΔompT ΔmenE742 degPS210A.

In some embodiments, the host cells further comprise an extra-chromosomal expression vector that comprises: (a) a first extra-chromosomal polynucleotide comprising a first extra-chromosomal translational unit encoding a first chain of a two-chain polypeptide; and (b) a second extra-chromosomal polynucleotide comprising a second extra-chromosomal translational unit encoding a second chain of the two-chain polypeptide; whereby upon expression the two chains fold and assemble to form a biologically active two-chain polypeptide in the host cell. In some embodiments, the extra-chromosomal expression vector further comprises an origin of replication suitable for replicating the extra-chromosomal expression vector in the prokaryotic host cell. In some embodiments, the extra-chromosomal expression vector further comprises a polynucleotide encoding a selectable marker that promotes resistance to a selection agent. In some embodiments, the two chains of the two-chain polypeptide are linked to each other by at least one disulfide bond. In some embodiments, the two-chain polypeptide is a monomer of a heterodimer. In some embodiments, the polypeptide is a half antibody in which the first chain and the second chain comprise an immunoglobulin heavy chain and an immunoglobulin light chain. In some embodiments, the half antibody is capable of specifically binding an antigen. In some embodiments, the two-chain polypeptide is a secretory protein. In some embodiments, the secretory protein is recovered from the periplasm of the host cell. In some embodiments, the extra-chromosomal expression vector further comprises a third extra-chromosomal polynucleotide comprising a third extra-chromosomal translational unit encoding a third chain of a two-chain polypeptide, whereby upon expression the three chains fold and assemble to form a biologically active polypeptide in the host cell. In some embodiments, the first extra-chromosomal translational unit encodes an immunoglobulin heavy chain, wherein the second extra-chromosomal translational unit encodes an immunoglobulin light chain, wherein the third extra-chromosomal translational unit encodes an immunoglobulin Fc fragment, and wherein the three chains fold and assemble to form a biologically active monovalent antibody. In some embodiments, the monovalent antibody is capable of specifically binding an antigen.

It is to be understood that one, some, or all of the properties of the various embodiments described herein may be combined to form other embodiments of the present disclosure. These and other aspects of the disclosure will become apparent to one of skill in the art. These and other embodiments of the disclosure are further described by the detailed description that follows.

BRIEF DESCRIPTION OF THE DRAWINGS

FIGS. 3A-3C show the relative chaperone expression levels (fold, over native expression levels) of DsbA (FIG. 3A), DsbC (FIG. 3B), or FkpA (FIG. 3C) in the indicated strains in shake flasks. Sh.Fl. represents shake flask culture, + represents positive control (plasmid chaperone expression), – represents negative control (no chaperone expression), and Sh. Fl. (–) refers to native expression level.

FIG. 6A) and osmolality (FIG. 6B) over time of cultures of the indicated strain/plasmid combinations producing xIL13.

FIGS. 7A-7C show the xIL13 titer (g/L; FIG. 7A), DsbC concentration (FIG. 7B), and FkpA concentration (FIG. 7C) produced by the indicated strains over time.

FIG. 8A) and osmolality (FIG. 8B) over time of cultures of the indicated strain/plasmid combinations producing AF2.

FIG. 10A) and osmolality (FIG. 10B) over time of cultures of the indicated strain/plasmid combinations producing MetMAb.

FIG. 12A) and osmolality (FIG. 12B) over time of cultures of the indicated strain/plasmid combinations producing anti-VEGF antibody fragment.

DETAILED DESCRIPTION

Figure 1:
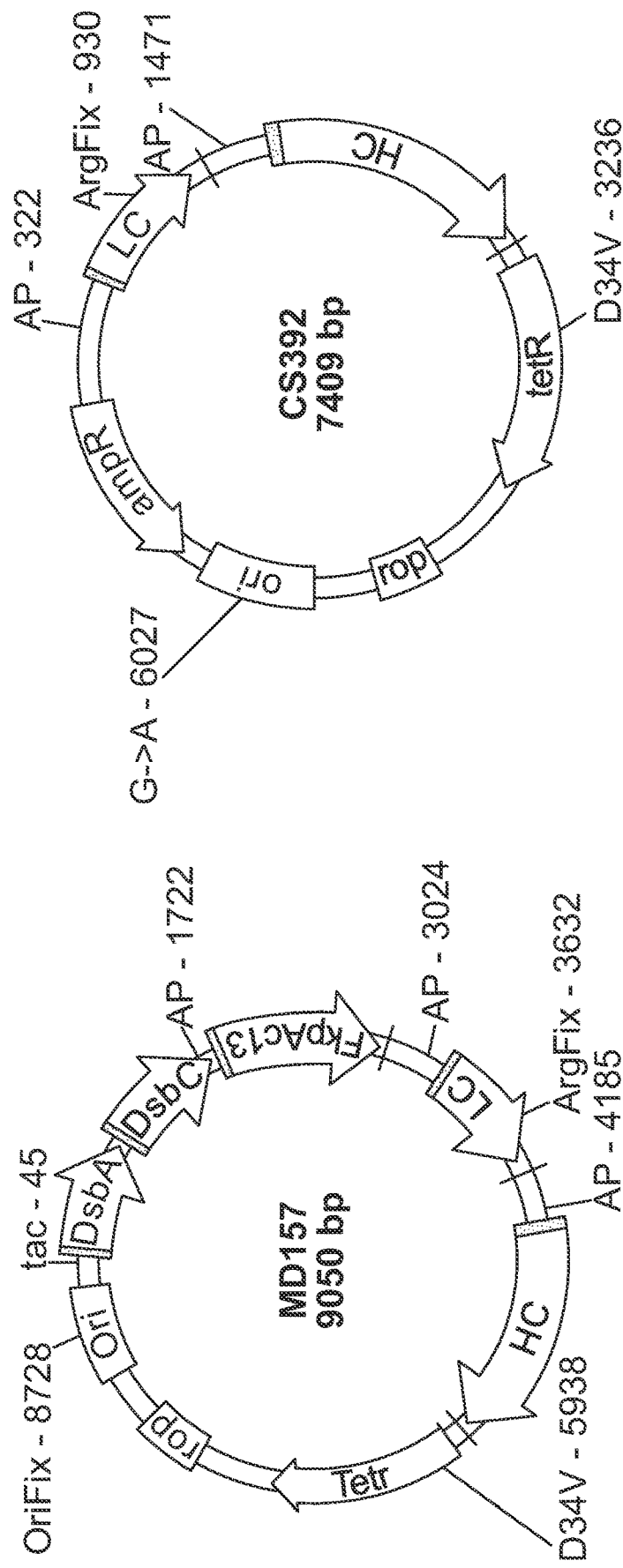
FIG. 1 shows plasmid maps of an expression vector (MD156; left) used to overexpress chaperone proteins and a two-chain protein product (in this case, antibody or antibody fragment heavy and light chains; "HC" and "LC," respectively), as compared to an expression vector (CS392; right) for expression of the two-chain protein product in a host cell with chromosomal overexpression of the same chaperone proteins. Vector sizes are provided in base pairs, bp.

The present disclosure provides host cells (e.g., prokaryotic host cells) with integrated non-native promoter:chaperone protein combination(s) suitable for large-scale production of recombinant two-chain protein products, as well as methods related thereto. The examples provided herein demonstrate that prokaryotic host cells expressing chaperone proteins from the host cell chromosome yield comparable titers to plasmid-based chaperone expression. These results were consistent across multiple antibody formats, such as half-antibodies, one-armed antibodies, and antibody fragments, and required little to no additional process development. Importantly, the data presented herein show that chaperone expression from the host cell chromosome rather than a plasmid results in lower chaperone expression levels (potentially obviating the need for further downstream purification to remove chaperone proteins from the product) but equivalent or higher product titers. These results demonstrate that the products can be produced at an industrial scale at least as efficiently using the host cells and/or methods of the present disclosure, as compared to using host cells that express the chaperone protein(s) from a plasmid, without requiring up-front time and cost to optimize chaperone expression plasmids or downstream purification steps to remove chaperone proteins.

In one aspect, provided herein are methods of producing a polypeptide comprising two chains in a prokaryotic host cell comprising a host cell chromosome, the methods comprising: culturing the host cell to express the two chains of the polypeptide in a culture medium under conditions suitable for expression of the two chains of the polypeptide, whereby upon expression the two chains fold and assemble to form a biologically active polypeptide in the host cell; and (b) recovering the biologically active polypeptide from the host cell; wherein the host cell comprises: (1) a first polynucleotide comprising a first translational unit encoding a first chain of the polypeptide; (2) a second polynucleotide comprising a second translational unit encoding a second chain of the polypeptide, wherein the first and second polynucleotides are part of one or more extra-chromosomal polynucleotides; and (3) a third polynucleotide comprising a third translational unit encoding a chaperone protein selected from the group consisting of peptidyl-prolyl isomerases and protein disulfide oxidoreductases, wherein the third translational unit is part of the host cell chromosome, wherein the third translational unit is in operable combination with a promoter that is integrated in the host cell chromosome and drives transcription of the third translational unit, wherein the combination of the third translational unit and the promoter is non-native to the host cell chromosome.

In another aspect, provided herein are methods of producing a polypeptide comprising two chains in a prokaryotic host cell comprising a host cell chromosome, the methods comprising: culturing the host cell to express the two chains of the polypeptide in a culture medium under conditions suitable for expression of the two chains of the polypeptide, whereby upon expression the two chains fold and assemble to form a biologically active polypeptide in the host cell; and (b) recovering the biologically active polypeptide from the host cell; wherein the host cell comprises: (1) a first polynucleotide comprising a first translational unit encoding a first chain of the polypeptide; (2) a second polynucleotide comprising a second translational unit encoding a second chain of the polypeptide, wherein the first and second polynucleotides are part of one or more extra-chromosomal polynucleotides; (3) a third polynucleotide comprising a third translational unit encoding a protein disulfide oxidoreductase, wherein the third translational unit is part of the host cell chromosome, wherein the third translational unit is in operable combination with a first promoter that is integrated in the host cell chromosome and drives transcription of the third translational unit, wherein the combination of the third translational unit and the first promoter is non-native to the host cell chromosome; and (4) a fourth polynucleotide comprising a fourth translational unit encoding a peptidyl-prolyl isomerase, wherein the fourth translational unit is part of the host cell chromosome, wherein the fourth translational unit is in operable combination with a second promoter that is integrated in the host cell chromosome and drives transcription of the fourth translational unit, wherein the combination of the fourth translational unit and the second promoter is non-native to the host cell chromosome.

In another aspect, provided herein are prokaryotic host cells comprising a host cell chromosome, wherein the prokaryotic host cells comprise: (1) a first polynucleotide comprising a first translational unit encoding a peptidyl-prolyl isomerase, wherein the first translational unit is part of the host cell chromosome, wherein the first translational unit is in operable combination with a first promoter that is integrated in the host cell chromosome and drives transcription of the first translational unit, wherein the combination of the first translational unit and the first promoter is non-native to the host cell chromosome; and (2) a second polynucleotide comprising a second translational unit encoding a protein disulfide oxidoreductase, wherein the second translational unit is part of the host cell chromosome, wherein the second translational unit is in operable combination with a second promoter that is integrated in the host cell chromosome and drives transcription of the second translational unit, wherein the combination of the second translational unit and the second promoter is non-native to the host cell chromosome.

I. Definitions

Before describing the disclosure in detail, it is to be understood that this disclosure is not limited to particular compositions or biological systems, which can, of course, vary. It is also to be understood that the terminology used herein is for the purpose of describing particular embodiments only, and is not intended to be limiting.

As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se. At a maximum, the term "about" as used herein in reference to a value, encompasses from 90% to 110% of that value (e.g., relative translation strength of a first and second TIR of about 1.0 to about 3.0 refers to a relative translation strength in the range of between 0.9 and 3.3).

It is understood that aspects and embodiments of the disclosure described herein include "comprising," "consisting," and "consisting essentially of" aspects and embodiments.

The term "polypeptide comprising two chains," (the terms "two chain protein" and "two chain polypeptide" may also be used interchangeably herein), as used herein is intended to refer to any polypeptide containing more than one distinct polypeptide chain. In some embodiments, a two chain protein may include a macromolecular complex of two or more polypeptides linked together through one or more intermolecular linkages, including without limitation a disulfide bond. In some embodiments, a two chain protein may include a single polypeptide with amino acid sequences belonging to two distinct polypeptide chains (e.g., an antibody heavy chain and an antibody light chain) linked by a polypeptide linker. In this case, a two chain protein may physically represent a single chain, but two or more portions of the single chain may functionally behave as if they are two separate protein chains. For example, a single chain antibody may include a functional heavy chain and a functional light chain that, while joined by a polypeptide linker, nonetheless fold and assemble as if they were separate polypeptides associated only by intermolecular linkages (e.g., one or more disulfide bonds).

The terms "native" and "non-native," as used herein in reference to one or more genetic elements (e.g., a promoter, translational unit, or combination thereof), are intended to refer to the genomic context of the genetic element in a host cell chromosome as it occurs in nature. For example, a translational unit is "native" with regard to a host cell or host cell chromosome when the translational unit naturally occurs in the genome of the host cell, and is "non-native" when the translational unit does not naturally occur in the genome of the host cell. A promoter is "native" with regard to a host cell or host cell chromosome when the promoter naturally occurs in the genome of the host cell, and is "non-native" when the promoter does not naturally occur in the genome of the host cell. The operable combination of a promoter with a translational unit is "non-native" when the promoter does not naturally occur in the genome of the host cell in the same operable linkage with the translational unit, or vice versa. For example, a promoter:translational unit combination is "non-native" with respect to a host cell or host cell chromosome when one or both of the promoter and the translational unit is/are not naturally present in the host cell genome, when the promoter is present in the host cell genome in operable linkage with a translational unit with which it is not operably combined in the naturally-occurring host cell genome (even if the same promoter sequence is naturally present elsewhere in the host cell genome), or when the translational unit is present in the host cell genome in operable linkage with a promoter with which it is not operably combined in the naturally-occurring host cell genome (even if the same translational unit sequence is naturally present elsewhere in the host cell genome).

The term "vector," as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" (or simply, "recombinant vectors"). In general, expression vectors of utility in recombinant DNA techniques are often in the form of plasmids. In the present specification, "plasmid" and "vector" may be used interchangeably as the plasmid is the most commonly used form of vector.

The term "cistron," as used herein, is intended to refer to a genetic element broadly equivalent to a translational unit comprising the nucleotide sequence coding for a polypeptide chain and adjacent control regions. A "cistron" may include, for example, one or more open-reading frames, a translational initiation region (TIR; as defined herein below), a signal sequence and a termination region.

A "polycistronic" expression vector refers to a single vector that contains and expresses multiple cistrons under the regulatory control of one single promoter. A common example of polycistronic vector is a "dicistronic" vector that contains and expresses two different polypeptides under the control of one promoter. Upon expression of a dicistronic or polycistronic vector, multiple genes are first transcribed as a single transcriptional unit, and then translated separately.

A "transcriptional unit" refers to a polynucleotide that is transcribed as a single RNA transcript. A "translational unit" refers to a polynucleotide that encodes and, when translated, produces a polypeptide. As described above, a polycistronic polynucleotide may contain a single transcriptional unit with multiple translational units.

A "separate cistron" expression vector according to the present disclosure refers to a single vector comprising at least two separate promoter-cistron pairs, wherein each cistron is under the control of its own promoter. Upon expression of a separate cistron expression vector, both transcription and translation processes of different genes are separate and independent.

A "chaperone protein" as used herein refers to any protein that aids in the folding or assembly of other macromolecules, including without limitation two chain proteins. Generally, chaperone proteins may act by many different mechanisms to promote protein folding or assembly. For example, chaperone proteins may promote protein folding and/or assembly, catalyze the formation of intrachain disulfide bonds, promote protein un-folding and/or disassembly (e.g., of aggregated or misfolded proteins or multiprotein complexes), prevent aggregation, aid in protein degradation, and so forth.

"Secretion signal sequence" or "signal sequence" refers to a nucleic acid sequence encoding for a short signal peptide that can be used to direct a newly synthesized protein of interest through a cellular membrane, usually the inner membrane or both inner and outer membranes of prokaryotes. As such, the protein of interest such as the immunoglobulin light or heavy chain polypeptide is secreted into the periplasm of the prokaryotic host cells or into the culture medium. The signal peptide encoded by the secretion signal sequence may be endogenous to the host cells, or they may be non-endogenous, including signal peptides native to the polypeptide to be expressed. Secretion signal sequences are typically present at the amino terminus of a polypeptide to be expressed, and are typically removed enzymatically between biosynthesis and secretion of the polypeptide from the cytoplasm. Thus, the signal peptide is usually not present in a mature protein product.

"Operably linked" refers to a juxtaposition of two or more components, wherein the components so described are in a relationship permitting them to function in their intended manner. For example, a promoter is operably linked to a coding sequence or translational unit if it acts in cis to control or modulate the transcription of the linked sequence. Generally, but not necessarily, the DNA sequences that are "operably linked" are contiguous and, where necessary to join two protein coding regions or in the case of a secretory leader, contiguous and in the reading frame. However, although an operably linked promoter is generally located upstream of the coding sequence or translational unit, it is not necessarily contiguous with it. Operably linked enhancers can be located upstream, within or downstream of coding sequences/translational units and at considerable distances from the promoter. Linking is accomplished by recombinant methods known in the art, e.g., using PCR methodology, by annealing, or by ligation at convenient restriction sites. If convenient restriction sites do not exist, then synthetic oligonucleotide adaptors or linkers are used in accord with conventional practice.

"Regulatory elements" as used herein, refer to nucleotide sequences present in cis, necessary for transcription and translation of a polynucleotide encoding a heterologous polypeptide into polypeptides. The transcriptional regulatory elements normally comprise a promoter 5' of the gene sequence to be expressed, transcriptional initiation and termination sites, and polyadenylation signal sequence. The term "transcriptional initiation site" refers to the nucleic acid in the construct corresponding to the first nucleic acid incorporated into the primary transcript, i.e., the mRNA precursor; the transcriptional initiation site may overlap with the promoter sequences.

A "promoter" refers to a polynucleotide sequence that controls transcription of a gene or sequence to which it is operably linked. A promoter includes signals for RNA polymerase binding and transcription initiation. The promoters used will be functional in the cell type of the host cell in which expression of the selected sequence is contemplated. A large number of promoters including constitutive, inducible and repressible promoters from a variety of different sources, are well known in the art (and identified in databases such as GenBank) and are available as or within cloned polynucleotides (from, e.g., depositories such as ATCC as well as other commercial or individual sources). With inducible promoters, the activity of the promoter increases or decreases in response to a signal, e.g., the presence of IPTG or phosphate depletion.

The term "host cell" (or "recombinant host cell"), as used herein, is intended to refer to a cell that has been genetically altered, or is capable of being genetically altered by introduction of an exogenous or non-native polynucleotide, such as a recombinant plasmid or vector. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "pharmaceutical formulation" refers to a preparation which is in such form as to permit the biological activity of the active ingredient to be effective, and which contains no additional components which are unacceptably toxic to a subject to which the formulation would be administered. Such formulations are sterile. "Pharmaceutically acceptable" excipients (vehicles, additives) are those which can reasonably be administered to a subject mammal to provide an effective dose of the active ingredient employed.

A "subject" or an "individual" for purposes of treatment refers to any animal classified as a mammal, including humans, domestic and farm animals, and zoo, sports, or pet animals, such as dogs, horses, cats, cows, etc. Preferably, the mammal is human.

The term "antibody" herein is used in the broadest sense and specifically covers monoclonal antibodies (including full length monoclonal antibodies), polyclonal antibodies, multispecific antibodies (e.g., bispecific antibodies), and antibody fragments so long as they exhibit the desired biological activity.

An "isolated" antibody is one which has been identified and separated and/or recovered from a component of its natural environment. Contaminant components of its natural environment are materials which would interfere with research, diagnostic or therapeutic uses for the antibody, and may include enzymes, hormones, and other proteinaceous or nonproteinaceous solutes. In some embodiments, an antibody is purified (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of, for example, a spinning cup sequenator, or (3) to homogeneity by SDS-PAGE under reducing or nonreducing conditions using, for example, Coomassie blue or silver stain. Isolated antibody includes the antibody in situ within recombinant cells since at least one component of the antibody's natural environment will not be present. Ordinarily, however, isolated antibody will be prepared by at least one purification step.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

The term "constant domain" refers to the portion of an immunoglobulin molecule having a more conserved amino acid sequence relative to the other portion of the immunoglobulin, the variable domain, which contains the antigen binding site. The constant domain contains the $C_H1$, $C_H2$ and $C_H3$ domains (collectively, CH) of the heavy chain and the CHL (or CL) domain of the light chain.

The "variable region" or "variable domain" of an antibody refers to the amino-terminal domains of the heavy or light chain of the antibody. The variable domain of the heavy chain may be referred to as "$V_H$." The variable domain of the light chain may be referred to as "$V_L$." These domains are generally the most variable parts of an antibody and contain the antigen-binding sites.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions (HVRs) both in the light-chain and the heavy-chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen-binding site of antibodies (see Kabat et al., *Sequences of Proteins of Immunological Interest*, Fifth Edition, National Institute of Health, Bethesda, Md. (1991)). The constant domains are not involved directly in the binding of an antibody to an antigen, but exhibit various effector functions, such as participation of the antibody in antibody-dependent cellular toxicity.

The "light chains" of antibodies (immunoglobulins) from any mammalian species can be assigned to one of two clearly distinct types, called kappa ("κ") and lambda ("λ"), based on the amino acid sequences of their constant domains.

The term IgG "isotype" or "subclass" as used herein is meant any of the subclasses of immunoglobulins defined by the chemical and antigenic characteristics of their constant regions.

Depending on the amino acid sequences of the constant domains of their heavy chains, antibodies (immunoglobulins) can be assigned to different classes. There are five major classes of immunoglobulins: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, γ, ε, γ, and μ, respectively. The subunit structures and three-dimensional configurations of different classes of immunoglobulins are well known and described generally in, for example, Abbas et al. *Cellular and Mol. Immunology*, 4th ed. (W.B. Saunders, Co., 2000). An antibody may be part of a larger fusion molecule, formed by covalent or non-covalent association of the antibody with one or more other proteins or peptides.

The terms "full length antibody," "intact antibody" and "whole antibody" are used herein interchangeably to refer to an antibody in its substantially intact form, not antibody fragments as defined below. The terms particularly refer to an antibody with heavy chains that contain an Fc region.

A "naked antibody" for the purposes herein is an antibody that is not conjugated to a cytotoxic moiety or radiolabel.

"Antibody fragments" comprise a portion of an intact antibody, preferably comprising the antigen binding region thereof. In some embodiments, the antibody fragment described herein is an antigen-binding fragment. Examples of antibody fragments include Fab, Fab', F(ab')$_2$, and Fv fragments; diabodies; linear antibodies; single-chain antibody molecules; and multispecific antibodies formed from antibody fragments.

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen.

"Fv" is the minimum antibody fragment which contains a complete antigen-binding site. In one embodiment, a two-chain Fv species consists of a dimer of one heavy- and one light-chain variable domain in tight, non-covalent association. In a single-chain Fv (scFv) species, one heavy- and one light-chain variable domain can be covalently linked by a flexible peptide linker such that the light and heavy chains can associate in a "dimeric" structure analogous to that in a two-chain Fv species. It is in this configuration that the three HVRs of each variable domain interact to define an antigen-binding site on the surface of the VH-VL dimer. Collectively, the six HVRs confer antigen-binding specificity to the antibody. However, even a single variable domain (or half of an Fv comprising only three HVRs specific for an antigen) has the ability to recognize and bind antigen, although at a lower affinity than the entire binding site.

The Fab fragment contains the heavy- and light-chain variable domains and also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

"Single-chain Fv" or "scFv" antibody fragments comprise the VH and VL domains of antibody, wherein these domains are present in a single polypeptide chain. Generally, the scFv polypeptide further comprises a polypeptide linker between the VH and VL domains which enables the scFv to form the desired structure for antigen binding. For a review of scFv, see, e.g., Pluckthün, in *The Pharmacology of Monoclonal Antibodies*, vol. 113, Rosenburg and Moore eds., (Springer-Verlag, New York, 1994), pp. 269-315.

The term "diabodies" refers to antibody fragments with two antigen-binding sites, which fragments comprise a heavy-chain variable domain (VH) connected to a light-chain variable domain (VL) in the same polypeptide chain (VH-VL). By using a linker that is too short to allow pairing between the two domains on the same chain, the domains are forced to pair with the complementary domains of another chain and create two antigen-binding sites. Diabodies may be bivalent or bispecific. Diabodies are described more fully in, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

The term "monoclonal antibody" as used herein refers to an antibody obtained from a population of substantially homogeneous antibodies, e.g., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this disclosure. In contrast to polyclonal antibody preparations, which typically include different antibodies directed against different determinants (epitopes), each monoclonal antibody of a monoclonal antibody preparation is directed against a single determinant on an antigen. In addition to their specificity, monoclonal antibody preparations are advantageous in that they are typically uncontaminated by other immunoglobulins.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the disclosure may be made by a variety of techniques, including, for example, expression in a prokaryotic host cell, the hybridoma method (e.g., Kohler and Milstein, *Nature,* 256:495-97 (1975); Hongo et al., *Hybridoma,* 14 (3): 253-260 (1995), Harlow et al., *Antibodies: A Laboratory Manual,* (Cold Spring Harbor Laboratory Press, 2nd ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature,* 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and U.S. Pat. No. 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The monoclonal antibodies herein specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, e.g., U.S. Pat. No. 4,816,567; and Morrison et al., *Proc. Natl. Acad. Sci. USA* 81:6851-6855 (1984)). Chimeric antibodies include PRIMATTZED® antibodies wherein the antigen-binding region of the antibody is derived from an antibody produced by, e.g., immunizing macaque monkeys with the antigen of interest.

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from a HVR of the recipient are replaced by residues from a HVR of a non-human species (donor antibody) such as mouse, rat, rabbit, or nonhuman primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance. In general, a humanized antibody will comprise substantially all of at least one, and typically two, variable domains, in which all or substantially all of the hypervariable loops correspond to those of a non-human immunoglobulin, and all or substantially all of the FRs are those of a human immunoglobulin sequence. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, e.g., Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.,* 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA,* 103:3557-3562 (2006) regarding human antibodies generated via a human B-cell hybridoma technology.

A "species-dependent antibody" is one which has a stronger binding affinity for an antigen from a first mammalian species than it has for a homologue of that antigen from a second mammalian species. Normally, the species-dependent antibody "binds specifically" to a human antigen (e.g., has a binding affinity (Kd) value of no more than about $1 \times 10^{-7}$M, preferably no more than about $1 \times 10^{-8}$M and preferably no more than about $1 \times 10^{-9}$M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but preferably is a humanized or human antibody.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest,* 5th Ed. Public Health Service, National Institutes of Health, Bethesda, Md. (1991)). Chothia refers instead to the location of the structural loops (Chothia and Lesk *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

TABLE 1a

Antibody Hypervariable Regions

| Loop | Kabat | AbM | Chothia | Contact |
|---|---|---|---|---|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B (Kabat Numbering) |
| H1 | H31-H35 | H26-H35 | H26-H32 | H30-H35 (Chothia Numbering) |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

"Framework" or "FR" residues are those variable domain residues other than the HVR residues as herein defined.

The term "variable domain residue numbering as in Kabat" or "amino acid position numbering as in Kabat," and variations thereof, refers to the numbering system used for heavy chain variable domains or light chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy chain variable domain may include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues may be determined for a given antibody by alignment at regions of homology of the sequence of the antibody with a "standard" Kabat numbered sequence.

The Kabat numbering system is generally used when referring to a residue in the variable domain (approximately residues 1-107 of the light chain and residues 1-113 of the heavy chain) (e.g., Kabat et al., *Sequences of Immunological Interest.* 5th Ed. Public Health Service, National Institutes of Health, Bethesda, Md. (1991)). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody.

The expression "linear antibodies" refers to the antibodies described in Zapata et al. (1995 *Protein Eng,* 8(10):1057-1062). Briefly, these antibodies comprise a pair of tandem Fd segments (VH-CH1-VH-CH1) which, together with complementary light chain polypeptides, form a pair of antigen binding regions. Linear antibodies can be bispecific or monospecific.

II. Host Cells

Provided herein are host cells (e.g., prokaryotic host cells) with a host cell chromosome that comprises a translational unit encoding at least one chaperone protein (e.g., a peptidyl-prolyl isomerase or protein disulfide oxidoreductase) in operable combination or linkage with a promoter (also part of the host cell chromosome) that drives transcription of the translational unit, such that the combination of the promoter and the translational unit is non-native to the host cell or host cell chromosome.

In some embodiments, the host cell chromosome comprises: (1) a first polynucleotide comprising a first translational unit encoding a peptidyl-prolyl isomerase; and (2) a second polynucleotide comprising a second translational unit encoding a protein disulfide oxidoreductase; wherein the first and second translational units are part of the host cell chromosome and in operable combination or linkage with a first and a second (respectively) promoter (also part of the host cell chromosome) that drive transcription of the first and the second translation units, respectively. In some embodiments, the combination of the first translational unit and the first promoter and/or the combination of the second translational unit and the second promoter is/are non-native to the host cell chromosome. For example, one or both of the promoters can be non-native to the host cell chromosome, one or both of the translational units can be non-native to the host cell chromosome, or one or both of the translational units can be native to the host cell chromosome but operably combined with a promoter in a combination that is non-native to the host cell chromosome.

In some embodiments, the host cell further comprises one or more extra-chromosomal polynucleotide(s) that encode the two or more chains of a two-chain polypeptide of the present disclosure. For example, in some embodiments, the host cell comprises: (1) a first polynucleotide comprising a first translational unit encoding a first chain of a two-chain polypeptide of the present disclosure; (2) a second polynucleotide comprising a second translational unit encoding a second chain of the two-chain polypeptide of the present disclosure; and (3) a third polynucleotide comprising a third translational unit encoding a chaperone protein (e.g., a peptidyl-prolyl isomerase or protein disulfide oxidoreductase) in operable combination with a promoter that drives transcription of the third translational unit. In some embodiments, the combination of the third translational unit and the promoter is non-native to the host cell chromosome. In some embodiments, the first and second polynucleotides (i.e., encoding the first and second translational units, respectively) are part of one or more extra-chromosomal polynucleotide(s) (e.g., plasmid(s)), and the third polynucleotide (and associated promoter) is part of the host cell chromosome.

In some embodiments, the host cell comprises: (1) a first polynucleotide comprising a first translational unit encoding a first chain of a two-chain polypeptide of the present disclosure; (2) a second polynucleotide comprising a second translational unit encoding a second chain of the two-chain polypeptide of the present disclosure; (3) a third polynucleotide comprising a third translational unit encoding a protein disulfide oxidoreductase in operable combination with a promoter that drives transcription of the third translational unit; and (4) a fourth polynucleotide comprising a fourth translational unit encoding a peptidyl-prolyl isomerase in operable combination with a promoter that drives transcription of the fourth translational unit. In some embodiments, the combination of the third translational unit and its associated promoter and/or the combination of the fourth translational unit and its associated promoter is/are non-native to the host cell chromosome. In some embodiments, the first and second polynucleotides (i.e., encoding the first and second translational units, respectively) are part of one or more extra-chromosomal polynucleotide(s) (e.g., plasmid(s)), and the third and fourth polynucleotides (and associated promoters) are part of the host cell chromosome.

In some embodiments, the host cell comprises: (1) a first polynucleotide comprising a first translational unit encoding a first chain of a two-chain polypeptide of the present disclosure; (2) a second polynucleotide comprising a second translational unit encoding a second chain of the two-chain polypeptide of the present disclosure; (3) a third polynucleotide comprising a third translational unit encoding a protein disulfide oxidoreductase in operable combination with a first promoter that drives transcription of the third translational unit; and (4) a fourth polynucleotide comprising a fourth translational unit encoding a protein disulfide oxidoreductase in operable combination with a second promoter that drives transcription of the fourth translational unit. In some embodiments, the combination of the third translational unit and the first promoter and/or the combination of the fourth translational unit and the second promoter is/are non-native to the host cell chromosome. In some embodiments, the first and second polynucleotides (i.e., encoding the first and second translational units, respectively) are part of one or more extra-chromosomal polynucleotide(s) (e.g., plasmid(s)), and the third and fourth polynucleotides (and associated promoters) are part of the host cell chromosome.

In some embodiments, the host cell comprises: (1) a first polynucleotide comprising a first translational unit encoding a first chain of a two-chain polypeptide of the present disclosure; (2) a second polynucleotide comprising a second translational unit encoding a second chain of the two-chain polypeptide of the present disclosure; (3) a third polynucleotide comprising a third translational unit encoding a protein disulfide oxidoreductase in operable combination with a first promoter that drives transcription of the third translational unit; (4) a fourth polynucleotide comprising a fourth translational unit encoding a peptidyl-prolyl isomerase in operable combination with a second promoter that drives transcription of the fourth translational unit; and (5) a fifth polynucleotide comprising a fifth translational unit encoding a protein disulfide oxidoreductase in operable combination with a third promoter that drives transcription of the fifth translational unit. In some embodiments, the combination of the third translational unit and the first promoter, the combination of the fourth translational unit and the second promoter, and/or the combination of the fifth translational unit and the third promoter is/are non-native to the host cell chromosome. In some embodiments, the first and second polynucleotides (i.e., encoding the first and second translational units, respectively) are part of one or more extra-chromosomal polynucleotide(s) (e.g., plasmid(s)), and the third, fourth, and fifth polynucleotides (and associated promoters) are part of the host cell chromosome.

In some embodiments, a polynucleotide or translational unit of the present disclosure that encodes a chaperone protein (e.g., a peptidyl-prolyl isomerase or protein disulfide oxidoreductase) is native to the host cell chromosome. For example, the polynucleotide or translational unit encoding the chaperone protein may be a native chaperone protein gene or locus. In some embodiments, a promoter has been inserted into the host cell genome (e.g., by insertion into or replacement of one or more native regulatory sequences or genetic elements) so as to be in operable combination with a native chaperone protein gene or locus, generating a promoter:translational unit combination that is non-native to the host cell chromosome.

In other embodiments, a polynucleotide or translational unit of the present disclosure that encodes a chaperone protein (e.g., a peptidyl-prolyl isomerase or protein disulfide oxidoreductase) is non-native to the host cell (e.g., chromosomally integrated into a host cell).

In some embodiments, a host cell chromosome of the present disclosure may comprise one or more native translational unit(s) encoding a chaperone protein of the present disclosure and one or more non-native translational unit(s) encoding a chaperone protein of the present disclosure. In some embodiments, a host cell chromosome of the present disclosure may comprise multiple non-native translational units encoding a chaperone protein of the present disclosure. In addition, many of the host cells of the present disclosure are known to contain host cell chromosomes encoding multiple chaperone proteins (e.g., FkpA, DsbA, and DsbC of *E. coli*). In some embodiments, one or more of the native translational unit(s) encoding a chaperone protein of the present disclosure is operably combined with a promoter of the present disclosure in a combination that is non-native to the host cell or host cell chromosome.

Methods for introducing a polynucleotide or translational unit of the present disclosure into a host cell (e.g., a prokaryotic host cell) are known in the art. An exemplary method, allelic exchange, is described in greater detail infra. Advantageously, the allelic exchange method does not leave a "scar" on the host cell genome. Other methods include, without limitation, the method described in Datsenko, K. A. and Wanner, B. L. (2000) *Proc. Natl. Acad. Sci.* 97:6640-6645.

In some embodiments of any of the above embodiments, a host cell further comprises a translational unit encoding a third chain of a two-chain polypeptide of the present disclosure. In some embodiments, the translational unit is part of an extra-chromosomal polynucleotide encoding the first and/or second chain of the two-chain polypeptide. For example, in some embodiments the two-chain polypeptide is a one-armed antibody comprising, e.g., an immunoglobulin heavy chain, an immunoglobulin light chain, and an immunoglobulin Fc fragment that assemble to form a biologically active monovalent antibody (e.g., a monovalent antibody capable of specifically binding an antigen).

Chaperone Proteins

Certain aspects of the present disclosure relate to chaperone proteins. A chaperone protein may refer to any protein that aids in the folding or assembly of other macromolecules, including without limitation two chain proteins. Examples of chaperone proteins may include without limitation peptidyl-prolyl isomerases, protein disulfide oxidoreductases, and heat shock proteins (such as Hsp60, Hsp70, Hsp90, and Hsp100 proteins). Chaperone proteins may also aid in transporting proteins across membranes, e.g., translocation of polypeptide chains across the plasma membrane or endoplasmic reticulum membrane.

In some embodiments, a chaperone protein can be a peptidyl-prolyl isomerase. Peptidyl-prolyl isomerase (the terms "prolyl isomerase," "rotamase," and "PPiase" may be used interchangeably herein) may refer to any enzyme catalyzing the interconversion of cis and trans isomers of proline or prolyl-iminopeptide bonds. The EC number for this reaction is EC 5.2.1.8. Any protein known or predicted to catalyze the reaction described by this EC number may be a peptidyl-prolyl isomerase of the present disclosure. Peptidyl-prolyl isomerase activity may also be described by the GO term ID GO:0003755. Any protein known or predicted to possess the molecular function described by this GO term ID may be a peptidyl-prolyl isomerase of the present disclosure.

Peptidyl-prolyl isomerase activity is known in the art to promote protein folding and assembly. In some embodiments, peptidyl-prolyl isomerases may aid in protein folding and assembly by converting trans prolyl bonds to cis prolyl bonds for proteins whose properly folded structure includes a cis prolyl bond. Some peptidyl-prolyl isomerases are also known to enhance the folding and assembly of proteins that lack cis prolyl bonds (Bothmann H and Pluckthun A 2000 J. Biol. Chem. 275:17100). In some embodiments, peptidyl-prolyl isomerases may aid in protein folding and assembly of proteins that lack cis prolyl bonds. Thus, while peptidyl-prolyl isomerase activity may serve as a functional characteristic to identify a chaperone protein useful for the methods described herein, the utility of a peptidyl-prolyl isomerase is not necessarily limited to its catalytic activity per se.

In some embodiments, the peptidyl-prolyl isomerase is an FkpA protein. In some embodiments, the FkpA protein is *E. coli* FkpA. An *E. coli* FkpA may refer to any polypeptide encoded by an fkpA gene in any strain or isolate of bacteria belonging to the species *E. coli*. In some embodiments, *E. coli* FkpA refers a protein encoded by an fkpA gene described by EcoGene Accession Number EG12900. In some embodiments, *E. coli* FkpA refers a protein having the sequence described by the NCBI RefSeq Accession Number NP_417806.

Other FkpA proteins are known in the art. Examples of FkpA proteins may include, without limitation, *S. boydii* peptidyl-prolyl isomerase (NCBI RefSeq No. WP 000838252), *C. youngae* peptidyl-prolyl isomerase (NCBI RefSeq No. WP_006687366), *K. oxytoca* peptidyl-prolyl isomerase (NCBI RefSeq No. WP_004125943), *S. enterica* peptidyl-prolyl isomerase (NCBI RefSeq No. WP_000838233), *K. pneumoniae* peptidyl-prolyl isomerase (NCBI RefSeq No. WP_019704642), *S. cerevisiae* FPR3p (NCBI RefSeq No. NP_013637), *M. musculus* Fkpb1a (NCBI RefSeq No. NP_032045), *M. musculus* Fkpb2 (NCBI RefSeq No. NP_032046), *H. sapiens* FKBP2 (NCBI RefSeq No. NP_001128680), and *D. melanogaster* CG14715 (NCBI RefSeq No. NP_650101). In some embodiments, an FkpA protein of the present disclosure has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity to *E. coli* FkpA.

In some embodiments, a chaperone protein may be a protein disulfide oxidoreductase. Protein disulfide oxidoreductase (the terms "protein disulfide isomerase" and "thiol-disulfide isomerase" may be used interchangeably herein) may refer to any enzyme catalyzing the rearrangement of disulfide bonds in proteins. For example, a protein disulfide oxidoreductase may catalyze the oxidation of cysteines to form disulfide bonds in proteins. A protein disulfide oxidoreductase may also catalyze the isomerization of mispaired disulfide bonds in proteins. The EC number for this reaction is EC 5.3.4.1. Any protein known or predicted to catalyze the reaction described by this EC number may be a protein disulfide oxidoreductase of the present disclosure. Protein disulfide oxidoreductase activity may also be described by the GO term ID GO:0015035. Any protein known or predicted to possess the molecular function described by this GO term ID may be a protein disulfide oxidoreductase of the present disclosure.

Protein disulfide oxidoreductase activity is known in the art to promote protein folding and assembly. For example, protein disulfide oxidoreductase activity promotes the formation of proper intramolecular and intermolecular disulfide bonds during protein folding and assembly. In particular, protein disulfide oxidoreductase activity is important for proteins with disulfide bonds that are expressed in the periplasm of prokaryotic cells.

In some embodiments, the protein disulfide oxidoreductase is a DsbA protein. In some embodiments, the DsbA protein is *E. coli* DsbA. An *E. coli* DsbA may refer to any polypeptide encoded by a dsbA gene in any strain or isolate of bacteria belonging to the species *E. coli*. In some embodiments, *E. coli* DsbA refers a protein encoded by a dsbA gene described by EcoGene Accession Number EG11297. In some embodiments, *E. coli* DsbA refers a protein having the sequence described by the NCBI RefSeq Accession Number NP_418297.

Other DsbA proteins are known in the art. Examples of DsbA proteins may include, without limitation, *S. flexneri* thiol-disulfide isomerase (NCBI RefSeq No. WP_000725335), *S. dysenteriae* thiol-disulfide isomerase (NCBI RefSeq No. WP_000725348), *C. youngae* thiol-disulfide isomerase (NCBI RefSeq No. WP_006686108), and *S. enterica* thiol-disulfide isomerase (NCBI RefSeq No. WP_023240584). In some embodiments, a DsbA protein of the present disclosure has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity to *E. coli* DsbA.

In some embodiments, the protein disulfide oxidoreductase is a DsbC protein. In some embodiments, the DsbC protein is *E. coli* DsbC. An *E. coli* DsbC may refer to any polypeptide encoded by a dsbC gene in any strain or isolate of bacteria belonging to the species *E. coli*. In some embodiments, *E. coli* DsbC refers a protein encoded by a dsbC gene described by EcoGene Accession Number EG11070. In some embodiments, *E. coli* DsbC refers a protein having the sequence described by the NCBI RefSeq Accession Number NP_417369.

Other DsbC proteins are known in the art. Examples of DsbC proteins may include, without limitation, *S. sonnei* protein-disulfide isomerase (NCBI RefSeq No. WP_000715206), *S. dysenteriae* protein-disulfide isomerase (NCBI RefSeq No. WP_000715209), *E. fergusonii* protein-disulfide isomerase (NCBI RefSeq No. WP_000715225), *S. bongori* thiol:disulfide interchange protein DsbC (NCBI RefSeq No. WP_020845161), and *S. enterica* protein disulfide isomerase DsbC (NCBI RefSeq No. WP_023183515). In some embodiments, a DsbC protein of the present disclosure has at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% identity to *E. coli* DsbC.

To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In one embodiment, the length of a reference sequence aligned for comparison purposes is at least 50%, typically at least 75%, and even more typically at least 80%, 85%, 90%, 95% or 100% of the length of the reference sequence. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology").

The percent identity between the two sequences is a function of the number of identical positions shared by the sequences, taking into account the number of gaps, and the length of each gap, which need to be introduced for optimal alignment of the two sequences. For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters. When comparing two sequences for identity, it is not necessary that the sequences be contiguous, but any gap would carry with it a penalty that would reduce the overall percent identity. For blastn, the default parameters are Gap opening penalty=5 and Gap extension penalty=2. For blastp, the default parameters are Gap opening penalty=11 and Gap extension penalty=1.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted using known algorithms (e.g., by the local homology algorithm of Smith and Waterman, Adv Appl Math, 2:482, 1981; by the homology alignment algorithm of Needleman and Wunsch, J Mol Biol, 48:443, 1970; by the search for similarity method of Pearson and Lipman, Proc Natl Acad Sci USA, 85:2444, 1988; by computerized implementations of these algorithms FASTDB (Intelligenetics), BLAST (National Center for Biomedical Information), GAP, BESTFIT, FASTA, and TFASTA in the Wisconsin Genetics Software Package (Genetics Computer Group, Madison, Wis.), or by manual alignment and visual inspection.

A preferred example of an algorithm that is suitable for determining percent sequence identity and sequence similarity is the FASTA algorithm (Pearson and Lipman, Proc Natl Acad Sci USA, 85:2444, 1988; and Pearson, Methods Enzymol, 266:227-258, 1996). Preferred parameters used in a FASTA alignment of DNA sequences to calculate percent identity are optimized, BL50 Matrix 15:−5, k-tuple=2; joining penalty=40, optimization=28; gap penalty-12, gap length penalty=−2; and width=16.

Another preferred example of algorithms suitable for determining percent sequence identity and sequence similarity are the BLAST and BLAST 2.0 algorithms (Altschul et al., Nuc Acids Res, 25:3389-3402, 1977; and Altschul et al., J Mol Biol, 215:403-410, 1990, respectively). BLAST and BLAST 2.0 are used, with the parameters described herein, to determine percent sequence identity for the nucleic acids and proteins of the disclosure. Software for performing BLAST analyses is publicly available through the National Center for Biotechnology Information website. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E)

of 10, M=5, N=-4 and a comparison of both strands. For amino acid sequences, the BLASTP program uses as defaults a word length of 3, and expectation (E) of 10, and the BLOSUM62 scoring matrix (Henikoff and Henikoff, Proc Natl Acad Sci USA, 89:10915, 1989) alignments (B) of 50, expectation (E) of 10, M=5, N=-4, and a comparison of both strands.

The BLAST algorithm also performs a statistical analysis of the similarity between two sequences (See, e.g., Karlin and Altschul, Proc Natl Acad Sci USA, 90:5873-5787, 1993). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01, and most preferably less than about 0.001.

Another example of a useful algorithm is PILEUP. PILEUP creates a multiple sequence alignment from a group of related sequences using progressive, pairwise alignments to show relationship and percent sequence identity. It also plots a tree or dendrogram showing the clustering relationships used to create the alignment. PILEUP uses a simplification of the progressive alignment method (Feng and Doolittle, J Mol Evol, 35:351-360, 1987), employing a method similar to a published method (Higgins and Sharp, CABIOS 5:151-153, 1989). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. Using PILEUP, a reference sequence is compared to other test sequences to determine the percent sequence identity relationship using the following parameters: default gap weight (3.00), default gap length weight (0.10), and weighted end gaps. PILEUP can be obtained from the GCG sequence analysis software package, e.g., version 7.0 (Devereaux et al., Nuc Acids Res, 12:387-395, 1984).

Another preferred example of an algorithm that is suitable for multiple DNA and amino acid sequence alignments is the CLUSTALW program (Thompson et al., Nucl Acids. Res, 22:4673-4680, 1994). ClustalW performs multiple pairwise comparisons between groups of sequences and assembles them into a multiple alignment based on homology. Gap open and Gap extension penalties were 10 and 0.05 respectively. For amino acid alignments, the BLOSUM algorithm can be used as a protein weight matrix (Henikoff and Henikoff, Proc Natl Acad Sci USA, 89:10915-10919, 1992).

Promoters

Expression and cloning vectors generally contain a promoter that is recognized by the host organism and is operably linked to nucleic acid encoding an antibody. Promoters suitable for use with prokaryotic hosts include the phoA promoter, β-lactamase and lactose promoter systems, alkaline phosphatase promoter, a tryptophan (trp) promoter system, and hybrid promoters such as the tac promoter. However, other known bacterial promoters are suitable. Promoters for use in bacterial systems also will contain a Shine-Dalgarno (S.D.) sequence operably linked to the DNA encoding an antibody. As discussed above, a promoter can be inserted into a host cell chromosome in operable combination with a translational unit (e.g., a native translational unit, such as that encoding a chaperone protein of the present disclosure) to generate a promoter:translational unit combination that is non-native to the host cell or host cell chromosome.

In some embodiments, a promoter of the present disclosure is an inducible promoter. The activity of an inducible promoter increases or decreases in response to a signal. For example, an inducible promoter may promote transcription in response to the presence of a signal, such as IPTG. An inducible promoter may promote transcription in response to the absence of a signal, such as phosphate. In either of these scenarios, the amount of transcription may or may not be proportional to the amount of signal, or the deficiency thereof. Numerous examples of inducible promoters suitable for prokaryotic host cells are known in the art. These may include, without limitation, lac, tac, trc, trp, pho, recA, tetA, nar, phage $P_L$, cspA, T7, and PBAD promoters (see Terpe K. 2006 Appl. Microbiol. Biotechnol. 72:211 for more detailed description). In some embodiments, multiple copies of an inducible promoter are used to drive expression of separate translational units, e.g., encoding chaperone proteins such as DsbC and FkpA, in a coordinated manner.

In some embodiments, the inducible promoter is an IPTG-inducible promoter. An IPTG-inducible promoter may refer to any polynucleotide sequence that promotes transcription in a manner responsive to isopropyl β-D-1-thiogalactopyranoside (IPTG) or any other lactose derivative that is able to promote transcription from the lac operon (e.g., allolactose). Many examples of IPTG-inducible promoters are known in the art, including without limitation tac (e.g, tacI, tacII, etc.) promoters, lac promoters, and derivatives thereof (e.g., lacUV5, taclac, and so forth).

In some embodiments, the inducible promoter is a pho promoter that drives transcription of a translational unit when phosphate in the culture medium has been depleted. A pho promoter may refer to any polynucleotide sequence that promotes transcription in a manner responsive to extracellular phosphate (for example, inorganic phosphate). For example, the phosphate (Pho) regulon in *E. coli* includes protein components that sense extracellular phosphate and, in response to phosphate levels, regulate the expression of numerous downstream genes through Pho promoters (see Hsieh Y J and Wanner B L 2010 Curr. Opin. Microbiol. 13(2):198 for more detailed description). When bacteria are grown in a culture medium, expression of this Pho regulon is known to be repressed when phosphate (e.g., inorganic phosphate, Pi) is available in the medium and induced when phosphate has been depleted. One non-limiting example of a pho promoter used in the methods described herein is the *E. coli* phoA promoter. This promoter is widely known and used in the art to regulate recombinant protein expression in prokaryotic host cells in a manner dependent upon the concentration of phosphate in the cell culture medium (see Lubke C et al. 1995 Enzyme Microb. Technol. 17(10):923 for more detailed description).

In some embodiments, a promoter of the present disclosure is a constitutive promoter. The activity of a constitutive promoter is thought to remain at a constant level of gene expression regardless of variance in conditions under which the host cell is grown (e.g., nutrient conditions, cell density, etc.). For example, the activity of a constitutive promoter can be dependent on RNA polymerase availability, rather than activity or expression of one or more transcription factors. In some embodiments, the promoter is a synthetic or non-naturally occurring promoter. Exemplary constitutive promoters suitable for a range of prokaryotic host cells are described, e.g., in Jensen P R, Hammer K. Appl Environ Microbiol 1998; 64: 82-87. In some embodiments, the constitutive promoter is a CP25 promoter.

As described herein, a host cell chromosome of the present disclosure can comprise multiple non-native combinations of a promoter operably linked or combined with a translational unit encoding a chaperone protein of the present disclosure. Different types of promoters may be inserted into the host cell chromosome in any number or combination. For example, in some embodiments, a host cell chromosome of the present disclosure comprises an inducible promoter (e.g., operably combined with a translational unit encoding a chaperone protein of the present disclosure) and a constitutive promoter (e.g., operably combined with a different translational unit encoding a chaperone protein of the present disclosure). For example, in some embodiments, a host cell chromosome of the present disclosure comprises an inducible promoter of the present disclosure operably combined with a translational unit encoding a chaperone protein of the present disclosure and a constitutive promoter of the present disclosure operably linked with a different translational unit encoding a chaperone protein of the present disclosure, wherein both combinations of promoter: translational unit are non-native to the host cell or host cell chromosome.

In some embodiments, a host cell chromosome of the present disclosure comprises a Pho promoter of the present disclosure operably linked with a translational unit encoding a chaperone protein of the present disclosure and a CP25 promoter of the present disclosure operably linked with a different translational unit encoding a chaperone protein of the present disclosure. In some embodiments, a host cell chromosome of the present disclosure comprises a Pho promoter of the present disclosure operably linked with a translational unit encoding a protein disulfide oxidoreductase of the present disclosure and a CP25 promoter of the present disclosure operably linked with a translational unit encoding a peptidyl-prolyl isomerase of the present disclosure. In some embodiments, a host cell chromosome of the present disclosure comprises a Pho promoter of the present disclosure operably linked with a translational unit encoding DsbC and a CP25 promoter of the present disclosure operably linked with a translational unit encoding FkpA. In some embodiments, a host cell chromosome of the present disclosure comprises a Pho promoter of the present disclosure operably linked with a translational unit encoding E. coli DsbC and a CP25 promoter of the present disclosure operably linked with a translational unit encoding E. coli FkpA. In some embodiments, the host cell is E. coli, and the translational units encoding DsbC and FkpA are native. In some embodiments, the host cell further comprises one or more extra-chromosome polynucleotides comprising two or more translational units encoding the two or more polypeptide chains of a two-chain polypeptide of the present disclosure.

In some embodiments, a host cell chromosome of the present disclosure comprises a Pho promoter of the present disclosure operably linked with a translational unit encoding a chaperone protein of the present disclosure and a Pho promoter of the present disclosure operably linked with a different translational unit encoding a chaperone protein of the present disclosure. In some embodiments, a host cell chromosome of the present disclosure comprises a Pho promoter of the present disclosure operably linked with a translational unit encoding a protein disulfide oxidoreductase of the present disclosure and a Pho promoter of the present disclosure operably linked with a translational unit encoding a peptidyl-prolyl isomerase of the present disclosure. In some embodiments, a host cell chromosome of the present disclosure comprises a Pho promoter of the present disclosure operably linked with a translational unit encoding DsbC and a Pho promoter of the present disclosure operably linked with a translational unit encoding FkpA. In some embodiments, a host cell chromosome of the present disclosure comprises a Pho promoter of the present disclosure operably linked with a translational unit encoding E. coli DsbC and a Pho promoter of the present disclosure operably linked with a translational unit encoding E. coli FkpA. In some embodiments, the host cell is E. coli, and the translational units encoding DsbC and FkpA are native. In some embodiments, the host cell further comprises one or more extra-chromosome polynucleotides comprising two or more translational units encoding the two or more polypeptide chains of a two-chain polypeptide of the present disclosure.

In some embodiments, a host cell chromosome of the present disclosure comprises a tac promoter of the present disclosure operably linked with a translational unit encoding a chaperone protein of the present disclosure, a tac promoter of the present disclosure operably linked with a second translational unit encoding a chaperone protein of the present disclosure, and a CP25 promoter of the present disclosure operably linked with a third translational unit encoding a chaperone protein of the present disclosure. In some embodiments, a host cell chromosome of the present disclosure comprises a tac promoter of the present disclosure operably linked with a translational unit encoding a protein disulfide oxidoreductase of the present disclosure, a tac promoter of the present disclosure operably linked with a second translational unit encoding a protein disulfide oxidoreductase of the present disclosure, and a CP25 promoter of the present disclosure operably linked with a third translational unit encoding a peptidyl-prolyl isomerase of the present disclosure. In some embodiments, a host cell chromosome of the present disclosure comprises a tac promoter of the present disclosure operably linked with a translational unit encoding DsbC, a tac promoter of the present disclosure operably linked with a translational unit encoding DsbA, and a CP25 promoter of the present disclosure operably linked with a translational unit encoding FkpA. In some embodiments, a host cell chromosome of the present disclosure comprises a tac promoter of the present disclosure operably linked with a translational unit encoding E. coli DsbC, a tac promoter of the present disclosure operably linked with a translational unit encoding E. coli DsbA, and a CP25 promoter of the present disclosure operably linked with a translational unit encoding E. coli FkpA. In some embodiments, the host cell is E. coli, and the translational units encoding DsbC, DsbA, and FkpA are native. In some embodiments, the host cell further comprises one or more extra-chromosome polynucleotides comprising two or more translational units encoding the two or more polypeptide chains of a two-chain polypeptide of the present disclosure.

Extra-Chromosomal Polynucleotides and Expression Vectors

In some embodiments, a host cell contains (1) a first polynucleotide comprising a first translational unit encoding a first chain of a two-chain polypeptide of the present disclosure; and (2) a second polynucleotide comprising a second translational unit encoding a second chain of the two-chain polypeptide. In some embodiments, the first and second polynucleotides are part of one or more extra-chromosomal polynucleotides. In some embodiments, the first and second polynucleotides are part of the same extra-chromosomal polynucleotide. In some embodiments, the extra-chromosomal polynucleotide(s) further comprises a third translational unit encoding a third chain of the two-chain polypeptide. In some embodiments, the extra-chromosomal polynucleotide(s) comprise one or more expression vectors or plasmids.

In some embodiments, the first translational unit encoding the first chain of the two-chain polypeptide and the second translational unit encoding the second chain of the two-chain polypeptide are part of a single extra-chromosomal polynucleotide (e.g., a plasmid or other expression vector). In some embodiments, the first translational unit encoding the first chain of the two-chain polypeptide and the second translational unit encoding the second chain of the two-chain polypeptide are expressed from separate extra-chromosomal polynucleotides (e.g., plasmids or other expression vectors).

In some embodiments, the extra-chromosomal polynucleotide(s) further contain a selectable marker (e.g., a translational unit encoding a selectable marker protein). A selectable marker may refer to any polynucleotide that encodes a protein that promotes the survival of a host cell when the cell undergoes selection, i.e., any condition used to preferentially increase the abundance of cell(s) bearing a selectable marker relative to the abundance of cell(s) lacking the selectable marker. Typical selection markers encode proteins that (a) confer resistance to antibiotics or other toxins, e.g., ampicillin, neomycin, methotrexate, or tetracycline, (b) complement auxotrophic deficiencies, or (c) supply critical nutrients not available from complex media, e.g., the gene encoding D-alanine racemase for Bacilli. Numerous selectable markers and corresponding selection agents with single antibiotics are known in the art. For example and without limitation, many selectable markers and corresponding antibiotics are described and cited in Jang C W and Magnuson T 2013 PLoS ONE 8(2):e57075. In some embodiments, a selectable marker may refer to a gene (e.g., a gene expressed from a plasmid) that complements a gene deletion present within the host cell's genome. In these examples, when the cell undergoes selection (i.e., growth under a condition that requires the activity of the gene deleted from the host genome), the copy of the gene supplied by the plasmid complements the deficiency of the host genome, thereby selecting for cell(s) bearing the exogenous complementing gene. Such genes may include auxotrophic markers or genes required to produce a specific nutrient lacking in a cell medium, examples of which are further described herein. Several exemplary selectable markers and antibiotics are further described herein.

In some embodiments, the selectable marker promotes resistance to a selection agent, and the culture medium includes the selection agent to cause the host cell to retain the polynucleotide. In some embodiments, the selection agent is an antibiotic. One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another selection scheme uses a prokaryotic host cell with a chromosomal deletion removing a gene whose gene product is essential for growth in a particular culture medium. In these examples, those cells that are successfully transformed with a heterologous gene that complements the chromosomal deletion of the host cell will survive when grown in the particular culture medium. Examples of genes useful in this schemes may include auxotrophic marker genes or other genes that are required to generate an essential nutrient when the host cell is grown in a particular culture medium.

In some embodiments, the extra-chromosomal polynucleotide(s) further contain an origin of replication suitable for replicating the extra-chromosomal expression vector in the prokaryotic host cell. Generally, in cloning vectors this sequence is one that enables the vector to replicate independently of the host chromosomal DNA, and includes origins of replication or autonomously replicating sequences. Such sequences are well known for a variety of prokaryotic host cells. For example, the origin of replication from the plasmid pBR322 is suitable for most Gram-negative bacteria.

Expression vectors used in prokaryotic host cells may also contain sequences necessary for the termination of transcription and for stabilizing the mRNA. In prokaryotic cells, terminators may include Rho-dependent or Rho-independent terminators. One example of a terminator useful in prokaryotic host cells includes without limitation the λt0 terminator (Scholtissek and Grosse, Nucleic Acids Res. 15:3185, 1987).

An antibody of the disclosure may be produced recombinantly not only directly, but also as a fusion polypeptide with a heterologous polypeptide, which is preferably a signal sequence or other polypeptide having a specific cleavage site at the N-terminus of the mature protein or polypeptide. The heterologous signal sequence selected preferably is one that is recognized and processed (e.g., cleaved by a signal peptidase) by the host cell. For prokaryotic host cells that do not recognize and process a native antibody signal sequence, the signal sequence is substituted by a prokaryotic signal sequence selected, for example, from the group of the alkaline phosphatase, penicillinase, lpp, or heat-stable enterotoxin II leaders.

Recombinant Polypeptides

Certain aspects of the present disclosure relate to methods of producing two-chain polypeptides. Advantageously, the methods described herein may be useful for promoting the expression, folding and assembly of many different types of proteins, particularly those with disulfide bonds, such as two chain proteins as described above. Particular two chain proteins are described below, but the methods described herein are not limited to these particular embodiments. As used herein, two chain proteins may include proteins containing more than one distinct polypeptide chain. Although many embodiments described herein involve two chain proteins with two polypeptide chains, two chain proteins with more than two polypeptide chains (e.g., three or more polypeptides) are contemplated and may be produced by the methods described herein. As described above, two chain proteins made of a single polypeptide chain that otherwise associate as they would if they were two distinct polypeptide chains (e.g., single chain antibodies, single chain variable fragments, and the like) are also contemplated and may be produced by the methods described herein.

In some embodiments, the two chains of a two chain polypeptide of the present disclosure are linked to each other by at least one disulfide bond. Disulfide bonds may refer to any covalent bond linking two thiol groups. Disulfide bonds in polypeptides typically form between the thiol groups of cysteine residues. Polypeptide disulfide bonds are known in the art to be important for the folding and assembly of many polypeptides, such as two chain proteins of the present disclosure. Polypeptide disulfide bonds may include disulfide bonds between cysteine residues in a single polypeptide chain (i.e., intramolecular or intra-chain disulfide bonds). Polypeptide disulfide bonds may also include disulfide bonds between cysteine residues found on separate polypeptide chains (i.e., intermolecular or inter-chain disulfide bonds). Therefore, in some embodiments, two chains of a two chain polypeptide are linked to each other by at least one disulfide bond.

Disulfide bonds are known in the art to be important for the folding and assembly of antibodies and antibody fragments. Different antibody isotypes, and different subclasses within an isotope, are known to possess different patterns of disulfide bonds. For example, IgG antibodies may contain 12 intra-chain disulfide bonds, one inter-chain disulfide bond between each light chain and its corresponding heavy chain, and between 2 and 11 inter-chain disulfide bonds between heavy chains, depending upon the particular IgG subclass (see Liu H and May K 2012 MAbs. 4(1):17 for more detailed description). IgM (see, e.g., Wiersma E J and Shulman M J 1995 J. Immunol. 154(10):5265), IgE (see, e.g., Helm B A et al. 1991 Eur. J. Immunol. 21(6):1543), IgA (see, e.g., Chintalacharuvu K R et al. 2002 J. Immunol. 169(9):5072), and IgD (see, e.g., Shin S U et al. 1992 Hum. Antibodies Hybridomas 3(2):65) are also known to form disulfide bonds during folding and assembly.

In some embodiments, a two chain polypeptide of the present disclosure is heterologous to the host cell. As used herein, a heterologous polypeptide when used in reference to a host cell may refer to any polypeptide that is not natively expressed in the host cell, i.e., when the host cell is isolated from nature. A heterologous polypeptide may also refer to a polypeptide that may be expressed natively by the host cell, but is expressed under different regulation than when the host cell is isolated from nature. Examples of different regulation may include without limitation a different amount of expression, expression in response to a different stimulus, or any other altered context of expression, such as by use of a heterologous promoter, such as an inducible promoter.

In some embodiments, a two chain polypeptide of the present disclosure is a monomer of a heterodimer. As used herein, a heterodimer may refer to any polypeptide complex that contains two distinct polypeptides or polypeptide complexes in operable linkage. A non-limiting example of a heterodimer is a bispecific or bivalent antibody composed of two distinct antibody monomers (i.e., a light chain-heavy chain pair in operable linkage). In this example, the folding and assembly of a first heavy chain-light chain pair recognizing a first antigen produces a first antibody monomer. The folding and assembly of a second heavy chain-light chain pair recognizing a second antigen produces a second antibody monomer. These monomers may be assembled by any means known in the art (described below in more detail with respect to bispecific antibodies) to form a heterodimer. For more details on an illustrative example of heterodimeric antibody formation, see Ridgway J B B et al. 1996 Protein Eng. 9(7):617.

In some embodiments, a two chain polypeptide of the present disclosure is a monovalent antibody in which the first chain and the second chain represent an immunoglobulin heavy chain and an immunoglobulin light chain. As used herein, a monovalent antibody may refer to any polypeptide complex made from an antibody heavy chain and an antibody light chain operably linked together to form a heavy chain-light chain pair in which the heavy chain-light chain pair is not operably linked to a second heavy chain-light chain pair. The term "half-antibody (hAb)" may be used interchangeably herein.

In some embodiments, a monovalent antibody of the present disclosure is capable of specifically binding an antigen. As used herein, the term "binds", "specifically binding an," or is "specific for" refers to measurable and reproducible interactions such as binding between a target (i.e., and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 μM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require, exclusive binding.

In some embodiments, a two chain polypeptide of the present disclosure is a secretory protein. As used herein, a secretory protein may refer to any protein that is secreted by a host cell into the host cell periplasm or extracellular milieu. A secretory protein may be a protein that is natively secreted by a host cell, or a secretory protein may be a protein that is not natively secreted by a host cell but is modified in such a way as to promote its secretion. For example, the presence of a signal sequence, typically found at the N-terminus of a polypeptide, may direct a polypeptide to the secretory pathway for secretion. Numerous signal sequences are known in the art and may be useful for promoting the secretion of a secretory protein or allowing the secretion of protein not naturally secreted by a host cell; see, e.g., Picken et al., Infect. Immun. 42:269-275 (1983); Simmons and Yansura, Nature Biotechnology 14:629-634 (1996); and Humphreys D P et al. 2000 Protein Expr. Purif. 20(2):252. One non-limiting example of a signal sequence is a heat stable enterotoxin II (STII) signal sequence.

In some embodiments, a secretory protein of the present disclosure is recovered from the periplasm of the host cell. Periplasm is known in the art to refer to the space between the inner or cytoplasmic membrane and the outer membrane of a Gram-negative bacterial cell. Without wishing to be bound to theory, it is thought that the periplasm is an oxidizing environment that favors the formation of disulfide bonds. Therefore, it may be advantageous to localize a polypeptide with disulfide bonds as part of its properly folded and assembled structure (e.g., a two chain protein of the present disclosure) to the periplasm (see Schlapschy M et al. 2006 Protein Eng. Des. Sel. 19(8):385 for more detailed description).

Numerous methods for recovering a periplasmic protein are known in the art. One non-limiting example of large-scale purification of periplasmic proteins is described in European Patent No. EP1356052 B1 (see, e.g., Example 4). Periplasmic proteins may be recovered by extracting a periplasmic fraction from a spheroblast preparation (see, e.g., Schlapschy M et al. 2006 Protein Eng. Des. Sel. 19(8):385). Once a periplasmic extract has been generated, periplasmic proteins may be purified by any standard protein purification technique known in the art, such as affinity purification, chromatography, and the like.

Host Cells

Certain aspects of the present disclosure relate to prokaryotic host cells. Suitable prokaryotes for cloning or expressing the DNA in the vectors herein include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41P disclosed in DD 266,710 published 12 Apr. 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In some embodiments, the prokaryotic host cell is a gram-negative bacterium. Gram-negative bacterium refers to any bacterium that contains an outer membrane surrounding the peptidoglycan layer detected by Gram staining. Many gram-negative bacterial host cells are known in the art. For example, gram-negative bacteria are known to include without limitation proteobacteria, such as Alphaproteobacteria, Betaproteobacteria, Gammaproteobacteria, Zetaproteobacteria, Epsilonproteobacteria, Deltaproteobacteria, and Acidobacteria; cyanobacteria; and spirochaetes. Well known gram-negative bacteria may include species from genera such as *Eschericia, Salmonella, Shigella, Pseudomonas, Hehobacter, Legionella, Neisseria*, and *Klebsiella*.

In some embodiments, a gram-negative bacterium of the present disclosure is *E. coli*. As used herein, *E. coli* may refer to any strain or isolate of bacteria belonging to the species *E. coli*. *E. coli* may include naturally occurring strains or strains that have been genetically modified, such as by mutation or transformation with a plasmid as described herein.

In some embodiments, an *E. coli* of the present disclosure is of a strain deficient in endogenous protease activity. Without wishing to be bound by theory, it is thought that strains deficient in endogenous protease activity may allow for enhanced production of recombinant proteins, such as periplasmic proteins of the present disclosure, because some endogenous proteases have activity against recombinantly expressed substrates (see Baneyx F and Georgiu G 1990 J. Bacteriol. 172(1):491 for one such example). Strains deficient in endogenous protease activity may include strains in which a gene encoding an endogenous protease is mutated, deleted, or otherwise inactivated. Examples of such genes may include, without limitation, degP, prc, and ompT. Methods for introducing mutations in a wide variety of prokaryotic host cells (e.g., for engineering strains deficient in endogenous protease activity) are well known in the art; see, e.g., Snyder L et al. 2013 Molecular Genetics of Bacteria 4th ed. ASM Press). In certain embodiments, an *E. coli* of the present disclosure is of a strain with a degpS210A mutation.

In some embodiments, an *E. coli* of the present disclosure is of a strain with enhanced LacI production or activity. The sequence of an exemplary LacI protein is represented by UniProt KB Accession No. P03023. In certain embodiments, the *E. coli* is a strain with a lacI$^Q$ mutation (see, e.g., Muller-Hill, B. et al. (1968) *Proc. Natl. Acad. Sci.* 59:1259-1264). This mutation is known to result in overproduction of the LacI repressor of the lac operon.

In certain embodiments, an *E. coli* of the present disclosure is of the strain ΔfhuA ΔphoA iivG2096 (IlvG+; Valr) Δprc spr43H1 ΔmanA lac' ΔompT ΔmenE742 degPS210A.

Antibodies and Antibody Fragments

The two chain proteins described herein may be prepared by any suitable techniques known in the art. One exemplary class of two chain proteins is the antibody. As described below, antibodies are prepared using techniques available in the art for generating antibodies, exemplary methods of which are described in more detail in the following sections. One of skill in the art will recognize that many of the methods described below may be applied to two chain proteins other than antibodies.

The antibody is directed against an antigen of interest (e.g., and without limitation, PD-L1 (such as a human PD-L1), HER2, or CD3 (such as a human CD3), IL13, IL4, VEGFC, VEGFA, and VEGF). Preferably, the antigen is a biologically important polypeptide and administration of the antibody to a mammal suffering from a disorder can result in a therapeutic benefit in that mammal.

In some embodiments, an antibody of the present disclosure is directed against interleukin-13 (referred to herein as IL-13 or IL13). For example, the antibody may be a monovalent antibody or "half-antibody" directed against IL13, a full antibody comprising two monovalent heavy chain-light chain pairs directed against IL13 (e.g., two identical monovalent heavy chain-light chain pairs; two monovalent heavy chain-light chain pairs, each comprising different HVRs or CDRs that recognize identical epitopes of IL13; or two monovalent heavy chain-light chain pairs, each comprising different HVRs or CDRs that recognize non-overlapping or partially overlapping epitopes of IL13), or a bispecific antibody comprising a heavy chain-light chain pair directed against IL13 and a heavy chain-light chain pair directed against a different antigen.

Examples of IL13 polypeptides are known in the art. In some embodiments, the IL13 polypeptide is a human IL13 polypeptide. In some embodiments, the IL13 polypeptide is a precursor form of IL13. A non-limiting example of a precursor form of an IL13 polypeptide is a human IL13 precursor, as represented by Swiss-Prot Accession No. P35225.2. In some embodiments, the IL13 polypeptide comprises the sequence:

```
                                        (SEQ ID NO: 1)
MALLLTTVIA LTCLGGFASP GPVPPSTALRELIEEL VNITQNQKAP

LCNGSMVWSI NLTAGMYCAA LESLINVSGC SAIEKTQRML

SGFCPHKVSA GQFSSLHVRD TKIEVAQFVK DLLLHLKKLF

REGRFN.
```

In other embodiments, the IL13 is a mature form of IL13 (e.g., lacking a signal sequence). In some embodiments, the IL13 polypeptide comprises the sequence:

```
                                        (SEQ ID NO: 2)
  SPGPVPPSTALR ELIEELVNIT QNQKAPLONG SMVWSINLTA

GMYCAALESL INVSGCSAIE KTORMLSGFC PHKVSAGQFS

SLHVRDTKIE VAQFVKDLLL HLKKLFREGR FN.
```

In some embodiments, provided herein is an anti-IL13 antibody comprising a heavy chain variable domain and a light chain variable domain, wherein:
- (a) the heavy chain variable domain comprises an HVR-H1, HVR-H2 and an HVR-H3 sequence having at least 85% sequence identity to AYSVN(SEQ ID NO:5), MIWGDGKIVYNSALKS (SEQ ID NO:6) and DGYYPYAMDN (SEQ ID NO:7), respectively, and/or
- (b) the light chain variable domain comprises an HVR-L1, HVR-L2 and an HVR-L3 sequence having at least 85% sequence identity to RASKSVDSYGNSFMH (SEQ ID NO:8), LASNLES (SEQ ID NO:9) and QQNNEDPRT (SEQ ID NO:10), respectively.

In a specific aspect, the sequence identity is at least 86%, 87%, 88%, 89%, 90%, 91%, 92%, 93%, 94%, 95%, 96%, 97%, 98%, 99% or 100% as compared to a reference sequence.

In some embodiments, the anti-IL13 antibody comprises a heavy chain variable domain sequence of SEQ ID NO:3 and/or a light chain variable domain sequence of SEQ ID NO:4. In a still further embodiment, provided is an isolated anti-IL13 antibody comprising a heavy chain and/or a light chain sequence, wherein:
- (a) the heavy chain variable domain sequence has at least 85%, at least 90%, at least 91%, at least 92%, at least 93%, at least 94%, at least 95%, at least 96%, at least 97%, at least 98%, at least 99% or 100% sequence identity to the reference heavy chain sequence:

```
                                          (SEQ ID NO: 3)
EVTLRESGPALVKPTQTLTLTCTVSGFSLSAYSVNWIRQPPGKALEWLA

MIWGDGKIVYNSALKSRLTISKDTSKNQVVLTMTNMDPVDTATYYCAGD

GYYPYAMDNWGQGSLVTVSS,
``` and/or
- (b) the light chain variable domain sequence has at least 85%, at least 90%, at least 91%, at least 92%, at least 93%, at least 94%, at least 95%, at least 96%, at least 97%, at least 98%, at least 99% or 100% sequence identity to the reference light chain sequence:

```
                                          (SEQ ID NO: 4)
DIVLTQSPDSLSVSLGERATINCRASKSVDSYGNSFMHWYQQKPGQPPK

LLIYLASNLESGVPDRFSGSGSGTDFTLTISSLQAEDVAVYYCQQNNED

PRTFGGGTKVEIKR.
```

In some embodiments, an antibody of the present disclosure is directed against interleukin-33 (referred to herein as IL-33 or IL33). For example, the antibody may be a monovalent antibody or "half-antibody" directed against IL33, a full antibody comprising two monovalent heavy chain-light chain pairs directed against IL33 (e.g., two identical monovalent heavy chain-light chain pairs; two monovalent heavy chain-light chain pairs, each comprising different HVRs or CDRs that recognize identical epitopes of IL33; or two monovalent heavy chain-light chain pairs, each comprising different HVRs or CDRs that recognize non-overlapping or partially overlapping epitopes of IL33), or a bispecific antibody comprising a heavy chain-light chain pair directed against IL33 and a heavy chain-light chain pair directed against a different antigen.

Various isoforms of IL33 are known. For example, human IL33 isoforms include, for example and without limitation, those represented by NCBI RefSeq Accession Nos. AOZ26495, ADR77828, AAH47085, NP_254274, NP_001186569, NP_001300977, NP_001340731, NP_001300975, NP_001300976, and XP 06870774.

In one aspect, multispecific antibodies are provided, wherein the antibodies comprise a first monovalent or half antibody and a second monovalent or half antibody, wherein the first half-antibody comprises a first VH/VL unit that binds IL-33 and the second half antibody comprises a second VH/VL unit that binds IL-13.

HVR and variable domain sequences for exemplary anti-IL33 antibodies (including anti-IL33/anti-IL13 bispecific antibodies) can be found, e.g., in WO2016077381.

In some embodiments, the CH3 and/or CH2 domains of an antibody of the present disclosure are from an IgG (e.g., IgG1 subtype, IgG2 subtype, IgG2A subtype, IgG2B subtype, IgG3, subtype, or IgG4 subtype). In some embodiments, the CH3 and/or CH2 domains of an antibody of the present disclosure may comprise one or more knob- or hole-forming mutations, such as those described in Table 2 below.

In certain embodiments, the CH3 and/or CH2 domains of an antibody of the present disclosure are from an IgG4 subtype. In some embodiments, the IgG4 CH3 and/or CH2 domains of an antibody of the present disclosure may comprise one or more additional mutations, including without limitation an S228P mutation (EU numbering).

In some embodiments, an antibody of the present disclosure is an antibody fragment, as discussed in greater detail infra. As used herein, an antibody fragment refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

In some embodiments, an antibody of the present disclosure is a one-armed antibody. In some embodiments, a one-armed antibody comprises an immunoglobulin heavy chain, an immunoglobulin light chain, and an immunoglobulin Fc fragment, where the three chains fold and assemble to form a biologically active monovalent antibody. For description of the exemplary and non-limiting one-armed antibody onartuzumab (e.g., MetMAb), see, e.g., Merchant, M. et al. (2013) *Proc. Natl. Acad. Sci.* 110:E2987-E2996.

Antibody Properties

In certain embodiments, an antibody provided herein has a dissociation constant (Kd) of ≤1 µM, ≤150 nM, ≤100 nM, ≤50 nM, ≤10 nM, ≤1 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$M).

In one embodiment, Kd is measured by a radiolabeled antigen binding assay (MA) performed with the Fab version of an antibody of interest and its antigen as described by the following assay. Solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881(1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen are mixed with serial dilutions of a Fab of interest. The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20®) in PBS. When the plates have dried, 150 µl/well of scintillant (MICROSCINT-20™; Packard) is added, and the plates are counted on a TOP-COUNT™ gamma counter (Packard) for ten minutes. Concentrations of each Fab that give less than or equal to 20% of maximal binding are chosen for use in competitive binding assays.

According to another embodiment, Kd is measured using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NETS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE ° Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ M$^{-1}$ s$^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

(i) Antigen Preparation

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule. Other antigens and forms thereof useful for preparing antibodies will be apparent to those in the art.

(ii) Certain Antibody-Based Methods

Polyclonal antibodies are preferably raised in animals by multiple subcutaneous (sc) or intraperitoneal (ip) injections of the relevant antigen and an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N{=}C{=}NR$, where R and $R^1$ are different alkyl groups.

Animals are immunized against the antigen, immunogenic conjugates, or derivatives by combining, e.g., 100 µg or 5 µg of the protein or conjugate (for rabbits or mice, respectively) with 3 volumes of Freund's complete adjuvant and injecting the solution intradermally at multiple sites. One month later the animals are boosted with ⅕ to ¹⁄₁₀ the original amount of peptide or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies of the disclosure can be made using the hybridoma method first described by Kohler et al., *Nature*, 256:495 (1975), and further described, e.g., in Hongo et al., *Hybridoma*, 14 (3): 253-260 (1995), Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-681 (Elsevier, N.Y., 1981), and Ni, *Xiandai Mianyixue*, 26(4): 265-268 (2006) regarding human-human hybridomas. Additional methods include those described, for example, in U.S. Pat. No. 7,189,826 regarding production of monoclonal human natural IgM antibodies from hybridoma cell lines. Human hybridoma technology (Trioma technology) is described in Vollmers and Brandlein, *Histology and Histopathology*, 20(3):927-937 (2005) and Vollmers and Brandlein, *Methods and Findings in Experimental and Clinical Pharmacology*, 27(3):185-91 (2005). Once desired monoclonal antibodies have been isolated from hybridomas, polynucleotides encoding them may be subcloned into a prokaryotic expression vector, and antibodies may be produced by expression in a prokaryotic host cell by any of the methods described herein.

(iii) Library-Derived Antibodies

Antibodies of the disclosure may be isolated by screening combinatorial libraries for antibodies with the desired activity or activities. For example, a variety of methods are known in the art for generating phage display libraries and screening such libraries for antibodies possessing the desired binding characteristics such as the methods described in Example 3. Additional methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348:552-554; Clackson et al., *Nature* 352: 624-628 (1991); Marks et al., *J. Mol. Biol.* 222: 581-597 (1992); Marks and Bradbury, in *Methods in Molecular Biology* 248:161-175 (Lo, ed., Human Press, Totowa, N.J., 2003); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132(2004).

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.,* 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self-antigens without any immunization as described by Griffiths et al., *EMBO J,* 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.,* 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

(iv) Chimeric, Humanized and Human Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA,* 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing SDR (a-CDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008). Human antibodies can be made, for example and without limitation, by expression in a prokaryotic host cell from a prokaryotic expression vector by any of the methods described herein.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

(v) Antibody Fragments

Antibody fragments may be generated by traditional means, such as enzymatic digestion, or by recombinant techniques. In certain circumstances there are advantages of using antibody fragments, rather than whole antibodies. The smaller size of the fragments allows for rapid clearance, and may lead to improved access to solid tumors. For a review of certain antibody fragments, see Hudson et al. (2003) *Nat. Med.* 9:129-134.

Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992); and Brennan et al., *Science,* 229:81 (1985)). However, these fragments can now be produced directly by recombinant host cells. Fab, Fv and ScFv antibody fragments can all be expressed in and secreted from *E. coli,* thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See *Antibody Engineering,* ed. Borrebaeck, supra. The antibody fragment may also be a "linear antibody", e.g., as described in U.S. Pat. No. 5,641,870, for example. Such linear antibodies may be monospecific or bispecific.

(vi) Multispecific Antibodies

Multispecific antibodies have binding specificities for at least two different epitopes, where the epitopes are usually from different antigens. While such molecules normally will only bind two different epitopes (i.e. bispecific antibodies, BsAbs), antibodies with additional specificities such as trispecific antibodies are encompassed by this expression when used herein. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

One approach known in the art for making bispecific antibodies is the "knobs-into-holes" or "protuberance-into-cavity" approach (see, e.g., U.S. Pat. No. 5,731,168). In this approach, two immunoglobulin polypeptides (e.g., heavy chain polypeptides) each comprise an interface. An interface of one immunoglobulin polypeptide interacts with a corresponding interface on the other immunoglobulin polypeptide, thereby allowing the two immunoglobulin polypeptides to associate. These interfaces may be engineered such that a "knob" or "protuberance" (these terms may be used interchangeably herein) located in the interface of one immunoglobulin polypeptide corresponds with a "hole" or "cavity" (these terms may be used interchangeably herein) located in the interface of the other immunoglobulin polypeptide. In some embodiments, the hole is of identical or similar size to the knob and suitably positioned such that when the two interfaces interact, the knob of one interface is positionable in the corresponding hole of the other interface. Without wishing to be bound to theory, this is thought to stabilize the heteromultimer and favor formation of the heteromultimer over other species, for example homomultimers. In some embodiments, this approach may be used to promote the heteromultimerization of two different immunoglobulin polypeptides, creating a bispecific antibody comprising two immunoglobulin polypeptides with binding specificities for different epitopes.

In some embodiments, a knob may be constructed by replacing a small amino acid side chain with a larger side chain. In some embodiments, a hole may be constructed by replacing a large amino acid side chain with a smaller side chain. Knobs or holes may exist in the original interface, or they may be introduced synthetically. For example, knobs or holes may be introduced synthetically by altering the nucleic acid sequence encoding the interface to replace at least one "original" amino acid residue with at least one "import" amino acid residue. Methods for altering nucleic acid sequences may include standard molecular biology techniques well known in the art. The side chain volumes of various amino acid residues are shown in the following table. In some embodiments, original residues have a small side chain volume (e.g., alanine, asparagine, aspartic acid, glycine, serine, threonine, or valine), and import residues for forming a knob are naturally occurring amino acids and may include arginine, phenylalanine, tyrosine, and tryptophan. In some embodiments, original residues have a large side chain volume (e.g., arginine, phenylalanine, tyrosine, and tryptophan), and import residues for forming a hole are naturally occurring amino acids and may include alanine, serine, threonine, and valine.

TABLE 1b

Properties of amino acid residues

| Amino Acid | One-letter abbreviation | Mass[a] (daltons) | Volume[b] ($Å^3$) | Accessible surface area[c] ($Å^2$) |
|---|---|---|---|---|
| Alanine (Ala) | A | 71.08 | 88.6 | 115 |
| Arginine (Arg) | R | 156.20 | 173.4 | 225 |
| Asparagine (Asn) | N | 114.11 | 117.7 | 160 |
| Aspartic Acid (Asp) | D | 115.09 | 111.1 | 150 |
| Cysteine (Cys) | C | 103.14 | 108.5 | 135 |
| Glutamine (Gln) | Q | 128.14 | 143.9 | 180 |
| Glutamic Acid (Glu) | E | 129.12 | 138.4 | 190 |
| Glycine (Gly) | G | 57.06 | 60.1 | 75 |
| Histidine (His) | H | 137.15 | 153.2 | 195 |
| Isoleucine (Ile) | I | 113.17 | 166.7 | 175 |
| Leucine (Leu) | L | 113.17 | 166.7 | 170 |
| Lysine (Lys) | K | 128.18 | 168.6 | 200 |
| Methionine (Met) | M | 131.21 | 162.9 | 185 |
| Phenylalanine (Phe) | F | 147.18 | 189.9 | 210 |
| Proline (Pro) | P | 97.12 | 122.7 | 145 |
| Serine (Ser) | S | 87.08 | 89.0 | 115 |
| Threonine (Thr) | T | 101.11 | 116.1 | 140 |
| Tryptophan (Trp) | W | 186.21 | 227.8 | 255 |
| Tyrosine (Tyr) | Y | 163.18 | 193.6 | 230 |
| Valine (Val) | V | 99.14 | 140.0 | 155 |

[a]Molecular weight of amino acid minus that of water. Values from Handbook of Chemistry and Physics, 43$^{rd}$ ed. Cleveland, Chemical Rubber Publishing Co., 1961.
[b]Values from A.A. Zamyatnin, Prog. Biophys. Mol. Biol. 24:107-123, 1972.
[c]Values from C. Chothia, J. Mol. Biol. 105:1-14, 1975. The accessible surface area is defined in FIGS. 6-20 of this reference.

In some embodiments, original residues for forming a knob or hole are identified based on the three-dimensional structure of the heteromultimer. Techniques known in the art for obtaining a three-dimensional structure may include X-ray crystallography and NMR. In some embodiments, the interface is the CH3 domain of an immunoglobulin constant domain. In these embodiments, the CH3/CH3 interface of human IgG$_1$ involves sixteen residues on each domain located on four anti-parallel β-strands. Without wishing to be bound to theory, mutated residues are preferably located on the two central anti-parallel β-strands to minimize the risk that knobs can be accommodated by the surrounding solvent, rather than the compensatory holes in the partner CH3 domain. In some embodiments, the mutations forming corresponding knobs and holes in two immunoglobulin polypeptides correspond to one or more pairs provided in the following table.

TABLE 2

Exemplary sets of corresponding knob-and hole-forming mutations

| CH3 of first immunoglobulin | CH3 of second immunoglobulin |
|---|---|
| T366Y | Y407T |
| T366W | Y407A |
| T366W | T366S:L368A:Y407V |
| F405A | T394W |
| Y407T | T366Y |

TABLE 2-continued

Exemplary sets of corresponding knob-and hole-forming mutations

| CH3 of first immunoglobulin | CH3 of second immunoglobulin |
|---|---|
| T366Y:F405A | T394W:Y407T |
| T366W:F405W | T394S:Y407A |
| F405W:Y407A | T366W:T394S |
| F405W | T394S |

Mutations are denoted by the original residue, followed by the position using the Kabat numbering system, and then the import residue (all residues are given in single-letter amino acid code).
Multiple mutations are separated by a colon.

In some embodiments, an immunoglobulin polypeptide comprises a CH3 domain comprising one or more amino acid substitutions listed in Table 2 above. In some embodiments, a bispecific antibody comprises a first immunoglobulin polypeptide comprising a CH3 domain comprising one or more amino acid substitutions listed in the left column of Table 2, and a second immunoglobulin polypeptide comprising a CH3 domain comprising one or more corresponding amino acid substitutions listed in the right column of Table 2. As a non-limiting example of a knob-and-hole-forming pair, in some embodiments, a bispecific antibody comprises a first immunoglobulin polypeptide comprising a CH3 domain comprising a T366W mutation, and a second immunoglobulin polypeptide comprising a CH3 domain comprising T366S, L368A, and Y407V mutations.

Each half-antibody can have either a knob (protuberance) or a hole (cavity) engineered into the heavy chain as described in U.S. Pat. No. 7,642,228. Briefly, a CH3 knob mutant can be generated first. A library of CH3 hole mutants can be then created by randomizing residues 366, 368 and 407 that are in proximity to the knob on the partner CH3 domain. In certain embodiments, the knob mutation comprises T366W, and the hole mutations comprise T366S, L368A and Y407V in an IgG1 or IgG4 backbone. Equivalent mutations in other immunoglobulin isotypes can be made by one skilled in the art. Further, the skilled artisan will readily appreciate that it is preferred that the two half-antibodies used for the bispecific antibody be of the same isotype.

Exemplary and non-limiting techniques for producing multispecific (e.g., bispecific) antibodies are provided in section III.

Antibodies with more than two valencies are contemplated. For example, trispecific antibodies can be prepared. Tuft et al. *J. Immunol.* 147: 60 (1991).

In some embodiments, the two chain protein is a part of a multispecific antibody or a bispecific antibody. A multispecific antibody or a bispecific antibody may contain two or more monovalent antibodies of the present disclosure.

Figure 5:
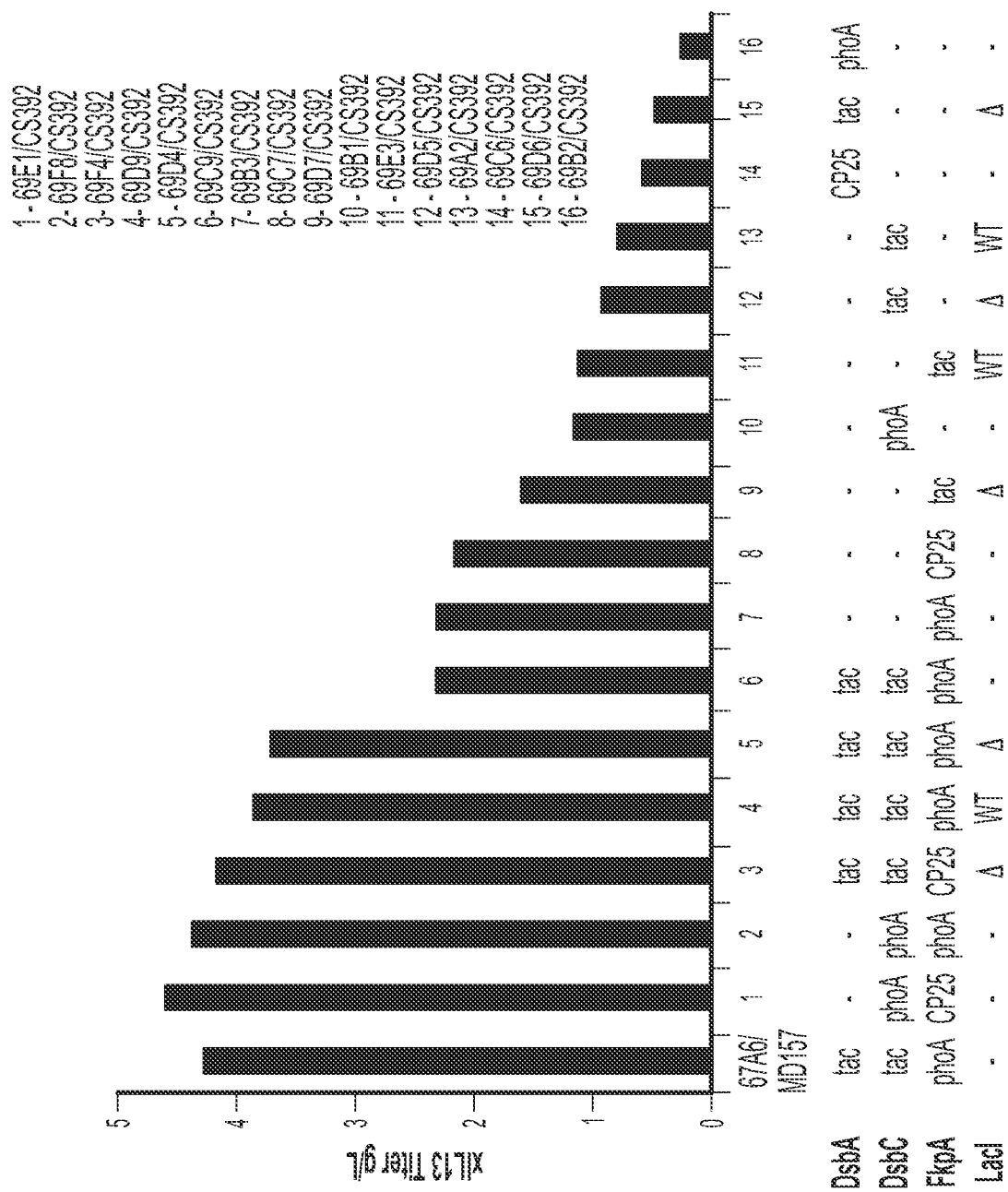
FIG. 5 shows xIL13 titer (g/L) produced by strains with the indicated chromosomally engineered pairs of plasmid and native chaperone locus. 67A6/MD157 refers to a strain without chromosomal engineering and with the MD157 plasmid expressing the indicated chaperones under the indicated promoter (see FIG. 1 for a diagram of the MD157 plasmid).
Figure 6A:
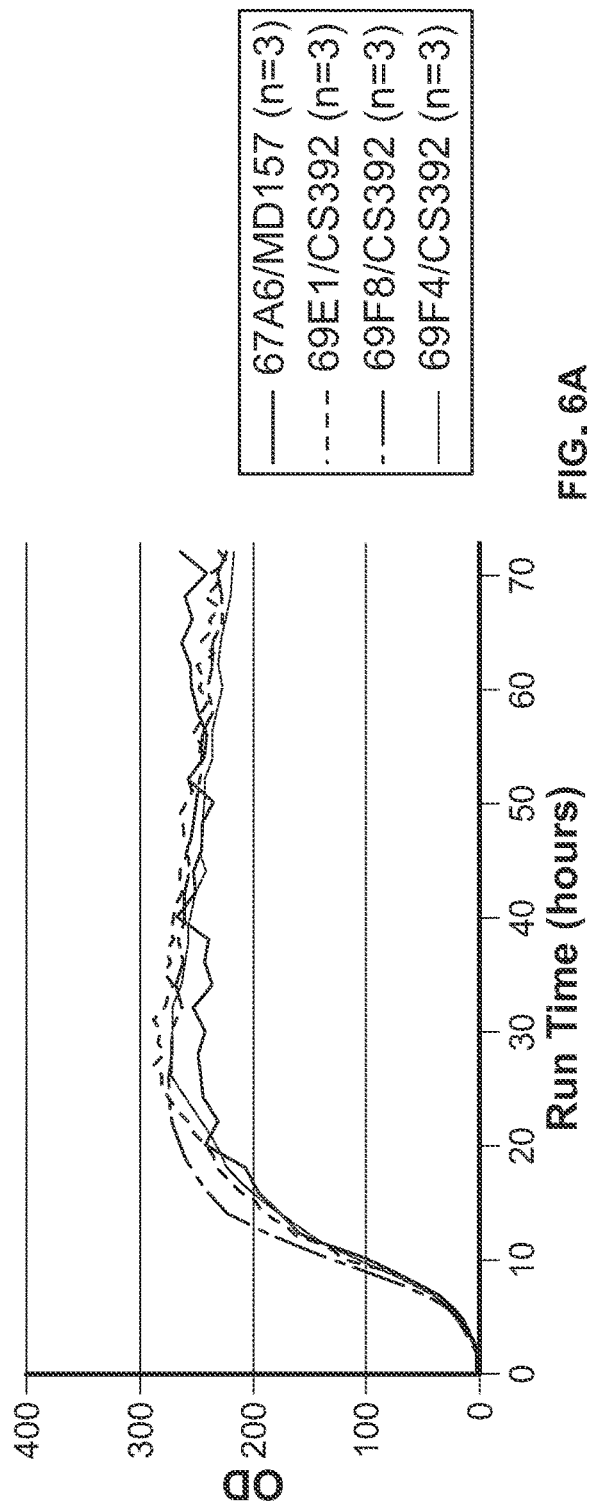
FIGS. 6A & 6B show the optical density (OD.
Figure 6B:
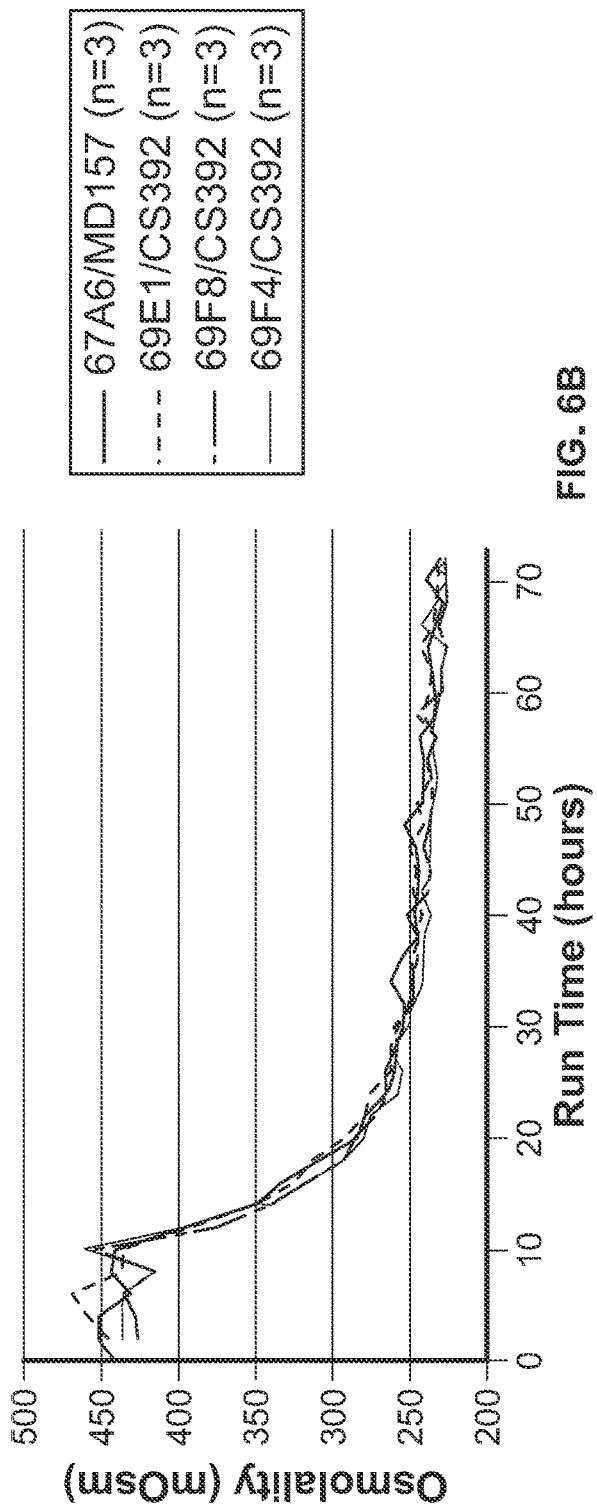
Figure 8A:
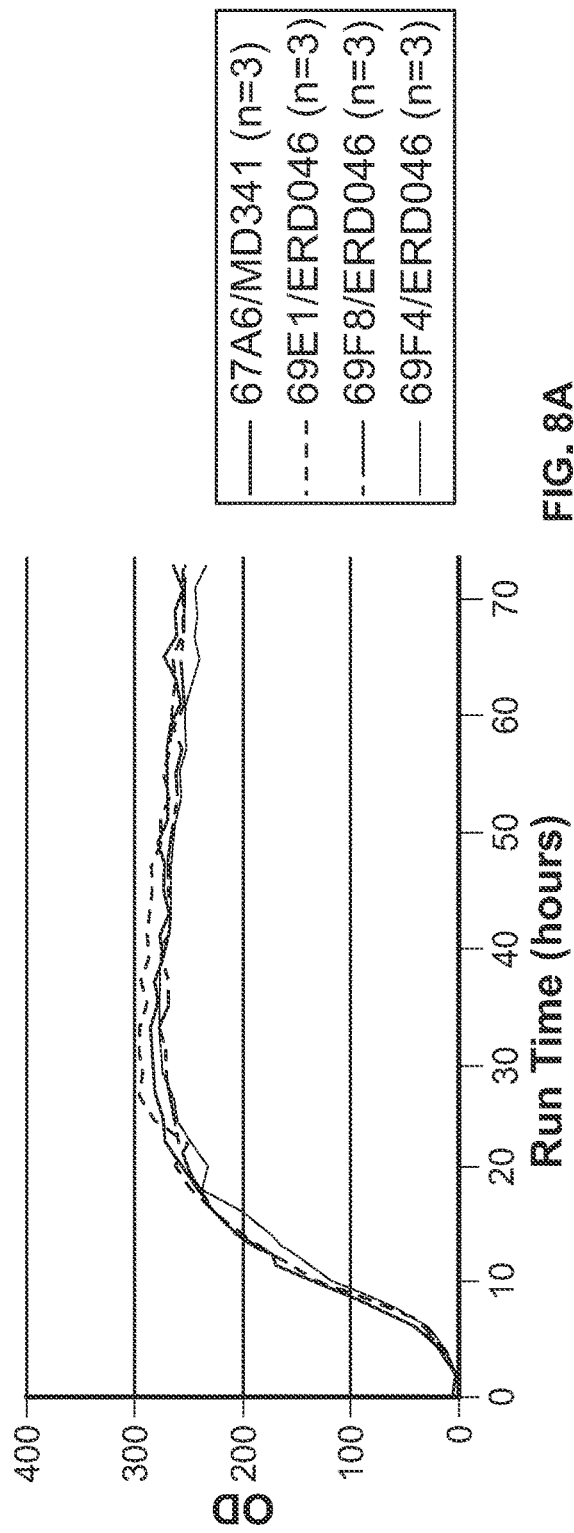
FIGS. 8A & 8B show the optical density (OD.
Figure 8B:
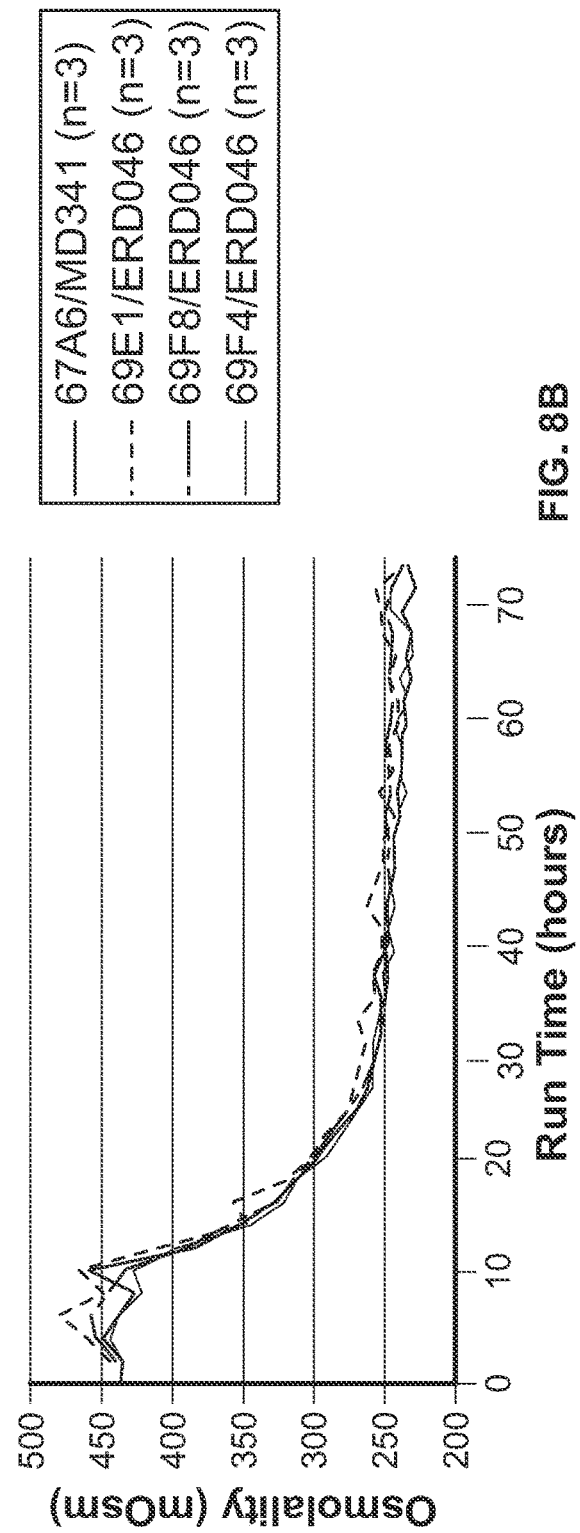

In some embodiments, the first antigen binding domain of the bispecific antibody comprises one or more heavy chain constant domains, wherein the one or more heavy chain constant domains are selected from a first CH1 ($CH1_1$) domain, a first CH2 ($CH2_1$) domain, a first CH3 ($CH3_1$) domain; and the second antigen binding domain of the bispecific antibody comprises one or more heavy chain constant domains, wherein the one or more heavy chain constant domains are selected from a second CH1 ($CH1_2$) domain, second CH2 ($CH2_2$) domain, and a second CH3 ($CH3_2$) domain. In some embodiments, at least one of the one or more heavy chain constant domains of the first antigen binding domain is paired with another heavy chain constant domain of the second antigen binding domain. In some embodiments, the $CH3_1$ and $CH3_2$ domains each comprise a protuberance or cavity, and wherein the protuberance or cavity in the $CH3_1$ domain is positionable in the cavity or protuberance, respectively, in the $CH3_2$ domain. In some embodiments, the $CH3_1$ and $CH3_2$ domains meet at an interface between said protuberance and cavity. Exemplary sets of amino acid substitutions in $CH3_1$ and $CH3_2$ domains are shown in Table 2 herein. In some embodiments, the $CH2_1$ and $CH2_2$ domains each comprise a protuberance or cavity, and wherein the protuberance or cavity in the $CH2_1$ domain is positionable in the cavity or protuberance, respectively, in the $CH2_2$ domain. In some embodiments, the $CH2_1$ and $CH2_2$ domains meet at an interface between said protuberance and cavity. In some embodiments, the $CH3_1$ and/or $CH3_2$ domain of an IgG contain one or more amino acid substitutions at residues selected from the group consisting of 347, 349, 350, 351, 366, 368, 370, 392, 394, 395, 398, 399, 405, 407, and 409 according to the amino acid numbering as shown in FIG. 5 of the U.S. Pat. No. 8,216,805. In some embodiments, the protuberance comprises one or more introduced residues selected from the group consisting of arginine (R) residue, phenylalanine (F) residue, tyrosine (Y) residue, and tryptophan (W) residue. In some embodiments, the cavity comprises one or more introduced residues selected from the group consisting of alanine (A) residue, serine (S) residue, threonine (T) residue, and valine (V) residue. In some embodiments, the CH3 and/or CH2 domains are from an IgG (e.g., IgG1 subtype, IgG2 subtype, IgG2A subtype, IgG2B subtype, IgG3, subtype, or IgG4 subtype). In some embodiments, one CH3 domain of the bispecific antibody comprises amino acid substitution T366Y, and the other CH3 domain comprises amino acid substitution Y407T. In some embodiments, one CH3 domain comprises amino acid substitution T366W, and the other CH3 domain comprises amino acid substitution Y407A. In some embodiments, one CH3 domain comprises amino acid substitution F405A, and the other CH3 domain comprises amino acid substitution T394W. In some embodiments, one CH3 domain comprises amino acid substitutions T366Y and F405A, and the other CH3 domain comprises amino acid substitutions T394W and Y407T. In some embodiments, one CH3 domain comprises amino acid substitutions T366W and F405W, and the other CH3 domain comprises amino acid substitutions T394S and Y407A. In some embodiments, one CH3 domain comprises amino acid substitutions F405W and Y407A, and the other CH3 domain comprises amino acid substitutions T366W and T394S. In some embodiments, one CH3 domain comprises amino acid substitution F405W, and the other CH3 domain comprises amino acid substitution T394S. The mutations are denoted by the original residue, followed by the position using the Kabat numbering system, and then the import residues. See also numbering in FIG. 5 of U.S. Pat. No. 8,216,805.

(vii) Single-Domain Antibodies

In some embodiments, an antibody of the disclosure is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B 1). In one embodiment, a single-domain antibody consists of all or a portion of the heavy chain variable domain of an antibody.

(viii) Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

(ix) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 3

Exemplary Substitutions.

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
 a. hydrophobic: Norleucine, Met, Ala, Val, Leu, Ile;
 b. neutral hydrophilic: Cys, Ser, Thr, Asn, Gln;
 c. acidic: Asp, Glu;
 d. basic: His, Lys, Arg;
 e. residues that influence chain orientation: Gly, Pro;
 f. aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science,* 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g., for ADEPT) or a polypeptide which increases the serum half-life of the antibody.

(x) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the disclosure contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express Fc(RI, Fc(RII and Fc(RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. *Proc. Nat'l Acad. Sci. USA* 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues). In an exemplary embodiment, the antibody comprising the following amino acid substitutions in its Fc region: 5298 A, E333A, and K334 A.

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.)). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. Nos. 5,648,260; 5,624,821; and WO 94/29351 concerning other examples of Fc region variants.

(xi) Antibody Derivatives

The antibodies of the disclosure can be further modified to contain additional nonproteinaceous moieties that are known in the art and readily available. In certain embodiments, the moieties suitable for derivatization of the antibody are water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

III. Methods of Production

Provided herein are methods of producing a polypeptide comprising two chains (e.g., a two-chain polypeptide) in a prokaryotic host cell of the present disclosure. In some embodiments, the methods comprise: culturing a host cell of the present disclosure to express the two chains of the polypeptide in a culture medium under conditions suitable for expression of the two chains of the polypeptide, whereby upon expression the two chains fold and assemble to form a biologically active polypeptide in the host cell; and recovering the biologically active polypeptide from the host cell.

Any of the host cells of the present disclosure (e.g., as described in section II) may find use in the methods of the present disclosure. For example, in some embodiments, the host cell comprises one or more extra-chromosomal polynucleotide(s) of the present disclosure and one or more translational units of the present disclosure (e.g., operably linked to a promoter and present on the host cell chromosome in a non-native combination). In some embodiments, the host cell comprises a first polynucleotide comprising a first translational unit encoding a first chain of the polypeptide (part of an extra-chromosomal polynucleotide); a second polynucleotide comprising a second translational unit encoding a second chain of the polypeptide (part of an extra-chromosomal polynucleotide); and a third polynucleotide comprising a third translational unit (part of the host cell chromosome) encoding a chaperone protein (e.g., a peptidyl-prolyl isomerase or protein disulfide oxidoreductase of the present disclosure) and in operable combination with a promoter of the present disclosure in a non-native combination. In some embodiments, the host cell comprises a first polynucleotide comprising a first translational unit encoding a first chain of the polypeptide (part of an extra-chromosomal polynucleotide); a second polynucleotide comprising a second translational unit encoding a second chain of the polypeptide (part of an extra-chromosomal polynucleotide); a third polynucleotide comprising a third translational unit (part of the host cell chromosome) encoding a protein disulfide oxidoreductase of the present disclosure and in operable combination with a promoter of the present disclosure in a non-native combination; and a fourth polynucleotide comprising a fourth translational unit (part of the host cell chromosome) encoding a peptidyl-prolyl isomerase of the present disclosure and in operable combination with a promoter of the present disclosure in a non-native combination. In some embodiments, the host cell comprises a first polynucleotide comprising a first translational unit encoding a first chain of the polypeptide (part of an extra-chromosomal polynucleotide); a second polynucleotide comprising a second translational unit encoding a second chain of the polypeptide (part of an extra-chromosomal polynucleotide); a third polynucleotide comprising a third translational unit (part of the host cell chromosome) encoding a protein disulfide oxidoreductase of the present disclosure and in operable combination with a promoter of the present disclosure in a non-native combination; a fourth polynucleotide comprising a fourth translational unit (part of the host cell chromosome) encoding a peptidyl-prolyl isomerase of the present disclosure and in operable combination with a promoter of the present disclosure in a non-native combination; and a fifth translational unit (part of the host cell chromosome) encoding a second protein disulfide oxidoreductase of the present disclosure and in operable combination with a promoter of the present disclosure in a non-native combination. In some embodiments of any of the above embodiments, the host cell further comprises a translational unit encoding a third chain of the two-chain protein (part of an extra-chromosomal polynucleotide).

In some embodiments, a host cell is cultured to express the two chains of a polypeptide, where upon expression the two chains fold and assemble to form a biologically active polypeptide in the host cell. As used herein, two chain folding and assembly may refer to any or all steps that promote the ultimate adoption of proper three-dimensional two chain protein conformation, two chain protein assembly, or both. Folding and assembly may refer to the folding and assembly of each chain into its proper conformation and folding, or it may refer to the folding and assembly of the complex created by the intermolecular linkage of two protein chains. Similarly, each chain may fold and assemble to form a biologically active polypeptide, or the complex created by the intermolecular linkage of two protein chains may fold and assemble to form, as a whole, a biologically active polypeptide.

A biologically active polypeptide may refer to any polypeptide that is able to carry out a function ascribed to the polypeptide. Functions of biologically active polypeptides may include, without limitation, proper folding or assembly, binding or other interaction with another macromolecule, and enzymatic activity. By way of illustration, a biologically active antibody may refer to an antibody that is able to carry out at least one function ascribed to antibodies, including without limitation binding to an epitope or possessing a property of an antibody Fc region, as described in further detail herein.

Antibodies may be produced using recombinant methods. For recombinant production of an anti-antigen antibody, nucleic acid encoding the antibody is isolated and inserted into a replicable vector for further cloning (amplification of the DNA) or for expression. DNA encoding the antibody may be readily isolated and sequenced using conventional procedures (e.g., by using oligonucleotide probes that are capable of binding specifically to genes encoding the heavy and light chains of the antibody). Many vectors are available. The vector components generally include, but are not limited to, one or more of the following: a signal sequence, an origin of replication, one or more marker genes, an enhancer element, a promoter, and a transcription termination sequence, e.g., as described supra.

Multispecific (e.g., Bispecific) Antibody Production

Certain aspects of the present disclosure relate to methods of producing a bispecific antibody (e.g., comprising a first half antibody capable of binding a first antigen and a second half antibody capable of binding a second antigen, where the first and second antigens are optionally different). In some embodiments, the methods comprise producing a first half antibody as described herein, wherein the first half antibody comprises a heavy chain and a light chain encoded by a translational unit of the present disclosure (e.g., part of one or more extra-chromosomal polynucleotide(s)); and producing a second half antibody as described herein, wherein the second half antibody comprises a heavy chain and a light chain encoded by a translational unit of the present disclosure (e.g., part of one or more extra-chromosomal polynucleotide(s)). In some embodiments, one of the first and the second half-antibodies comprises at least one knob-forming mutation of the present disclosure, and the other of the first and the second half-antibodies comprises at least one hole-forming mutation of the present disclosure. In some embodiments, the methods further comprise combining, in a reducing condition, the first half antibody with the second half antibody to produce a bispecific antibody. Exemplary methods for half antibody production and bispecific antibody assembly are provided infra.

Polynucleotides encoding modified immunoglobulin polypeptides with one or more corresponding knob- or hole-forming mutations may be expressed and purified using standard recombinant techniques and cell systems known in the art. See, e.g., U.S. Pat. Nos. 5,731,168; 5,807,706; 5,821,333; 7,642,228; 7,695,936; 8,216,805; U.S. Pub. No. 2013/0089553; and Spiess et al., Nature Biotechnology 31: 753-758, 2013. Modified immunoglobulin polypeptides may be produced using prokaryotic host cells, such as *E. coli*.

Corresponding knob- and hole-bearing immunoglobulin polypeptides may be expressed in host cells in co-culture and purified together as a heteromultimer, or they may be expressed in single cultures, separately purified, and assembled in vitro. In some embodiments, two strains of bacterial host cells (one expressing an immunoglobulin polypeptide with a knob, and the other expressing an immunoglobulin polypeptide with a hole) are co-cultured using standard bacterial culturing techniques known in the art. In some embodiments, the two strains may be mixed in a specific ratio, e.g., so as to achieve equal expression levels in culture. In some embodiments, the two strains may be mixed in a 50:50, 60:40, or 70:30 ratio. After polypeptide expression, the cells may be lysed together, and protein may be extracted. Standard techniques known in the art that allow for measuring the abundance of homo-multimeric vs. hetero-multimeric species may include size exclusion chromatography. In some embodiments, each modified immunoglobulin polypeptide is expressed separately using standard recombinant techniques, recovered, and assembled together in vitro. As described in greater detail below, assembly may be achieved, for example, by purifying each modified immunoglobulin polypeptide, mixing and incubating them together in equal mass, reducing disulfides (e.g., by treating with dithiothreitol), concentrating, and reoxidizing the polypeptides. Formed bispecific antibodies may be purified using standard techniques including cation-exchange chromatography and measured using standard techniques including size exclusion chromatography. For a more detailed description of these methods, see Speiss et al., *Nat Biotechnol* 31:753-8, 2013.

Half-antibodies containing either the knob or hole mutations are generated in separate cultures by expressing the heavy and light chains constructs in a bacterial host cell, (e.g., *E. coli*). Each half-antibody can be purified separately by Protein A affinity chromatography. Clarified cell extracts from the knob and hole half-antibody can be purified by a HiTrap MAB SELECT SURE™ column. Protein A purified half antibodies with different specificity can be assembled to form a bispecific antibody in a redox reaction in vitro in the presence of a reducing agent.

Any suitable methods can be used to prepare a desired reducing condition. For example, a desired reducing condition can be prepared by adding a reductant/reducing agent to the reaction (such as an assembly mixture of the invention). Suitable reductants include without limitation dithiothreitol (DTT), tris(2-carboxyethyl)phosphine (TCEP), thioglycolic acid, ascorbic acid, thiol acetic acid, glutathione (GSH), Beta-MercaptoEthylAmine, cysteine/cystine, GSH/glutathione disulfide (GSSG), cysteamine/cystamine, glycylcysteine, and beta-mercaptoethanol, preferably GSH. In certain particular embodiments, the reductant is a weak reductant including without limitation GSH, Beta-MercaptoEthylAmine, cysteine/cystine, GSH/GSSG, cysteamine/cystamine, glycylcysteine, and beta-mercaptoethanol, preferably GSH. In certain preferred embodiments, the reductant is GSH. In certain embodiments, the reductant is not DTT. It is within the ability of one of ordinary skill in the art to select suitable reductants at suitable concentrations and under suitable experimental conditions to achieve in a reaction the desired reducing condition. For example, 10 mM L-reduced glutathione in a solution with a bispecific antibody protein concentration of 10 g/L at 20° C. will result in a starting redox potential of about −400 mV. For example, glutathione added to an assembly mixture creates a weakly reducing condition that is advantageous for knob-into-hole bispecific assembly. Other reductants in a similar class such as BMEA (Beta-MercaptoEthylAmine) may have a similar effect. See WO2013/055958, incorporated herein by reference in its entirety. The reducing condition of the reaction can be estimated and measured using any suitable methods known in the art. For example, the reducing condition can be measured using a resazurin indicator (discolorization from blue to colorless in reducing conditions). For more precise measurement, a redox-potential meter (such as an ORP Electrode made by BROADLEY JAMES®) can be used.

In certain particular embodiments, the reducing condition is a weak reducing condition. The term "weak reductant" or "weak reducing condition" as used herein refers to a reducing agent or a reducing condition prepared by the reducing agent having a negative oxidation potential at 25° C. The oxidation potential of the reductant is preferably between −50 to −600 mV, −100 to −600 mV, −200 to −600 mV, −100 to −500 mV, −150 to −300 mV, more preferably between about −300 to −500 mV, most preferably about −400 mV, when the pH is between 7 and 9, and the temperature is between 15° C. and 39° C. One skilled in the art will be able to select suitable reductants for preparing a desired reducing condition. The skilled researcher will recognize that a strong reductant, i.e., one that has a more negative oxidation potential than above mentioned reductants for the same concentration, pH and temperature, may be used at a lower concentration. In a preferred embodiment, the proteins will be able to form disulfide bonds in the presence of the reductant when incubated under the above-recited conditions. Examples of a weak reductant include without limitation glutathione, Beta-MercaptoEthylAmine, cystine/cysteine, GSH/GSSG, cysteamine/cystamine, glycylcysteine, and beta-mercaptoethanol. In certain embodiments, an oxidation potential similar to that of 200× molar ratio of GSH:Antibody can be used as a point of reference for a weakly reducing condition at which efficient assembly using other reductants can be expected.

Glutathione concentrations can be expressed in terms of molarity or in terms of molar ratio or molar excess with respect to the amount of the half-antibodies present in the assembly mixture. Using a target molar ratio of reductant controls for the protein concentration in the assembly mixture; this prevents over reducing or under reducing as a result of variable protein concentrations. In certain other embodiments, the reductant is added to the assembly mixture in 2-600×, 2-200×, 2-300×, 2-400×, 2-500×, 2-20×, 2-8×, 20-50×, 50-600×, 50-200×, or 100-300× molar excess, preferably 50-400×, more preferably 100-300×, and most preferably 200×, molar excess with respect to the total amount of the half antibodies. In certain embodiments, the assembly mixture has a pH of between 7 and 9, preferably pH 8.5.

In certain embodiments, the cultures of the first half antibody and second half antibody can be combined and subsequently lysed in the combined cultures. The released first half antibody and second half antibody in the combination can form a bispecific antibody in a reducing condition. See WO 2011/133886, incorporated herein by reference in its entirety.

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is typical to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology*, 121:210 (1986).

According to another approach described in WO96/27011, the interface between a pair of antibody molecules can be engineered to maximize the percentage of heterodimers which are recovered from recombinant cell culture. One interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab)$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217-225 (1992) describe the production of a fully humanized bispecific antibody F(ab')$_2$ molecule. Each Fab' fragment was separately secreted from *E. coli* and subjected to directed chemical coupling in vitro to form the bispecific antibody.

Various techniques for making and isolating bispecific antibody fragments directly from recombinant cell culture have also been described. For example, bispecific antibodies have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al, *J. Immunol*, 152:5368 (1994).

Another technique for making bispecific antibody fragments is the "bispecific T cell engager" or BiTE® approach (see, e.g., WO2004/106381, WO2005/061547, WO2007/042261, and WO2008/119567). This approach utilizes two antibody variable domains arranged on a single polypeptide. For example, a single polypeptide chain includes two single chain Fv (scFv) fragments, each having a variable heavy chain ($V_H$) and a variable light chain ($V_L$) domain separated by a polypeptide linker of a length sufficient to allow intramolecular association between the two domains. This single polypeptide further includes a polypeptide spacer sequence between the two scFv fragments. Each scFv recognizes a different epitope, and these epitopes may be specific for different cell types, such that cells of two different cell types are brought into close proximity or tethered when each scFv is engaged with its cognate epitope. One particular embodiment of this approach includes a scFv recognizing a cell-surface antigen expressed by an immune cell, e.g., a CD3 polypeptide on a T cell, linked to another scFv that recognizes a cell-surface antigen expressed by a target cell, such as a malignant or tumor cell.

As it is a single polypeptide, the bispecific T cell engager may be expressed using any prokaryotic cell expression system known in the art. However, specific purification techniques (see, e.g., EP1691833) may be necessary to separate monomeric bispecific T cell engagers from other multimeric species, which may have biological activities other than the intended activity of the monomer. In one exemplary purification scheme, a solution containing secreted polypeptides is first subjected to a metal affinity chromatography, and polypeptides are eluted with a gradient of imidazole concentrations. This eluate is further purified using anion exchange chromatography, and polypeptides are eluted using with a gradient of sodium chloride concentrations. Finally, this eluate is subjected to size exclusion chromatography to separate monomers from multimeric species.

Selection and Transformation of Host Cells

Two chain proteins such as full length antibodies or half antibodies, antibody fusion proteins, one-armed antibodies, and antibody fragments can be produced in bacteria, in particular when glycosylation and Fc effector function are not needed, such as when the therapeutic antibody is conjugated to a cytotoxic agent (e.g., a toxin) that by itself shows effectiveness in tumor cell destruction. Full length antibodies have greater half-life in circulation. Production in E. coli is faster and more cost efficient. For expression of antibody fragments and polypeptides in bacteria, see, e.g., U.S. Pat. No. 5,648,237 (Carter et. al.), U.S. Pat. No. 5,789,199 (Joly et al.), U.S. Pat. No. 5,840,523 (Simmons et al.), which describes translation initiation region (TIR) and signal sequences for optimizing expression and secretion. See also Charlton, Methods in Molecular Biology, Vol. 248 (B. K. C. Lo, ed., Humana Press, Totowa, N.J., 2003), pp. 245-254, describing expression of antibody fragments in E. coli. After expression, the antibody may be isolated from the E. coli cell paste in a soluble fraction and can be purified through, e.g., a protein A or G column depending on the isotype. Final purification can be carried out similar to the process for purifying antibody expressed e.g., in CHO cells.

Host cells are transformed with the expression or cloning vectors of the present disclosure for two chain protein production and cultured in conventional nutrient media modified as appropriate for inducing promoters, selecting transformants, or amplifying the genes encoding the desired sequences.

Culturing the Host Cells

Host cells of the present disclosure may be cultured in a variety of media. "Culture medium" as used herein refers to any composition or broth that supports the growth of the bacteria of the present disclosure. Suitable culture media may be liquid or solid and contain any nutrients, salts, buffers, elements, and other compounds that support the growth and viability of cells. Common nutrients of a culture medium may include sources of nitrogen, carbon, amino acids, carbohydrates, trace elements, vitamins, and minerals. These nutrients may be added as individual components (as in a defined culture medium) or as constituents of a complex extract (for example, yeast extract). A culture medium may be nutrient-rich to support rapid growth or minimal to support slower growth. A culture medium may also contain any agent used to inhibit the growth of or kill contaminating organisms (e.g., an antibiotic). A culture medium may also contain any compound used to control the activity of an inducible promoter or enzyme (as one example, IPTG may be included to induce expression of any polynucleotides controlled by a lac operon or functionally similar promoter). Many examples of suitable culture media are well known in the art and include without limitation M9 medium, Lysogeny Broth (LB), Terrific Broth (TB), NZY broth, SOB medium, and YT broth.

Any of these media may be supplemented as necessary with salts (such as sodium chloride, calcium, magnesium, and phosphate), buffers (such as HEPES), nucleotides (such as adenosine and thymidine), antibiotics, antimycotics, trace elements (defined as inorganic compounds usually present at final concentrations in the micromolar range), glucose, and/or an appropriate energy source. Typical ingredients found in a prokaryotic cell culture medium include yeast extract, salts (e.g, NaCl), tryptone, buffers (e.g., phosphate buffer), glycerol, and so forth. Any other necessary supplements may also be included at appropriate concentrations that would be known to those skilled in the art. The culture conditions, such as temperature, pH, and the like, are those previously used with the prokaryotic host cell selected for expression, and will be apparent to the ordinarily skilled artisan.

Purification of Biologically Active Polypeptide

Certain aspects of the present disclosure relate to recovering a biologically active polypeptide from a host cell. Typically recovering (the terms "purifying" or "purification" may be used interchangeably herein) a biologically active polypeptide of the present disclosure involves isolating the polypeptide from the host cell (or cell culture medium if the polypeptide is excreted into the medium) and purifying the polypeptide from other associated macromolecules, e.g., cellular debris and other polypeptides. Numerous techniques for purifying a variety of proteins from a variety of host cell compartments are known in the art (see, e.g., Evans, Jr., TC and Xu M Q (eds.) Heterologous Gene Expression in E. coli (2011) Methods in Molecular Biology Vol 705, Humana Press). Exemplary techniques are described below, but these are included for illustrative purposes only to supplement the understanding of the skilled artisan and are in no way meant to be limiting.

When using recombinant techniques, two chain proteins such as secretory proteins can be produced intracellularly, in the periplasmic space, or directly secreted into the medium. If the secretory protein is produced intracellularly, as a first step, the particulate debris, either host cells or lysed fragments, are removed, for example, by centrifugation or ultrafiltration.

In some embodiments, the secretory protein is recovered from the periplasm of the host cell. Carter et al., Bio/Technology 10:163-167 (1992) describe a procedure for isolating secretory proteins which are secreted to the periplasmic space of E. coli. Briefly, cell paste is thawed in the presence of sodium acetate (pH 3.5), EDTA, and phenylmethylsulfonylfluoride (PMSF) over about 30 min. Cell debris can be removed by centrifugation. Where the secretory protein is secreted into the medium, supernatants from such expression systems are generally first concentrated using a commercially available protein concentration filter, for example, an AMICON® or MILLIPORE® PELLICON® ultrafiltration unit. A protease inhibitor such as PMSF may be included in any of the foregoing steps to inhibit proteolysis and antibiotics may be included to prevent the growth of adventitious contaminants.

The secretory protein composition prepared from the cells can be purified using, for example, hydroxylapatite chromatography, hydrophobic interaction chromatography, gel electrophoresis, dialysis, and affinity chromatography, with affinity chromatography being among one of the typically preferred purification steps. With regard to antibodies, the suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Meth. 62:1-13 (1983)). Protein G is recommended for all mouse isotypes and for human γ3 (Guss et al., EMBO J. 5:15671575 (1986)). The matrix to which the affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_H3$ domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered. One of skill in the art will recognize that many of these techniques useful for antibody recovery may readily be applied to recover other two chain proteins, such as secretory proteins.

EXAMPLES

The disclosure will be more fully understood by reference to the following examples. They should not, however, be construed as limiting the scope of the disclosure. It is understood that the examples and embodiments described herein are for illustrative purposes only and that various modifications or changes in light thereof will be suggested to persons skilled in the art and are to be included within the spirit and purview of this application and scope of the appended claims.

Example 1: Engineering E. coli Strains with Chromosomally Integrated Promoters that Control the Expression of Chaperones DsbA, DsbC, and FkpA The overexpression of the chaperones DsbA, DsbC, and FkpA from plasmids can improve antibody-based product production in bacterial culture. However, expression of these chaperones from plasmids has several disadvantages. For example, such an approach requires the development and tuning of expression plasmids for each new product. Large plasmid size can also in some cases result in lower product titer. In addition, plasmids are typically present at 10-15 copies per cell, resulting in high levels of overexpression that can necessitate downstream purification step(s) to remove chaperone proteins (e.g., FkpA) from the product. In some cases, the same product titer could be achieved with lower expression levels of one or more chaperones.

Here, the native promoters of dsbA, dsbC, and fkpA within the E. coli genome were exchanged with the promoters phoA, tac, and CP25 in non-native combinations to create engineered strains that chromosomally overexpress chaperones. These strains were investigated for use in producing two half-antibodies (anti-IL13 half-antibody, referred to herein as "xIL13," and AF2), a one-armed antibody (MetMAb), and an antibody Fab fragment (anti-VEGF antibody fragment).
Methods
Vector Construction
Vectors which express chaperones and either xIL13 (MD157) or AF2 (MD341) were constructed as described in WO2016073791 (see, e.g., paragraphs 278 and 279, 281-284, 285-288).
Strain Engineering
The phoA (see Wanner B. L. (1990) *Colloqium Mosbach, Mol. Basis Bact. Metab. P.* 41), tac (see de Boer H. A. et al. (1983) *PNAS* 80, P. 21-5), and CP25 (see Jensen P. R. and Hammer K. (1998) *Appl. Environ. Microbiol.* 64, P. 82-87) promoters were integrated into the E. coli genome to replace the native promoters of dsbA, dsbC, and fkpA. These promoter modifications were carried out through allelic exchange (see, e.g., Bass, S. et al. (1996) *J Bacteriol.* 178:1154-1161 and Innes, D. et al. (2001) *Microbiology* 147:1887-1896).

Briefly, a pS1080-based suicide vector was constructed with NEBuilder® HiFi DNA Assembly Master Mix (Gibson Assembly) to include the promoter of interest, flanked on each side by 500 base pairs of homologous sequence matching the desired region of insertion in the E. coli genome. After sequencing to confirm, bacteriophages M13 and P1 were used to infect strain 48C8 with the plasmid sequence and transduce the introduced sequence to the strain of interest (see, e.g., Nakashima, N. and Miyazaki, K. (2014) *Int. J Mol. Sci.* 15:2773-2793). The promoter as taken from the source plasmid replaced the intergenic region upstream of the chaperone. This resulted in a replacement of the native promoters of dsbA, dsbC, and fkpA within the E. coli genome with phoA, tac, and/or CP25 promoters from the pS1080 suicide vector. Modifications to the lacI gene were also made in order to further augment expression from the tac promoter. Vial lots of the resulting strains were produced and stored at −80° C.
Shake Flask Cultures and Fermentation Processes
Engineered strains (see Table B) were cultured in standard shake flask cultures (Sh. Fl.) and 10 liter fermentations (10 L). The 10 liter fermentations were performed as described in WO2016073791 (see, e.g., paragraphs 289-292). Strains 67A6 and 64B4, which only contain chaperones expressed from their native promoters, were used as negative controls (i.e., Sh.F1. (−) and Ambr (−)). For positive controls, these strains were transformed with plasmids expressing DsbA, DsbC, and FkpA (see Table A) (i.e., Sh.F1. (+), Ambr (+), and 10 L (+)).
Electrophoresis, Western Blot, and HPLC Analysis
DsbA, DsbC, and FkpA relative concentrations were measured by Western blot. xIL13, AF2, MetMAb, and anti-VEGF antibody fragment concentrations were measured by reverse-phase HPLC. Electrophoresis, Western blot, and HPLC analysis methods were performed as described in WO2016073791 (see, e.g., paragraphs 293-299).
Results
Vectors were constructed for the overexpression of the antibody-based products xIL13, AF2, MetMAb, and the anti-VEGF antibody fragment in E. coli. Representative plasmid maps for vectors that express xIL13 are shown in FIG. 1. Each vector contains a gene encoding xIL13, AF2, MetMAb, or the anti-VEGF antibody fragment and either (1) no chaperone genes (e.g., FIG. 1, right), or (2) combinations of dsbA, dsbC, and fkpA (e.g., FIG. 1, left), as detailed in Table A below. Strains containing these vectors can be used as positive controls when evaluating protein expression in engineered strains.

TABLE A

Vectors used for strain evaluations.

| Antibody product expressed | Plasmids without chaperone genes | Plasmids containing chaperone genes | | | |
|---|---|---|---|---|---|
| | | Name | dsbA promoter | dsbC promoter | fkpA promoter |
| xIL13 | CS392 | MD157 | tac | tac | phoA |
| AF2 | ERD046 | MD341 | tac | tac | phoA |
| MetMAb | p186 | pOA5D5.3630 | tac | tac | — |
| anti-VEGF | HSK117 | HSK117 | — | — | — |

— indicates the absence of the indicated chaperone gene.

In addition, seventeen strains were constructed for the overexpression of one or more of the periplasmic chaperones DsbC, DsbA, and FkpA by exchanging the native promoters of these chaperones in the *E. coli* genome with the tac, phoA, and CP25 promoters. The lacI background of the strains was also engineered to further augment expression from the tac promoter by either deleting lacI (ΔlacI and ΔlacI::kan), inserting a wild-type copy of lacI (lacI⁺ or lacI WT), or leaving the original lacI$^Q$ mutation of the parent strain intact. The lacI gene product represses expression from the tac promoter, thus a deletion of lacI leads to higher expression from the tac promoter. The lacI$^Q$ mutation leads to increased levels of transcription of lacI, leading to stronger repression of the tac promoter (see Calos (1978) *Nature* 274, P. 762-765). Additionally, the tac promoter can be induced with IPTG. Table B lists the engineered strains, indicating the engineered promoter modifications in addition to the lacI gene modifications.

TABLE B

Strains constructed for chromosomal expression of DsbC, DsbA, and FkpA.

| Number/Location | Promoter-dsbC | Promoter-dsbA | Promoter-fkpA | lacI Background[a] |
|---|---|---|---|---|
| 69A2 | tac | — | — | — |
| 69B1 | phoA | — | — | — |
| 69B2 | — | phoA | — | — |
| 69B3 | — | — | phoA | — |
| 69C6 | — | CP25 | — | — |
| 69C7 | — | — | CP25 | — |
| 69C9 | tac | tac | phoA | — |
| 69D4 | tac | tac | phoA | ΔlacI::kan |
| 69D5 | tac | — | — | ΔlacI |
| 69D6 | — | tac | — | ΔlacI |
| 69D7 | — | — | tac | ΔlacI |
| 69D9 | tac | tac | phoA | lacI⁺ |
| 69E1 | phoA | — | CP25 | — |
| 69E3 | — | — | tac | lacI⁺ |
| 69F4 | tac | tac | CP25 | ΔlacI::kan |
| 69F8 | phoA | — | phoA | — |

— Dashes indicate no modifications to native promoter sequence.
[a]The genotype of the parent strain (67A6) has the lacI$^q$ mutation.

Example 2: Overexpression of FkpA Under the Control of Chromosomally Integrated Promoters Overexpression of FkpA was compared among strains engineered as described in Example 1 with an integrated promoter overexpressing native FkpA, as compared with strains harboring a plasmid expressing FkpA.

To assess the ability of FkpA to be chromosomally overexpressed, the native promoter of FkpA was exchanged with the tac, phoA, or CP25 promoter according to the methods of Example 1. Modifications to the lacI promoter were also made to further augment the strength of the tac promoter. Strains were grown in 10 liter fermentations and assessed for FkpA production by Western blot.

Figure 2:
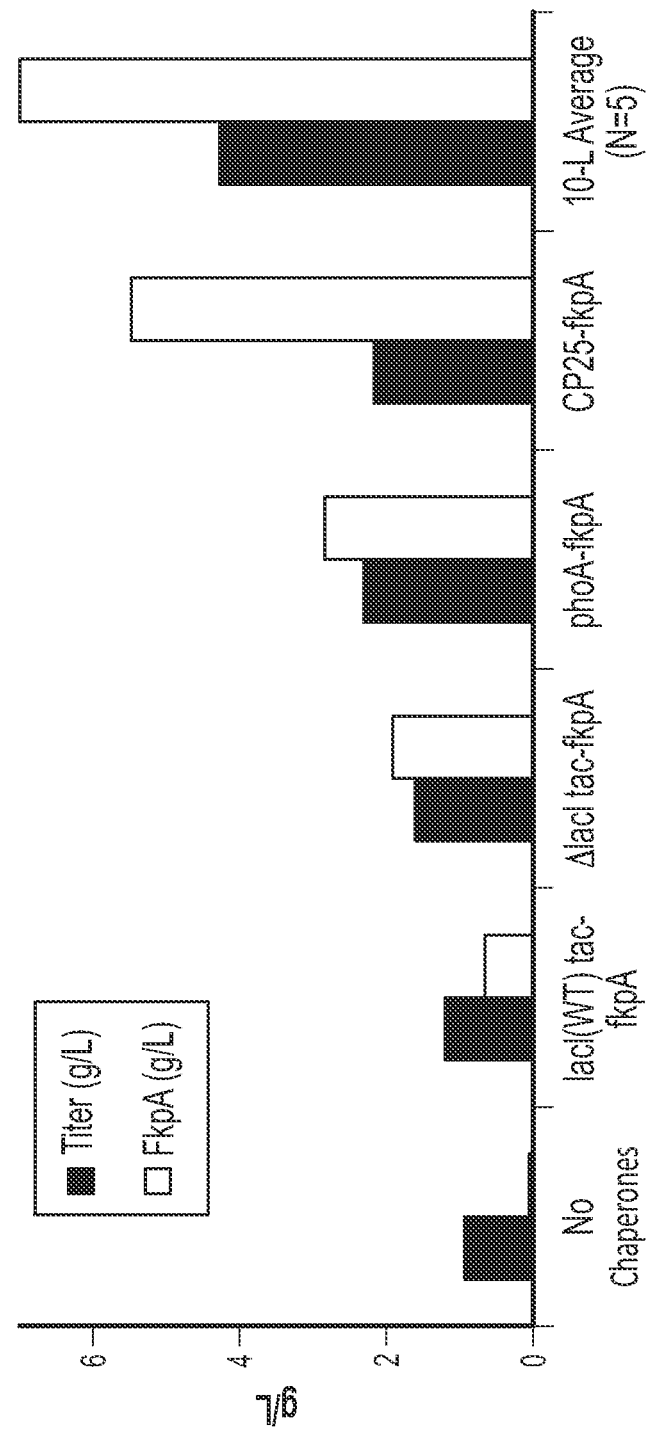
FIG. 2 shows the titer (black) and FkpA expression level (gray) of strains with the indicated promoter-fkpA pairings, as compared to a strain with plasmid-based expression of FkpA.

Chromosomal expression driven by the CP25 promoter showed the highest level of FkpA expression, followed by expression driven by the phoA promoter (FIG. 2). The tac promoter showed the lowest levels of FkpA expression, with higher FkpA expression in the ΔlacI background than in the lacI WT background, as expected.

As such, a range of FkpA expression was produced through chromosomal engineering, as compared with a single level of high expression through use of a plasmid-expressed fkpA locus. These results demonstrate that expression of FkpA can be controlled and augmented through chromosomal overexpression.

Example 3: Chromosomal Expression of Chaperones Under the Control of Tac, phoA, and CP25 Promoters in Shaker Flask Cultures To evaluate chaperone expression in strains with promoter modifications of DsbA, DsbC, and FkpA, cultures were grown in shake flasks, and the expression of these chaperones was measured using Western blot.

A range of expression levels was observed (FIGS. 3A-3C). For DsbA, expression from the CP25 promoter was the strongest, exceeding the level of expression seen in the positive controls (Sh. Fl. (+) and 10 L (+); DsbA expression from plasmid) (FIG. 3A). The next highest DsbA levels were produced by phoA then tac, and IPTG induction of the tac promoter raised expression levels of DsbA, as expected. Expression from the tac promoter alone was lower than the negative control (Sh. Fl. (−), no exogenous chaperone expression) likely due to the repressive lacI$^Q$ background of this strain. Similarly, DsbC expression was higher with the phoA promoter as compared to the tac promoter, with IPTG induction of the tac promoter leading to increased DsbC expression (FIG. 3B). DsbC expression from the tac promoter alone was also lower than the negative control (Sh. Fl. (−)).

Interestingly, FkpA expression was slightly different among the engineered strains when compared to DsbA and DsbC expression results (FIG. 3C). The phoA promoter drove the highest expression of FkpA, followed by expression from the CP25 promoter. As with DsbA and DsbC, the tac promoter drove the lowest level of expression. In general, expression levels of FkpA were much higher compared to native levels (Sh. Fl. (−)) implying that the native FkpA promoter is a weaker promoter compared to native DsbA and DsbC promoters.

Together, these results demonstrate that expression of the three chaperones DsbA, DsbC, and FkpA can all be similarly controlled and augmented through chromosomal overexpression.

Example 4: Chromosomal Expression of Chaperones Under the Control of Tac, phoA, and CP25 Promoters in ambr250 Fermentation Cultures In order to test whether chromosomal overexpression of chaperones could be translated from shake flask cultures to larger fermentation cultures, engineered strains were grown in ambr250 high cell density fermentations according to the methods in Example 1, and chaperone expression was measured by Western blot.

Figures 4A, 4B, 4C:
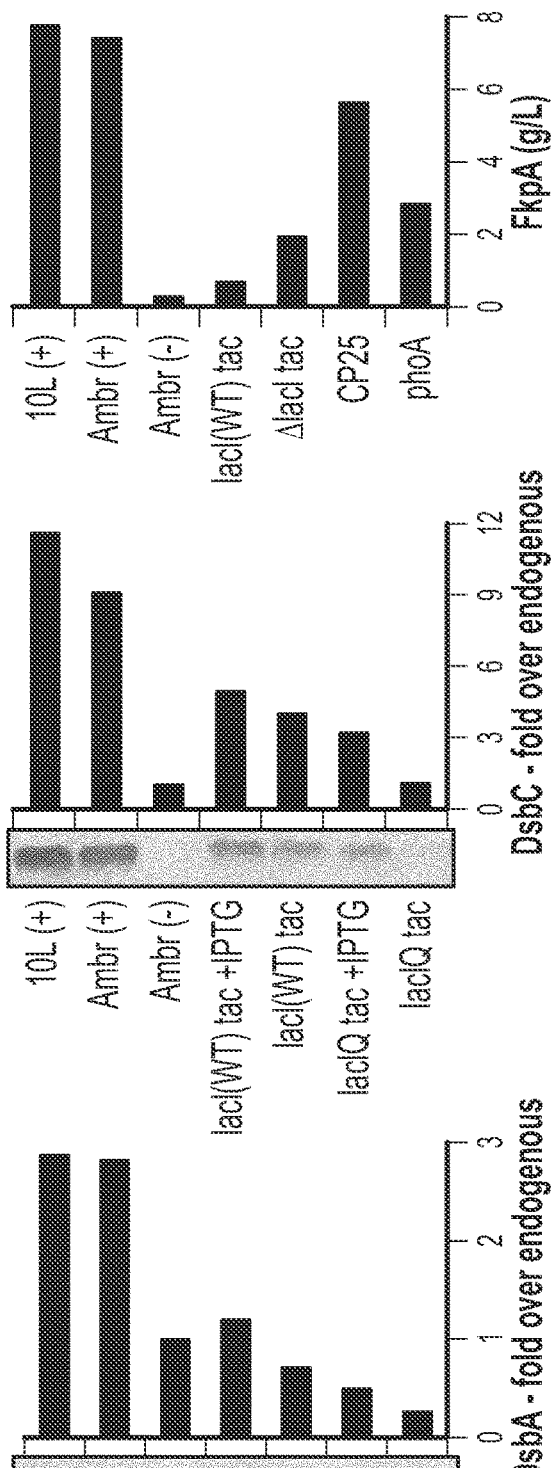
FIGS. 4A-4C show the relative chaperone expression levels (fold, over native expression levels) of DsbA (FIG. 4A), DsbC (FIG. 4B), or FkpA (FIG. 4C) in the indicated strains from 10 L fermentations. + represents positive control (plasmid chaperone expression), – represents negative control (no chaperone expression), and Ambr (–) refers to native expression level.

As with the shake flask cultures, a range of expression levels was observed (FIGS. 4A-4C). For DsbA and DsbC, only the tac promoter with different lacI backgrounds was tested. For both DsbA and DsbC, the tac promoter with the lacI$^Q$ background yielded the lowest level of expression, while the IPTG-induced tac promoter with the lacI WT background had the highest expression, as seen in shaker flask cultures (FIGS. 4A & 4B). Unlike FkpA expression in shake flasks, the CP25 promoter had the highest FkpA expression in ambR250 bioreactors when compared to phoA and tac promoters (FIG. 4C).

Together, these data indicate that expression patterns of chromosomally expressed chaperones can be successfully scaled up from shaker flask to a 10 L high cell density fermentation process.

Example 5: Expression of the xIL13Half-Antibody in Engineered Strains

The effect of chaperone overexpression in host strains (see Table B) on the production of the half-antibody xIL13 was tested.

Host strains were transformed with plasmid CS392, which expresses xIL13. Host strain 67A6, which does not contain chromosomally overexpressed chaperones, was transformed with plasmid MD157, which expresses xIL13 along with DsbA, DsbC, and FkpA (FIG. 1). 67A6/MD157 was used as a positive control. All strains were grown in 10 L fermentations as described in Example 1, and xIL13 production was assessed by reverse-phase HPLC titer assay.

The top three xIL13 producing strains (69E1, 69F8, and 69F4) produced greater or equal titers of xIL13 as compared to the positive control, where xIL13 was expressed from a plasmid (FIG. 5). The highest expression from strain 69E1 contained DsbC and FkpA driven by the phoA and CP25 promoters, respectively. These results also indicated that xIL13 titer was not significantly affected by the expression of DsbA.

Thus, chromosomal engineering as in the three engineered strains 69E1, 69F8, and 69F4 can be used as an alternative to co-expressing chaperones on a plasmid with xIL13, resulting in equivalent xIL13 titer.

Example 6: Expression of Chaperones and the xIL13 Half-Antibody in Engineered Strains 69E1, 69F4, and 69F8

To further investigate the use of strains 69E1, 69F4, and 69F8 in antibody-based product production, these strains were more closely evaluated for expression of xIL13 and chaperones over the course of 72 hours. The three engineered strains described in Example 5 were transformed with plasmid CS392 to express xIL13, as described in Examples 1 and 5. Strain 67A6 was transformed with plasmid MD157 as a positive control to express xIL13 and chaperones, as described in Example 1. All strains were grown in 10 L fermentations as described in Example 1 and xIL13 concentration was assessed by reverse-phase HPLC titer assay.

During fermentation, optical density (FIG. 6A) and osmolality (FIG. 6B) were measured. No significant differences were seen between the experimental strains and the plasmid control strain.

For all three experimental strains, xIL13 expression was similar to or slightly higher than the positive control, with strains 69E1 and 69F8 having the highest expression levels at 72 hours (FIG. 7A). The DsbC levels in engineered strain fermentations were lower compared to control process for a majority of the fermentations (FIG. 7B). This was expected since the plasmid based process has a much higher copy number than the process where chaperones are expressed from chromosome. The DsbC levels between 69E1 and 69F8 strain fermentations were similar, which was expected since both use phoA promoter for expression. Interestingly, the levels were similar to the plasmid expression levels towards the end of the fermentation. DsbC was expressed from phoA promoter in 69E1 and 69F8 strains, so the levels were lower during the initial part of the fermentation since the promoter was not induced until 18 hrs into the fermentation due to the presence of phosphate. Phosphate was completely consumed by ~18 hrs and after which the promoter is fully induced resulting in more DsbC expression. The DsbC levels in 69F4 fermentation were higher initially compared to 69E1 and 69F8 strain fermentations since 69F4 uses a leaky tac promoter and is independent of phosphate levels in the media. These results also indicate that the phoA promoter is a stronger promoter compared to tac promoter similar to the expression results obtained in shake flask cultures.

Strains 69E1 and 69F4 express FkpA under a CP25 promoter whereas 69F8 expresses FkpA under a phoA promoter. The strong constitutive CP25 promoter resulted in high levels of FkpA comparable to the plasmid levels (where FkpA is under phoA promoter; FIG. 7C). The 69F8 strain accumulated FkpA at lower levels compared to the plasmid-based process, which may be due to copy number differences (~15 for plasmid and 1 for chromosome) even though both cases use the phoA promoter to drive FkpA expression. However, titers (FIG. 7A) between Phase I plasmid based process and in 69F8 strain process were similar, suggesting that additional FkpA may not be necessary. Due to the burden imposed upon purification development to reduce FkpA levels in the final pool, reduced FkpA levels with the ability to achieve high titers may be considered an advantage of strain 69F8 for the xIL13 process.

These data suggest that the expression of xIL13 does not necessarily require high levels of DsbC and FkpA compared to the plasmid control. Equivalent or higher titers of xIL13 could be produced from all three strains, even though the strains generally expressed lower levels of chaperones (although this feature is advantageous in that it obviates the need for further purification to remove FkpA).

Example 7: Expression of the AF2 Half-Antibody in Engineered Strains 69E1, 69F4, and 69F8

The ability of strains 69E1, 69F4, and 69F8 to produce the half-antibody AF2 was assessed. 69E1, 69F4, and 69F8 strains were transformed with plasmid ERD046 to express AF2, and strain 67A6 was transformed with plasmid MD341 as a positive control to express AF2 and chaperones, as described in Example 1. Strains were grown in 10 L fermentations as described in Example 1 and AF2 concentration was assessed as various time points over the course of 72 hours.

Figure 9:
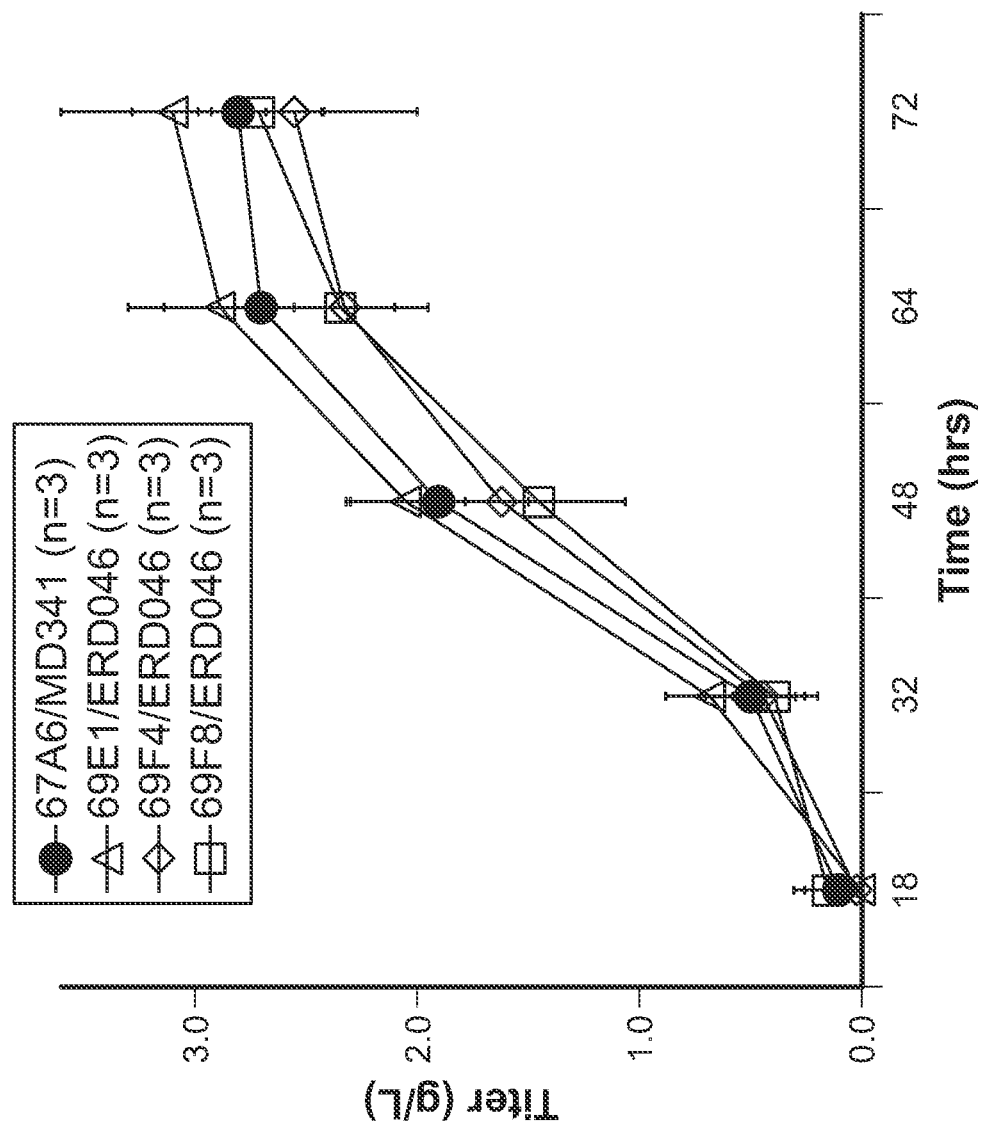
FIG. 9 shows the AF2 titer (g/L) produced by the indicated strains over time.
Figure 10A:
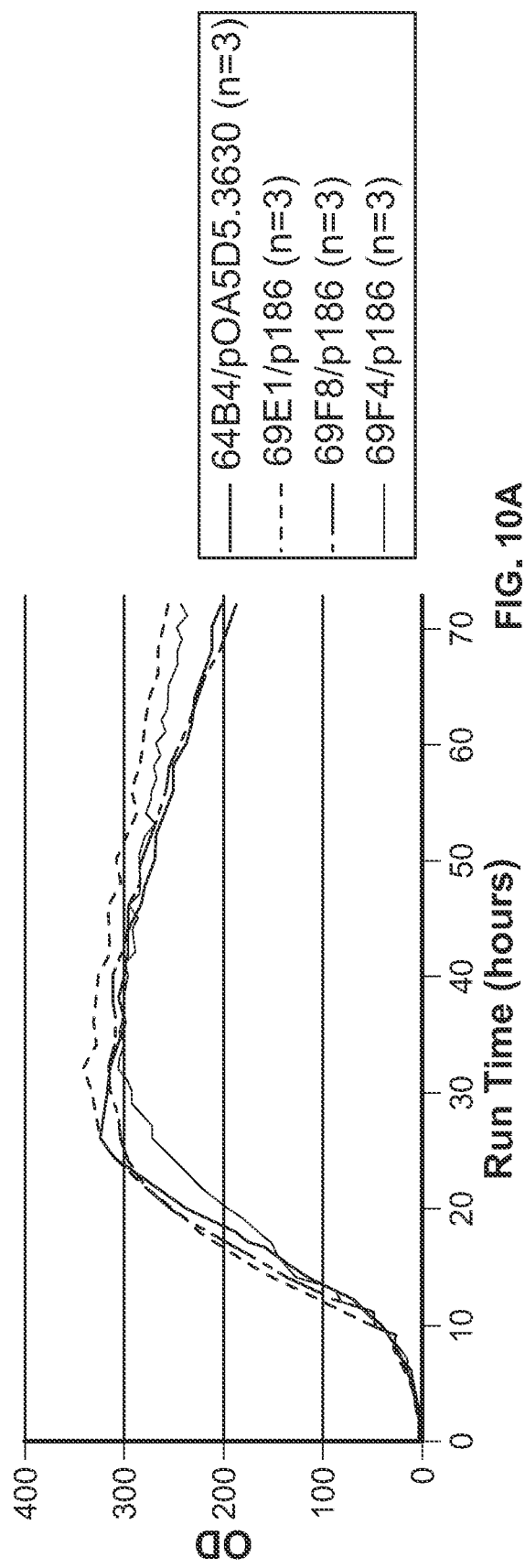
FIGS. 10A & 10B show the optical density (OD.
Figure 10B:
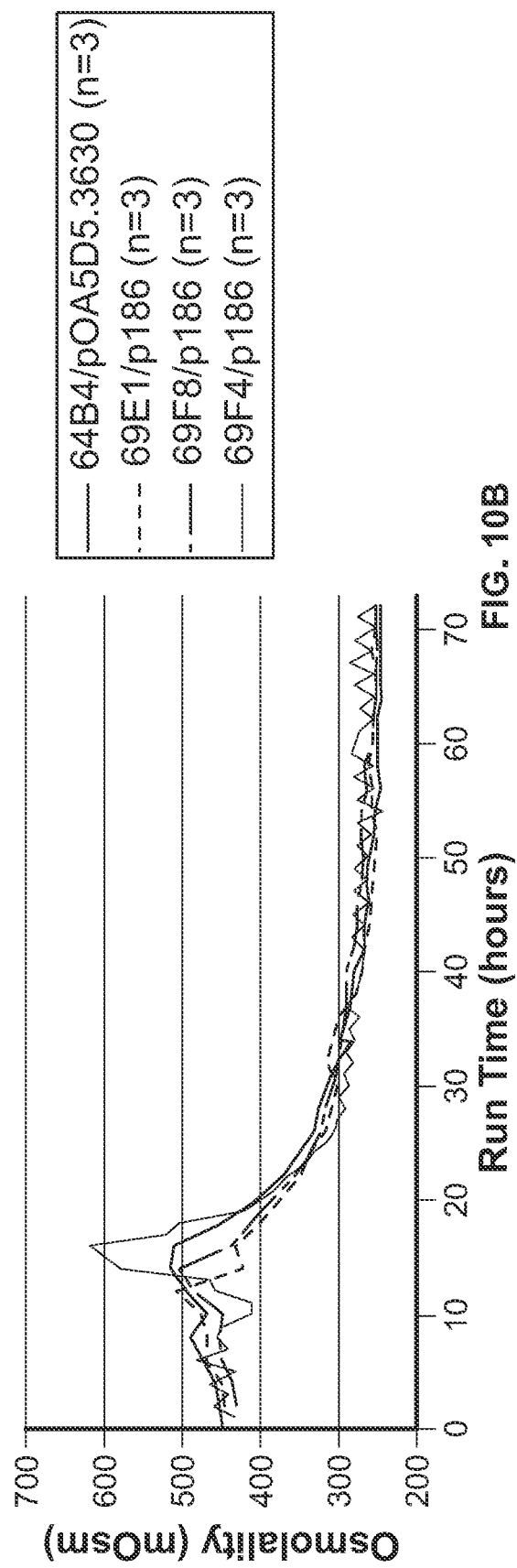

During fermentation, optical density (FIG. 8A) and osmolality (FIG. 8B) were measured. No significant differences were seen between the experimental strains and the plasmid control strain. Expression of AF2 was highest in strain 69E1, surpassing the titer seen in the plasmid control (FIG. 9). Strains 69F4 and 69F8 had slightly lower but comparable titers of AF2 as compared to the control.

These data demonstrate that all three strains, particularly strain 69E1, can be used as an alternative to expressing chaperones on plasmids when producing AF2.

Example 8: Expression of the MetMAb One-Armed Antibody in Engineered Strains 69E1, 69F4, and 69F8

The ability of strains 69E1, 69F4, and 69F8 to produce the one-armed antibody MetMAb was assessed. These three strains were transformed with plasmid p186 to express MetMAb, and strain 64B4 was transformed with plasmid pOA5D5.3630 as a positive control to express MetMAb and chaperones, as described in Example 1. Strains were grown in 10 L fermentations as described in Example 1, and MetMAb concentration was assessed as various time points over the course of 72 hours.

During fermentation, optical density (FIG. 10A) and osmolality (FIG. 10B) were measured. No significant differences were seen between the experimental strains and the plasmid control strain.

Figure 11:
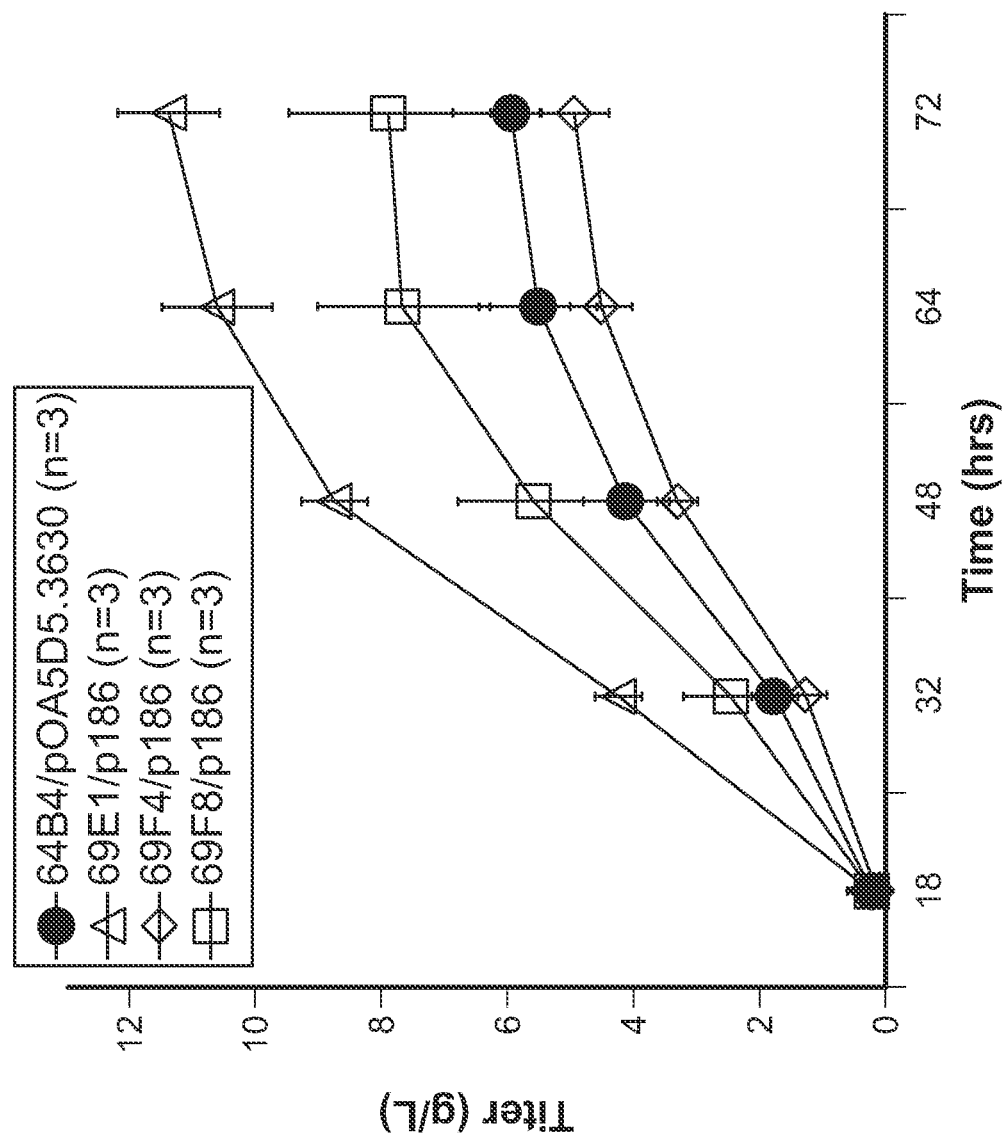
FIG. 11 shows the MetMAb titer (g/L) produced by the indicated strains over time.

In the control process, DsbA and DsbC were expressed from plasmid and FkpA was not used. Fermentations using all three strains had comparable or higher titers when compared to the control process (FIG. 11). Fermentations using the 69E1 strain had an approximately 2-fold increase in titers compared to control process. Surprisingly the fermentation using the 69F4 strain did not accumulate titers similar to the 69E1 strain. Without wishing to be bound to theory, this could be due to sub-optimal levels of DsbC expressed under tac promoter in this strain, compared to phoA promoter (a stronger promoter) in the 69E1 strain. Fermentations using the 69E8 strain had similar titers as the control process. Without wishing to be bound to theory, this could be due to sub-optimal levels of FkpA.

Example 9: Expression of the Anti-VEGF Antibody Fragment in Engineered Strain 69E1

The ability of strain 69E1 to produce an anti-VEGF Fab fragment was assessed. Strain 69E1 and the control strain 67A6 were transformed with plasmid HSK117 to express the anti-VEGF antibody fragment, as described in Example 1. Strains were grown in 10 L fermentations as described in Example 1 and anti-VEGF antibody fragment concentration was assessed as various time points over the course of 72 hours.

Figure 12A:
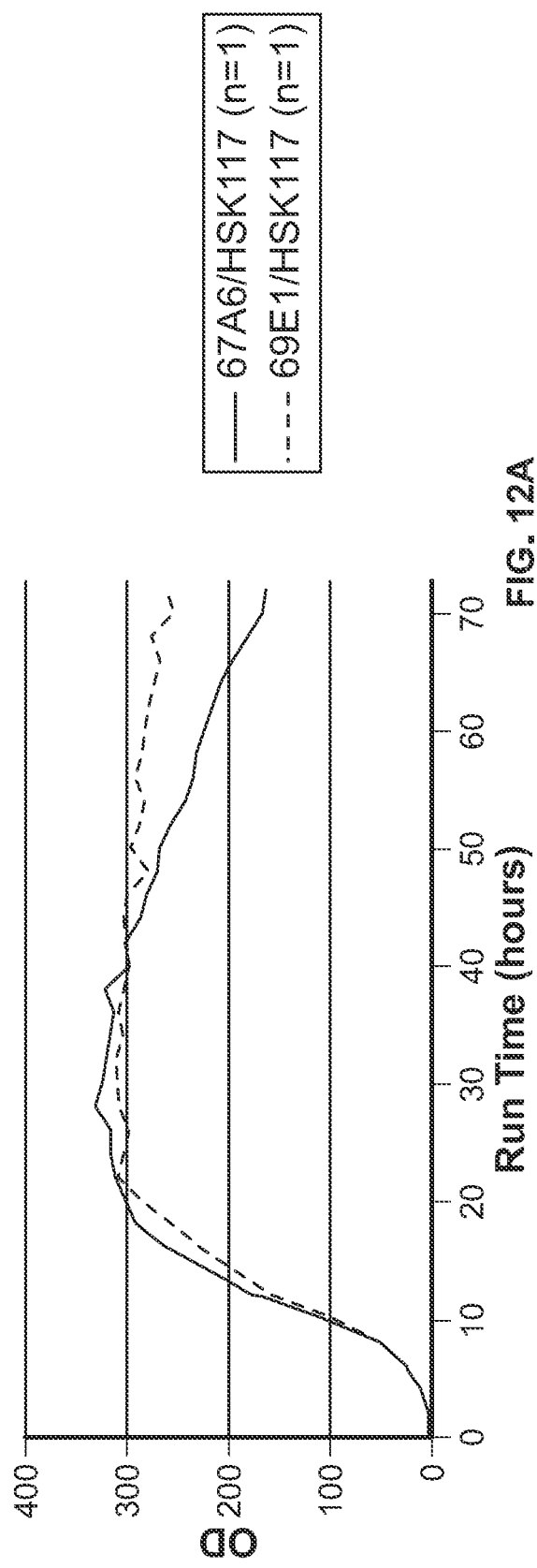
FIGS. 12A & 12B show the optical density (OD.
Figure 12B:
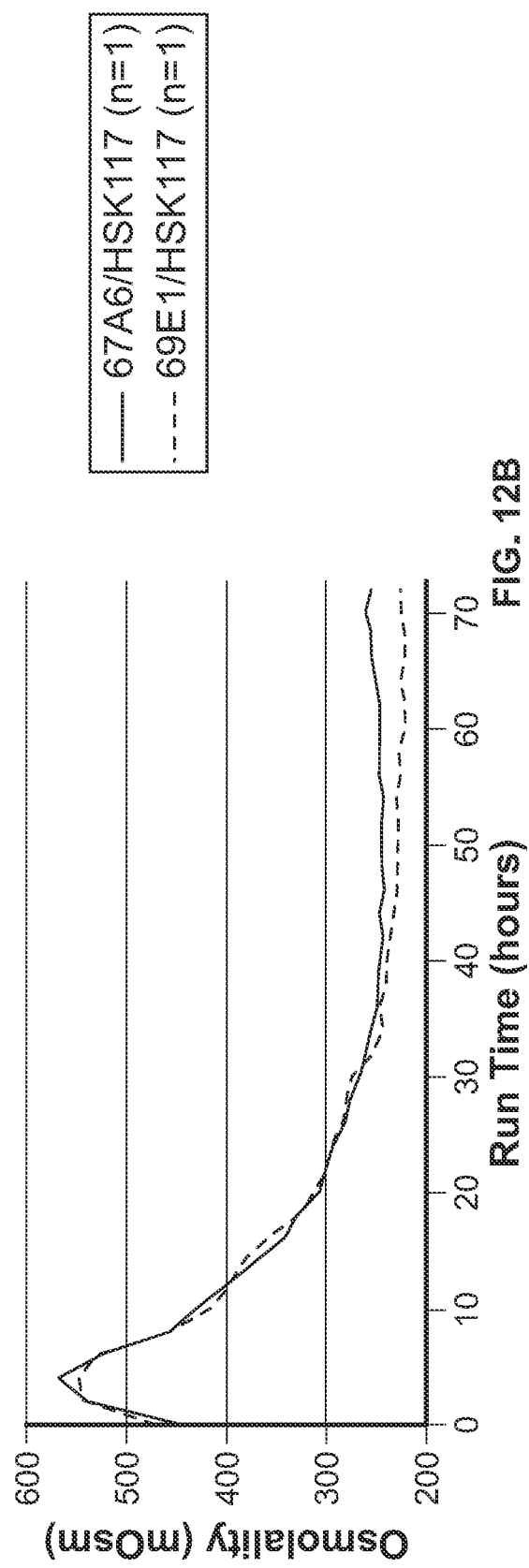
Figure 13:
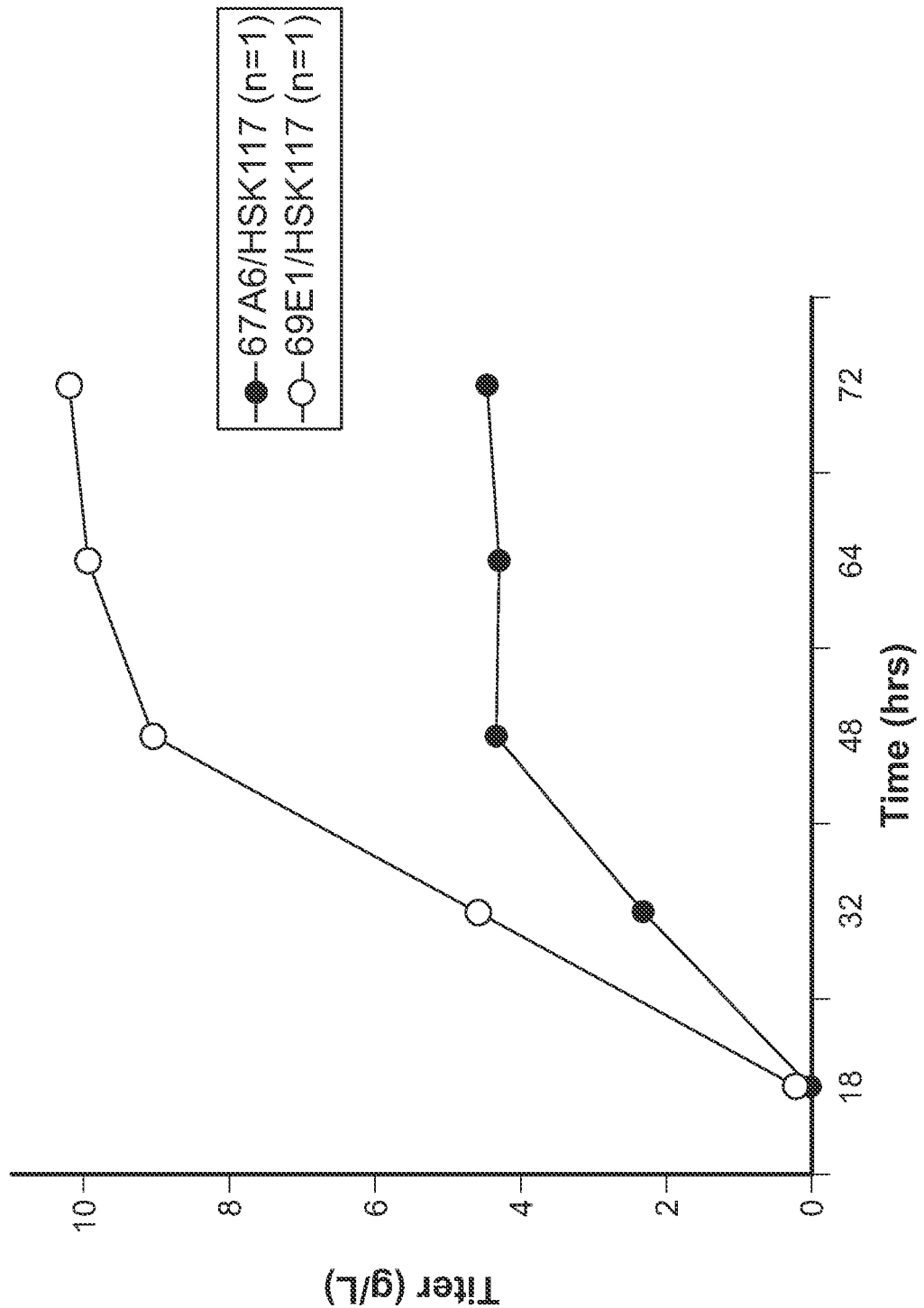
FIG. 13 shows the anti-VEGF antibody fragment titer (g/L) produced by the indicated strains over time.

During fermentation, optical density (FIG. 12A) and osmolality (FIG. 12B) were measured. Strain 69E1 showed slightly higher optical density at 72 hours than the control (FIG. 12A). Expression of anti-VEGF antibody fragment in strain 69E1 also exceeded that of the plasmid control at all time points tested (FIG. 13).

These data demonstrate that strains with chromosomal chaperone overexpression can be used to produce higher titers of anti-VEGF antibody fragment, as compared with strains using plasmid-based chaperone overexpression.

Taken together, the results of Examples 5-9 demonstrate that chromosomal overexpression of chaperones has the potential to yield comparable titers to plasmid based chaperone expression. Several molecule formats were tested including the bispecific half-antibodies xIL13 and AF2, the one-armed antibody MetMAb, and an anti-VEGF Fab fragment. Fermentations using the three engineered strains 69E1, 68F8, and 69F4 had comparable or higher titers compared to the control process with little to no additional process development. Moreover, since no additional development was performed in the case studies beyond a control in one case (for AF2 with 69F8 host), it is possible that further process development efforts could be performed on a molecule-by-molecule basis to further drive titers beyond the levels observed here. In addition to achieving high titers, these strains offer a quick and easy way for chaperone expression to be evaluated without requiring additional plasmid cloning work. In some cases (e.g. 69F8 strain in xIL13 process), similar titers were obtained with lower levels of FkpA, which is desirable for downstream purification since additional column purification is not needed for clearance of FkpA.

What is claimed is:

1. A method of producing a polypeptide comprising two chains in a prokaryotic host cell comprising a host cell chromosome, the method comprising:
   (a) culturing the host cell to express the two chains of the polypeptide in a culture medium under conditions suitable for expression of the two chains of the polypeptide, whereby upon expression the two chains fold and assemble to form a biologically active polypeptide in the host cell;
   wherein the host cell is an *Escherichia coli* (*E. coli*) strain, and wherein the host cell comprises:
   (1) a first polynucleotide comprising a first translational unit encoding a first chain of the polypeptide;
   (2) a second polynucleotide comprising a second translational unit encoding a second chain of the polypeptide, wherein the first and second polynucleotides are part of one or more extra-chromosomal polynucleotides;
   (3) a third polynucleotide comprising a third translational unit encoding a protein disulfide oxidoreductase, wherein the third translational unit is part of and native to the host cell chromosome, wherein the third translational unit is in operable combination with a first promoter that is integrated in the host cell chromosome and drives transcription of the third translational unit, and wherein the combination of the third translational unit and the first promoter is non-native to the host cell chromosome; and
   (4) a fourth polynucleotide comprising a fourth translational unit encoding a peptidyl-prolyl isomerase, wherein the fourth translational unit is part of and native to the host cell chromosome, wherein the fourth translational unit is in operable combination with a second promoter that is integrated in the host cell chromosome and drives transcription of the fourth translational unit, and wherein the combination of the fourth translational unit and the second promoter is non-native to the host cell chromosome; and
   (b) recovering the biologically active polypeptide from the host cell,
   wherein:
      the protein disulfide oxidoreductase is *E. coli* DsbC, wherein the first promoter is a Pho promoter that drives transcription of the third translational unit when phosphate in the culture medium has been depleted, wherein the peptidyl-prolyl isomerase is *E. coli* FkpA, and wherein the second promoter is a CP25 promoter; or
      the protein disulfide oxidoreductase is *E. coli* DsbC, wherein the first promoter is a Pho promoter that drives transcription of the third translational unit when phosphate in the culture medium has been depleted, wherein the peptidyl-prolyl isomerase is *E. coli* FkpA, and wherein the second promoter is a Pho promoter that drives transcription of the fourth translational unit when phosphate in the culture medium has been depleted.

2. The method of claim 1, wherein the protein disulfide oxidoreductase is *E. coli* DsbC, wherein the first promoter is a Pho promoter that drives transcription of the third translational unit when phosphate in the culture medium has been depleted, wherein the peptidyl-prolyl isomerase is *E. coli* FkpA, and wherein the second promoter is a CP25 promoter.

3. The method of claim 1, wherein the protein disulfide oxidoreductase is *E. coli* DsbC, wherein the first promoter is a Pho promoter that drives transcription of the third translational unit when phosphate in the culture medium has been depleted, wherein the peptidyl-prolyl isomerase is *E. coli* FkpA, and wherein the second promoter is a Pho promoter that drives transcription of the fourth translational unit when phosphate in the culture medium has been depleted.

4. The method of claim 1, wherein the polypeptide is a half antibody in which the first chain and the second chain comprise an immunoglobulin heavy chain and an immunoglobulin light chain.

5. A method of producing a bispecific antibody comprising a first half antibody capable of binding a first antigen and a second half antibody capable of binding a second antigen, the method comprising:
   producing the first half antibody according to the method of claim 1, wherein the first translational unit encodes the heavy chain of the first half antibody and the second translational unit encodes the light chain of the first half antibody, and wherein the first half antibody comprises at least one knob-forming mutation;
   producing the second half antibody according to the method of claim 1, wherein the first translational unit encodes the heavy chain of the second half antibody and the second translational unit encodes the light chain of the second half antibody, and wherein the second half antibody comprises at least one hole-forming mutation;
   combining, in a reducing condition, the first half antibody with the second half antibody to produce the bispecific antibody.

6. The method of claim 5, wherein the first antigen and the second antigen are different antigens.

7. The method of claim 5, further comprising the step of adding a reducing agent to achieve the reducing condition.

8. The method of claim 7, wherein the reducing agent is glutathione.

9. The method of claim 1, wherein the *E. coli* is of a strain deficient in endogenous protease activity and/or with enhanced LacI production or activity.

10. The method of claim 9, wherein the *E. coli* is a strain with a degpS210A mutation and a lacI$^Q$ mutation.

11. A method of producing a polypeptide comprising two chains in a prokaryotic host cell comprising a host cell chromosome, the method comprising:
  (a) culturing the host cell to express the two chains of the polypeptide in a culture medium under conditions suitable for expression of the two chains of the polypeptide, whereby upon expression the two chains fold and assemble to form a biologically active polypeptide in the host cell;
  wherein the host cell is an *Escherichia coli* (*E. coli*) strain, and wherein the host cell comprises:
(1) a first polynucleotide comprising a first translational unit encoding a first chain of the polypeptide;
(2) a second polynucleotide comprising a second translational unit encoding a second chain of the polypeptide, wherein the first and second polynucleotides are part of one or more extra-chromosomal polynucleotides;
(3) a third polynucleotide comprising a third translational unit encoding a protein disulfide oxidoreductase, wherein the third translational unit is part of and native to the host cell chromosome, wherein the third translational unit is in operable combination with a first promoter that is integrated in the host cell chromosome and drives transcription of the third translational unit, and wherein the combination of the third translational unit and the first promoter is non-native to the host cell chromosome;
(4) a fourth polynucleotide comprising a fourth translational unit encoding a peptidyl-prolyl isomerase, wherein the fourth translational unit is part of and native to the host cell chromosome, wherein the fourth translational unit is in operable combination with a second promoter that is integrated in the host cell chromosome and drives transcription of the fourth translational unit, and wherein the combination of the fourth translational unit and the second promoter is non-native to the host cell chromosome; and
(5) a fifth polynucleotide comprising a fifth translational unit encoding a second protein disulfide oxidoreductase, wherein the fifth translational unit is part of and native to the host cell chromosome, wherein the fifth translational unit is in operable combination with a third promoter that is integrated in the host cell chromosome and drives transcription of the fifth translational unit, and wherein the combination of the fifth translational unit and the third promoter is non-native to the host cell chromosome; and
  (b) recovering the biologically active polypeptide from the host cell,
wherein the first protein disulfide oxidoreductase is *E. coli* DsbC, wherein the first promoter is an isopropyl beta-D-thiogalactoside (IPTG)-inducible promoter that drives transcription of the third translational unit when IPTG is present in the culture medium, wherein the peptidyl-prolyl isomerase is *E. coli* FkpA, wherein the second promoter is a CP25 promoter, wherein the second protein disulfide oxidoreductase is *E. coli* DsbA, wherein the third promoter is an isopropyl beta-D-thiogalactoside (IPTG)-inducible promoter that drives transcription of the fifth translational unit when IPTG is present in the culture medium.

12. The method of claim 11, wherein the host cell further comprises:
  (6) a sixth polynucleotide comprising a sixth translational unit encoding a third chain of the polypeptide, wherein the sixth polynucleotide is part of the one or more extra-chromosomal polynucleotides;
  whereby upon expression the three chains fold and assemble to form a biologically active polypeptide in the host cell.

13. The method of claim 12, wherein the first translational unit encodes an immunoglobulin heavy chain, wherein the second translational unit encodes an immunoglobulin light chain, wherein the sixth translational unit encodes an immunoglobulin Fc fragment, and wherein the three chains fold and assemble to form a biologically active monovalent antibody.

14. The method of claim 11, wherein the *E. coli* is of a strain deficient in endogenous protease activity and/or with enhanced LacI production or activity.

15. The method of claim 14, wherein the *E. coli* is a strain with a degpS210A mutation and a lacI$^Q$ mutation.

* * * * *